US006527759B1

(12) United States Patent
Tachibana et al.

(10) Patent No.: US 6,527,759 B1
(45) Date of Patent: Mar. 4, 2003

(54) ULTRASOUND ASSEMBLY FOR USE WITH LIGHT ACTIVATED DRUGS

(75) Inventors: Katsuro Tachibana, Fukuoka (JP); Shunro Tachibana, Fukuoka (JP); James R. Anderson, Redmond, WA (US); Gary Lichttenegger, Woodinville, WA (US)

(73) Assignee: Ekos Corporation, Bothell, WA (US)

( * ) Notice: Subject to any disclaimer, the term of this patent is extended or adjusted under 35 U.S.C. 154(b) by 0 days.

(21) Appl. No.: 09/620,701

(22) Filed: Jul. 20, 2000

Related U.S. Application Data

(62) Division of application No. 09/158,316, filed on Sep. 21, 1998, now Pat. No. 6,176,842, which is a continuation-in-part of application No. 09/129,980, filed on Aug. 5, 1998, now Pat. No. 6,210,356, which is a continuation-in-part of application No. 08/972,846, filed on Nov. 18, 1997, now abandoned, which is a continuation of application No. 08/611,105, filed on Mar. 5, 1996, now abandoned.

(30) Foreign Application Priority Data

Mar. 5, 1995 (JP) .......................................... P7-048710
Sep. 19, 1997 (JP) .............................................. 9-70617

(51) Int. Cl.[7] .............................................. A61M 31/00
(52) U.S. Cl. ........................ 604/500; 604/509; 604/522; 604/22
(58) Field of Search .............................. 604/21–22, 500, 604/101.01, 101.03, 507–509, 522; 607/97; 601/2, 3; 514/410, 145

(56) References Cited

U.S. PATENT DOCUMENTS

| 3,433,226 A | 3/1969 | Boyd ........................... 128/305 |
| 4,027,659 A | 6/1977 | Slingluff ..................... 128/2 M |
| 4,040,414 A | 8/1977 | Suroff .......................... 128/24 |
| 4,319,580 A | 3/1982 | Colley et al. ................ 128/661 |
| 4,354,502 A | 10/1982 | Colley et al. ................ 128/663 |
| 4,512,762 A | 4/1985 | Spears ......................... 604/21 |
| 4,531,943 A | 7/1985 | Van Tassel et al. ......... 604/280 |
| 4,582,067 A | 4/1986 | Silverstein et al. |
| 4,750,902 A | 6/1988 | Wuchinich et al. ........... 604/22 |
| 4,767,402 A | 8/1988 | Kost et al. ..................... 604/49 |
| 4,780,212 A | 10/1988 | Kost et al. ................... 210/646 |
| 4,808,153 A | 2/1989 | Parisi .......................... 604/22 |
| 4,870,953 A | 10/1989 | Don Michael et al. ........ 128/24 |

(List continued on next page.)

FOREIGN PATENT DOCUMENTS

| DE | 39 19 592 A1 | 2/1990 | .......... A61B/17/22 |
| DE | 40 05 743 | 8/1991 | .......... A61H/23/00 |
| EP | 0 529 675 | 8/1992 | .......... A61B/17/06 |

(List continued on next page.)

OTHER PUBLICATIONS

Hynynen et al.; "Small Cylindrical Ultrasound Sources For Induction of Hyperthermia Via Body Cavities or Interstitial Implants"; *Arizona Cancer Center and Department of Radiation Oncology, University of Arizona Health Sciences Center*; vol. 9, No. 2; pp. 263–274; 1993.

(List continued on next page.)

*Primary Examiner*—Mark Bockelman
(74) *Attorney, Agent, or Firm*—Knobbe, Martens, Olson & Bear, LLP

(57) ABSTRACT

A kit and method for causing tissue death within a tissue site is disclosed. The kit includes a media with a light activated drug activatable upon exposure to a particular level of ultrasound energy. The kit also includes a catheter with a lumen coupled with a media delivery port through which the light activated drug can be locally delivered to the tissue site. The ultrasound transducer is configured to transmit the level of ultrasound energy which activates the light activated drug with sufficient power that the ultrasound energy can penetrate the tissue site.

28 Claims, 59 Drawing Sheets

U.S. PATENT DOCUMENTS

| | | | | |
|---|---|---|---|---|
| 4,877,031 | A | 10/1989 | Conway et al. | 128/344 |
| 4,917,088 | A | 4/1990 | Crittendon | 606/194 |
| 4,917,102 | A | 4/1990 | Miller et al. | 128/772 |
| 4,920,954 | A | 5/1990 | Alliger et al. | 128/24 |
| 4,924,863 | A | 5/1990 | Sterzer | 606/27 |
| 4,936,281 | A | 6/1990 | Stasz | 128/660.03 |
| 4,955,863 | A | 9/1990 | Walker et al. | 604/165 |
| 4,971,991 | A | 11/1990 | Umemura et al. | 514/410 |
| 4,992,257 | A | 2/1991 | Bonnett et al. | 424/9 |
| 5,021,044 | A | 6/1991 | Sharawy | 604/53 |
| 5,149,319 | A | 9/1992 | Unger | 604/22 |
| 5,158,071 | A | 10/1992 | Umemura et al. | 128/24 |
| 5,163,421 | A | 11/1992 | Bernstein et al. | 128/24.1 |
| 5,190,766 | A | 3/1993 | Ishihara | 424/489 |
| 5,197,946 | A | 3/1993 | Tachibana | 604/22 |
| 5,250,034 | A | 10/1993 | Appling et al. | 604/164 |
| 5,267,954 | A | 12/1993 | Nita | 604/22 |
| 5,267,985 | A | 12/1993 | Shimada et al. | 604/290 |
| 5,269,291 | A | 12/1993 | Carter | 128/24 |
| 5,282,785 | A | 2/1994 | Shapland et al. | 604/21 |
| 5,286,254 | A | 2/1994 | Shapland et al. | 604/21 |
| 5,295,484 | A | 3/1994 | Marcus et al. | 128/660.03 |
| 5,304,115 | A | 4/1994 | Pflueger et al. | 604/22 |
| 5,318,014 | A | 6/1994 | Carter | 601/2 |
| 5,323,769 | A | 6/1994 | Bommannan et al. | 601/2 |
| 5,327,891 | A | 7/1994 | Rammler | 128/658 |
| 5,328,470 | A | 7/1994 | Nabel et al. | 604/101 |
| 5,344,435 | A | 9/1994 | Turner et al. | 607/101 |
| 5,345,940 | A | 9/1994 | Seward et al. | 128/662.06 |
| 5,353,798 | A | 10/1994 | Sieben | 128/662.06 |
| 5,354,279 | A | 10/1994 | Hofling | 604/164 |
| 5,362,309 | A | 11/1994 | Carter | 604/22 |
| 5,363,853 | A | 11/1994 | Lieber | 128/662.06 |
| 5,368,036 | A | 11/1994 | Tanaka et al. | |
| 5,380,273 | A | 1/1995 | Dubrul et al. | 604/22 |
| 5,390,678 | A | 2/1995 | Gesswein et al. | 128/662.06 |
| 5,421,338 | A | 6/1995 | Crowley et al. | 128/662.06 |
| 5,423,797 | A | 6/1995 | Sorin et al. | 606/1 |
| 5,431,663 | A | 7/1995 | Carter | 604/128 |
| 5,445,155 | A | 8/1995 | Sieben | 128/660.07 |
| 5,447,509 | A | 9/1995 | Mills et al. | 606/1 |
| 5,458,568 | A | 10/1995 | Racchini et al. | 604/19 |
| 5,465,726 | A | 11/1995 | Dickinson et al. | 128/663.01 |
| 5,474,530 | A | 12/1995 | Passafaro et al. | 604/22 |
| 5,474,531 | A | 12/1995 | Carter | 604/22 |
| 5,489,279 | A | 2/1996 | Meserol | 604/20 |
| 5,498,238 | A | 3/1996 | Shapland et al. | 604/53 |
| 5,509,896 | A | 4/1996 | Carter | 604/21 |
| 5,514,092 | A | 5/1996 | Forman et al. | 604/101 |
| 5,520,189 | A | 5/1996 | Malinowski et al. | 128/662.03 |
| 5,567,687 | A | 10/1996 | Magda et al. | 514/44 |
| 5,594,136 | A | 1/1997 | Sessler et al. | 540/472 |
| 5,599,923 | A | 2/1997 | Sessler et al. | 540/145 |
| 5,603,327 | A | 2/1997 | Eberle | 128/662.06 |
| 5,606,974 | A | 3/1997 | Castellano et al. | 128/662.06 |
| 5,616,342 | A | 4/1997 | Lyons | 424/450 |
| 5,617,851 | A | 4/1997 | Lipkovker | 128/632 |
| 5,618,275 | A | 4/1997 | Bock | 604/290 |
| 5,620,479 | A | 4/1997 | Diederich | 607/97 |
| 5,628,728 | A | 5/1997 | Tachibana et al. | |
| 5,628,730 | A | 5/1997 | Shapland | 604/21 |
| 5,630,837 | A | 5/1997 | Crowley | |
| 5,632,970 | A | 5/1997 | Sessler et al. | 425/9.61 |
| 5,660,180 | A | 8/1997 | Malinowski et al. | 128/660.03 |
| 5,663,327 | A | 9/1997 | Tarabo et al. | 540/239 |
| 5,695,460 | A | 12/1997 | Siegal et al. | 604/21 |
| 5,707,608 | A | 1/1998 | Liu | 424/9.61 |
| 5,725,494 | A | 3/1998 | Brisken | 604/22 |
| 5,735,811 | A | 4/1998 | Brisken | 604/22 |
| 5,770,222 | A | 6/1998 | Unger et al. | 424/450 |
| 5,916,192 | A | 6/1999 | Nita et al. | |
| 5,997,497 | A | 12/1999 | Nita et al. | |
| 6,001,069 | A | 12/1999 | Tachibana et al. | |
| 6,024,718 | A | 2/2000 | Chen et al. | |
| 6,096,000 | A | 8/2000 | Tachibana et al. | |
| 6,210,356 | B1 | 4/2001 | Anderson et al. | |
| 6,228,046 | B1 | 5/2001 | Brisken | |
| 6,287,271 | B1 | 9/2001 | Dubrul et al. | |

FOREIGN PATENT DOCUMENTS

| | | | |
|---|---|---|---|
| EP | 0 629 382 | 11/1993 | A61B/17/36 |
| EP | 668052 A2 | 2/1995 | |
| WO | WO 89/04142 | 5/1989 | A61B/8/12 |
| WO | WO 91/09629 | 7/1991 | A61K/49/00 |
| WO | WO 92/07622 | 5/1992 | A61N/5/02 |
| WO | WO 93/08738 | 5/1993 | |
| WO | WO 94/05361 | 3/1994 | A61M/25/00 |
| WO | WO 95/01751 | 1/1995 | A61B/8/12 |
| WO | WO 96/27341 | 9/1996 | A61B/19/00 |
| WO | WO 96/29935 | 10/1996 | A61B/8/12 |
| WO | WO 96/35469 | 11/1996 | A61M/25/00 |
| WO | WO 96/36286 | 11/1996 | A61B/17/20 |
| WO | WO 97/19645 | 6/1997 | |
| WO | WO 98/11826 | 3/1998 | A61B/17/00 |
| WO | WO 98/48711 | 11/1998 | A61B/17/22 |

OTHER PUBLICATIONS

Lee et al.; "Arrays of Multielement Ultrasound Applicators For Interstitial Hyperthermia"; *IEEE Transactions on Biomedical Engineering*; vol. 46, No. 7; Jul. 1999.

G. Maywald et al., "Experience With Atraumatic Vascular Diagnosis With The Aid of the Ultrasonic Doppler Technique", Electromedica, vol. 2, pp. 43–48 (1976).

Japanese Journal of Cancer Research, vol. 81, No. 3, Mar. 1990, pp. 304–308.

Cancer Letters, vol. 78 (1–3), 1994, pp. 177–181.

Cancer Letters vol. 72, 1993, pp. 195–199.

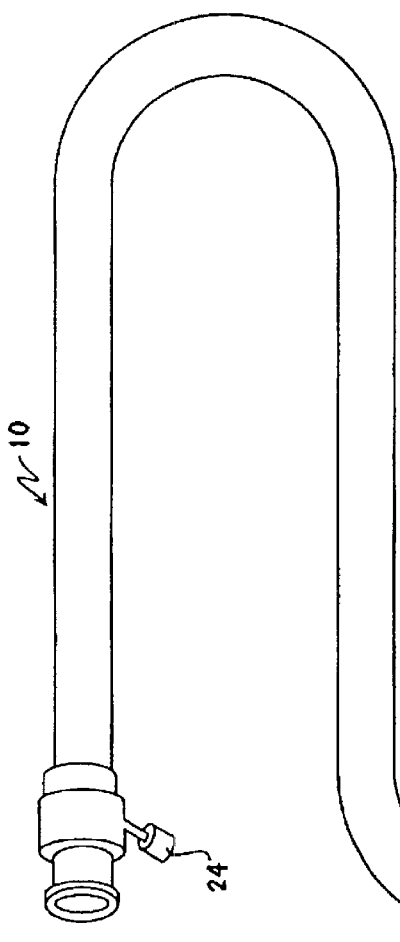
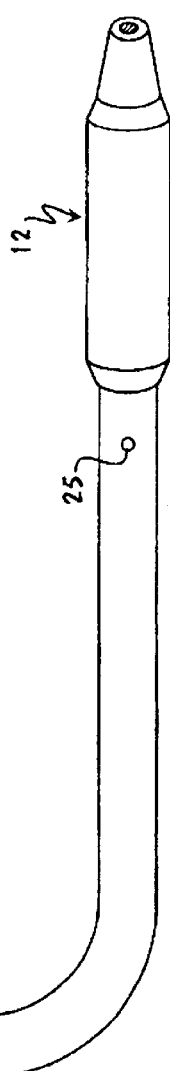
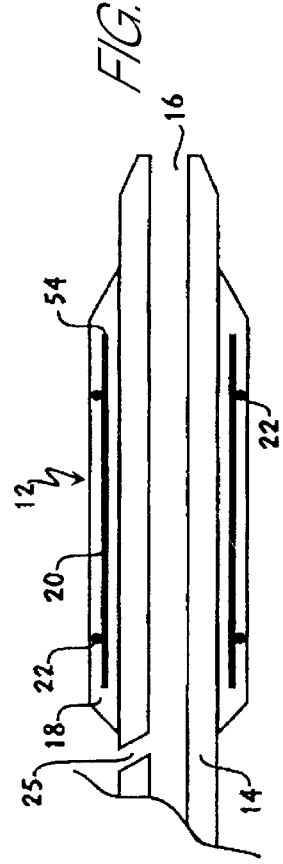
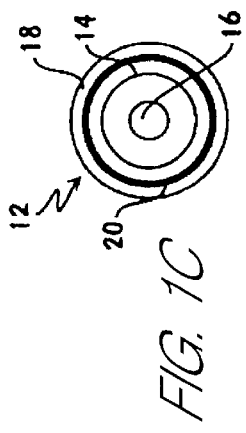
FIG. 1A
FIG. 1B
FIG. 1C

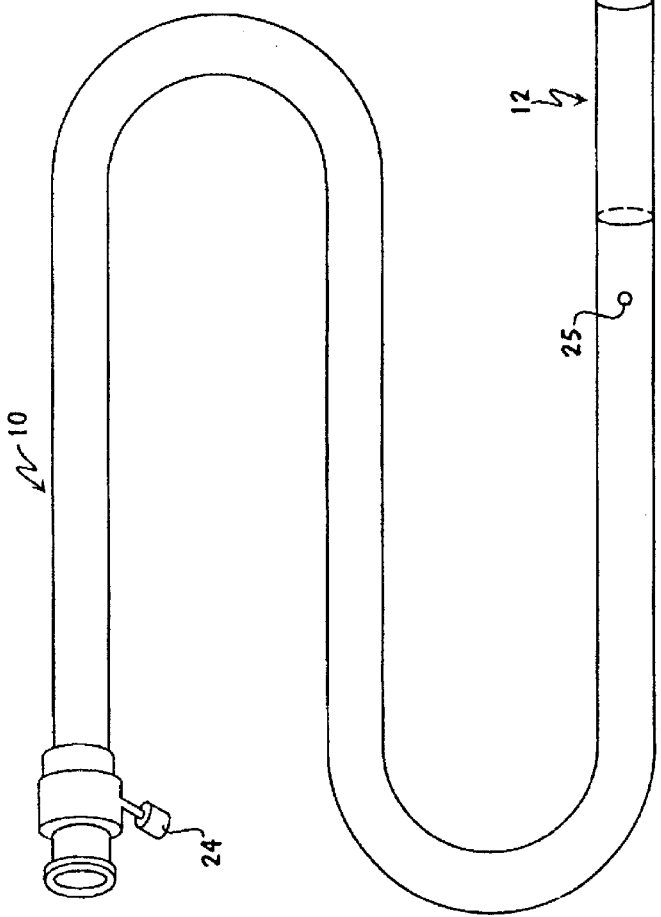
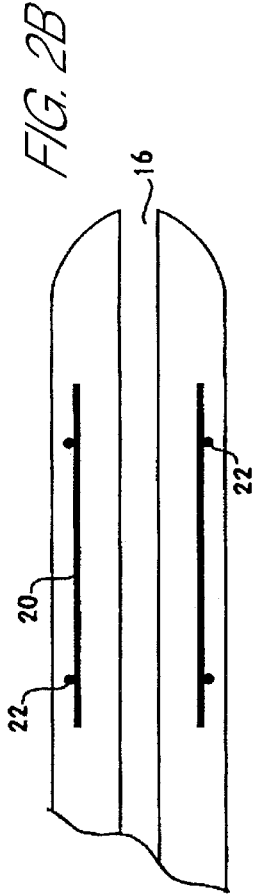
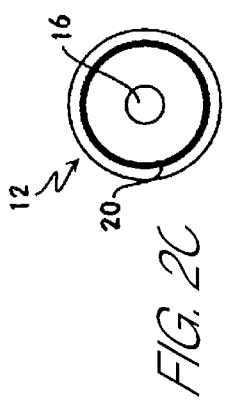
FIG. 2A
FIG. 2B
FIG. 2C

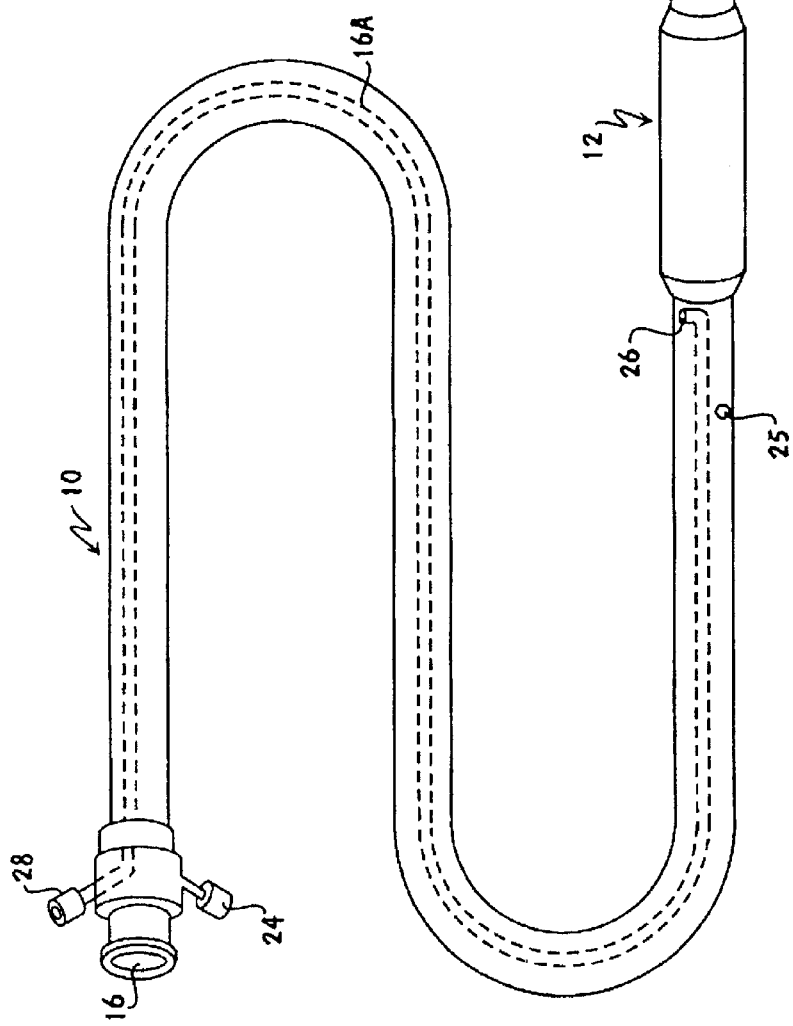
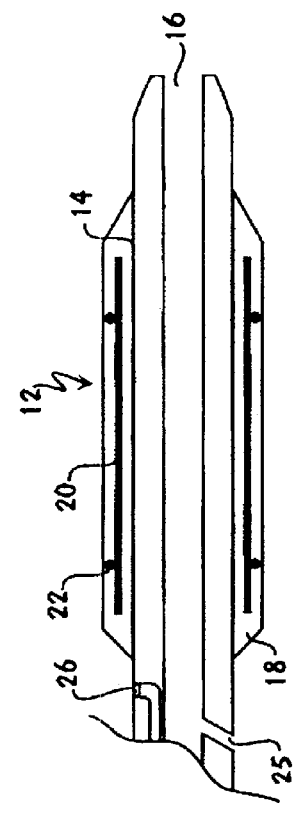

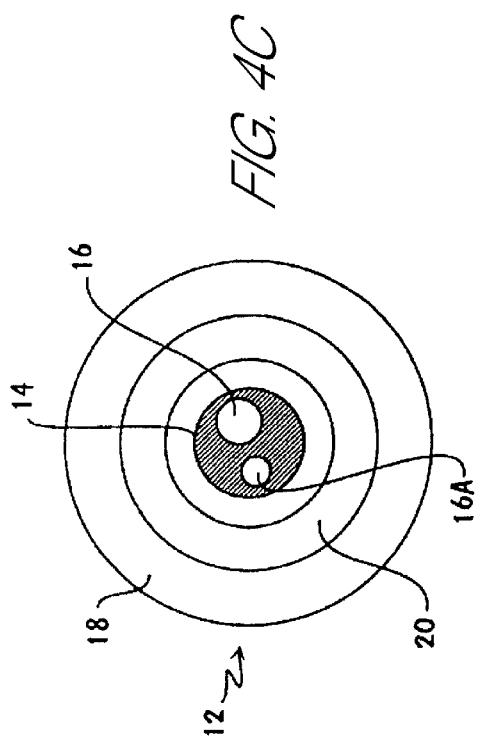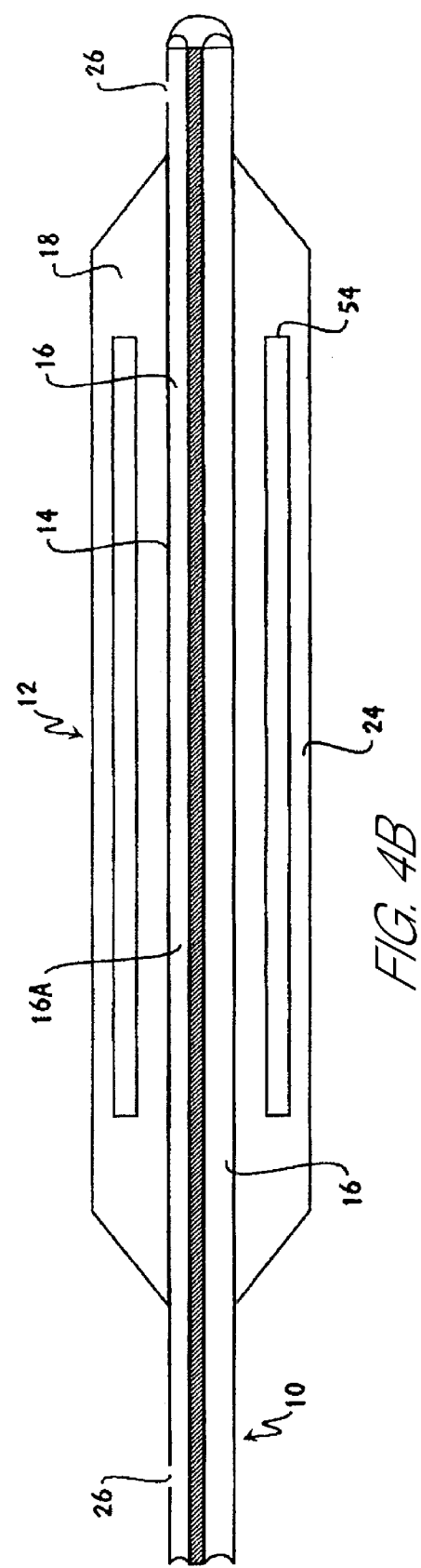

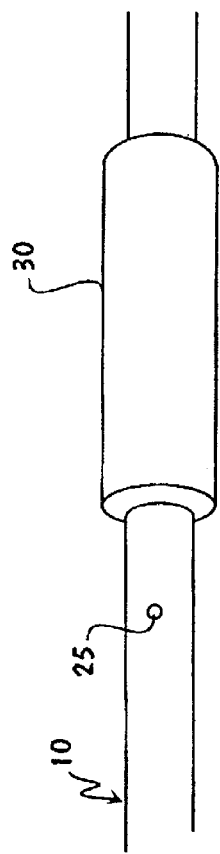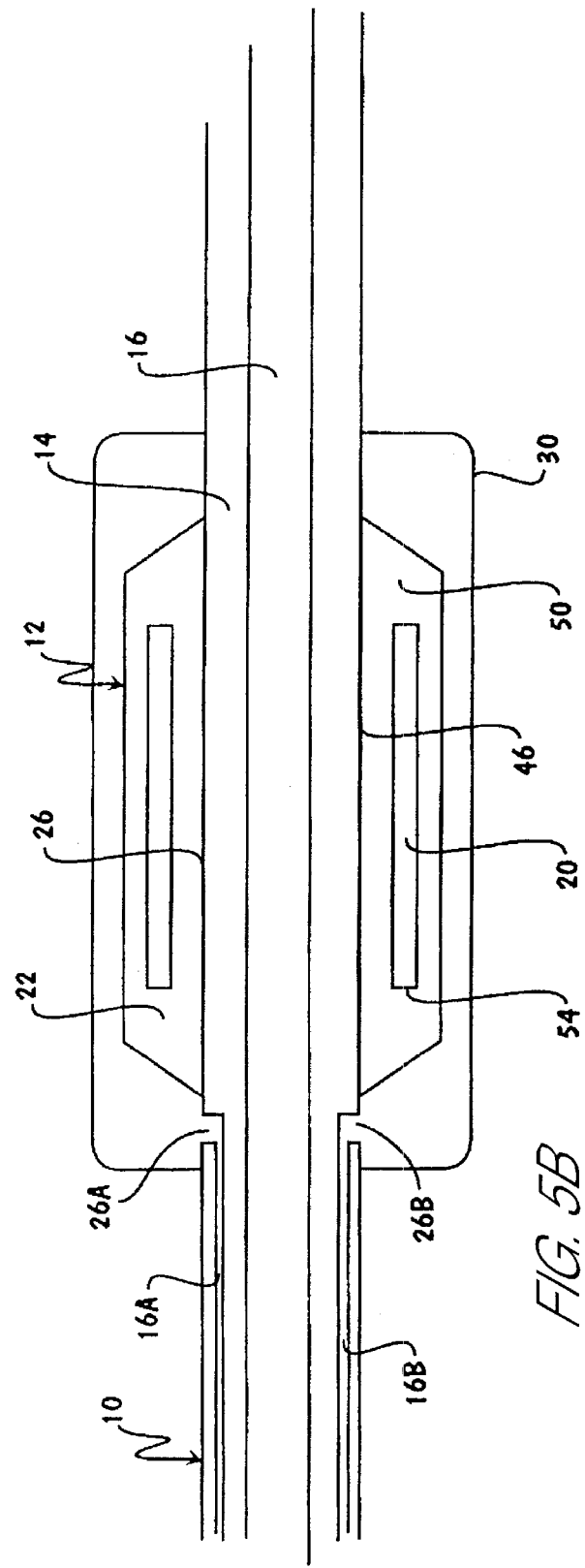

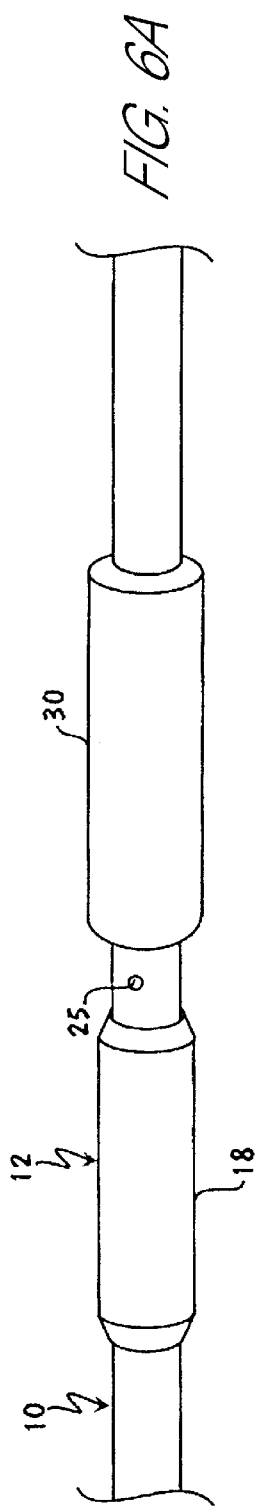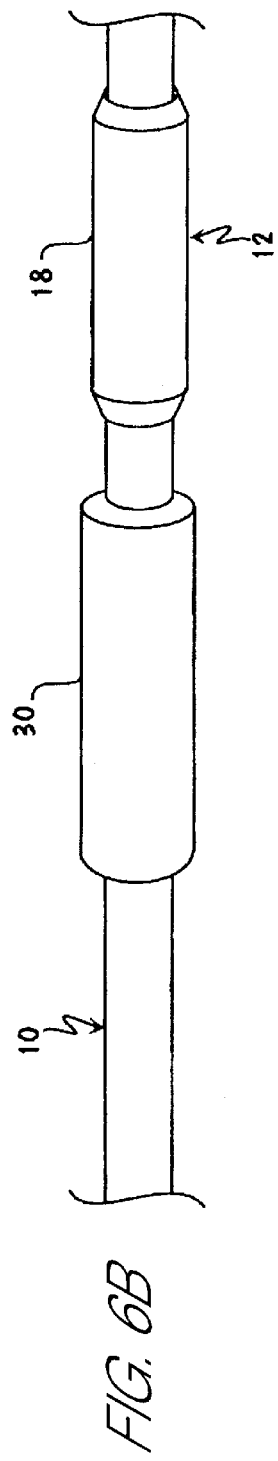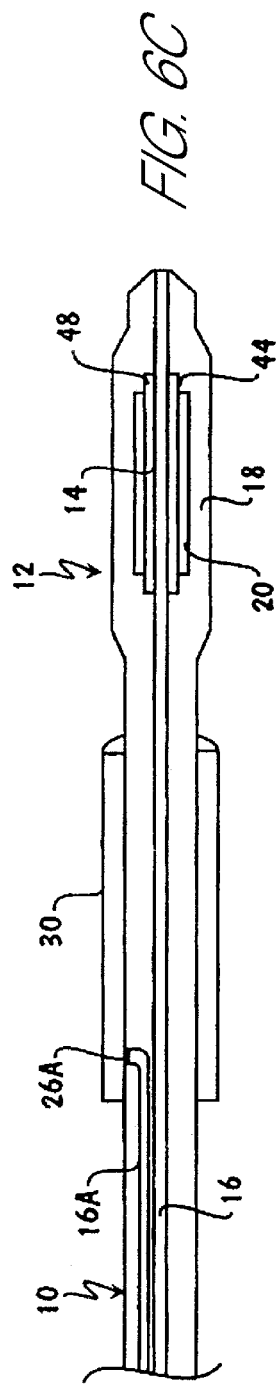

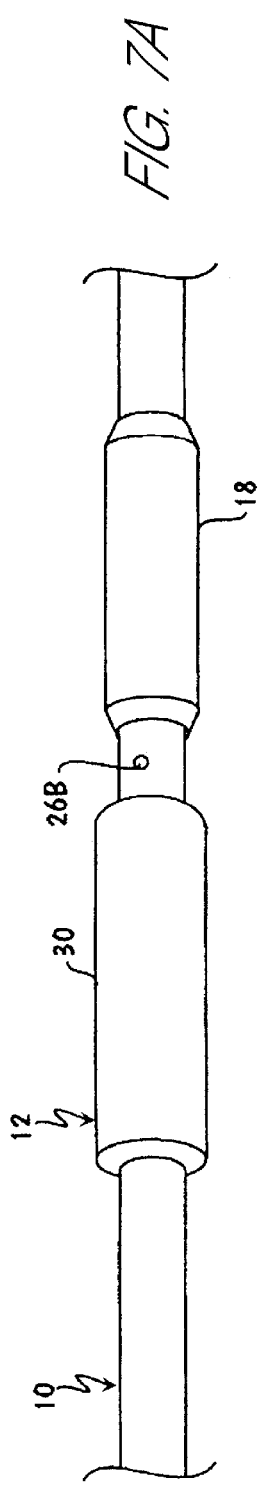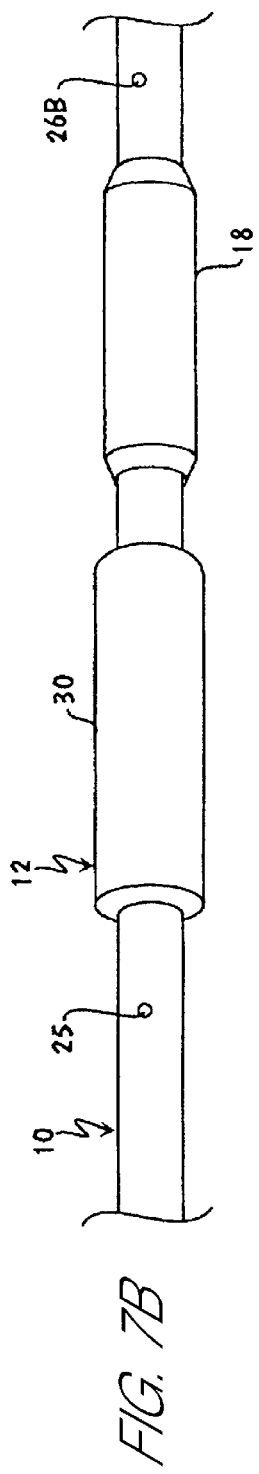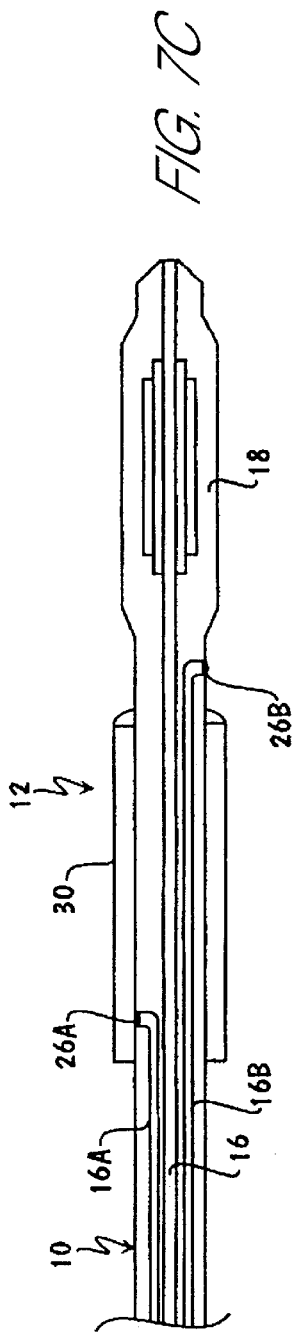

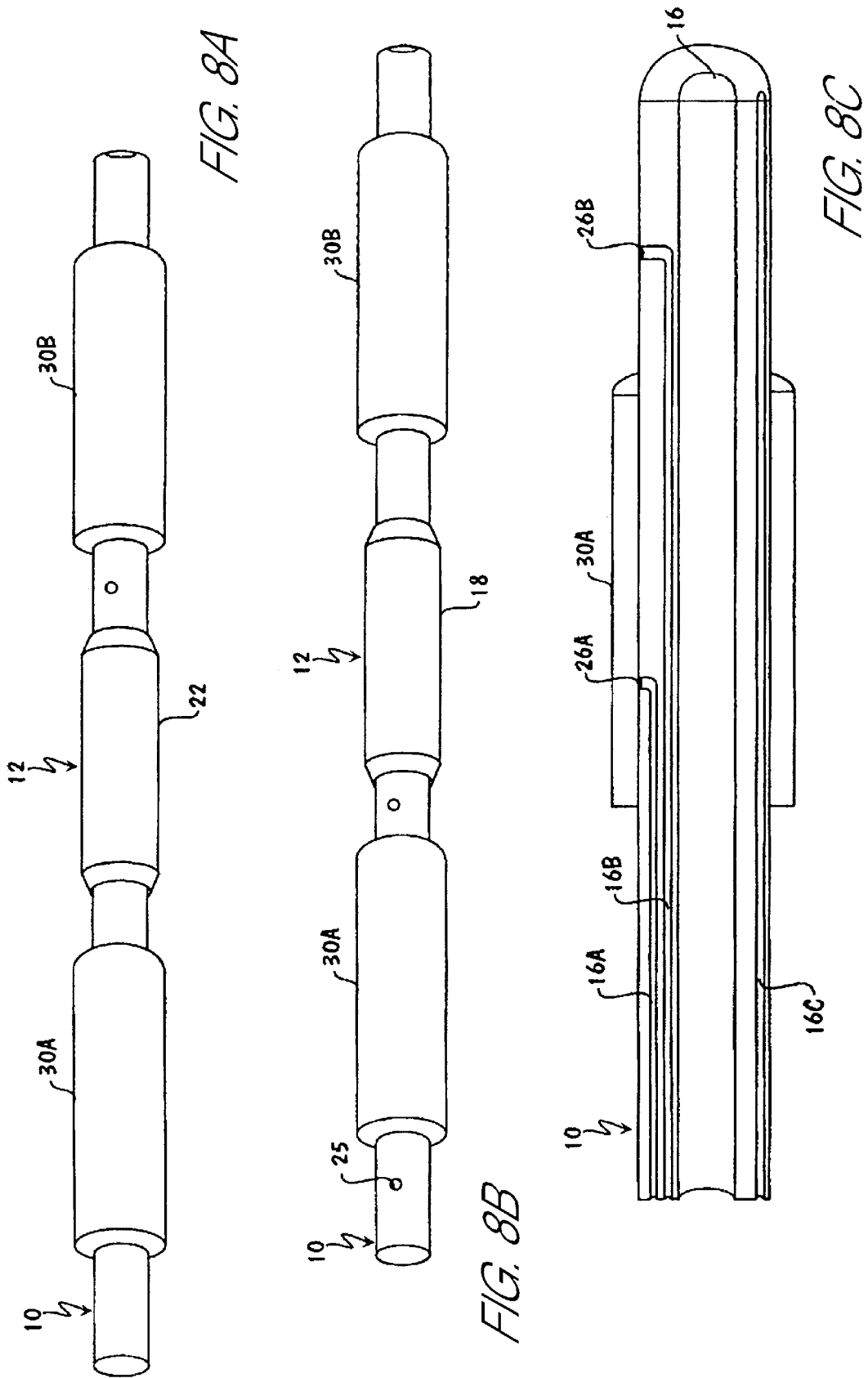

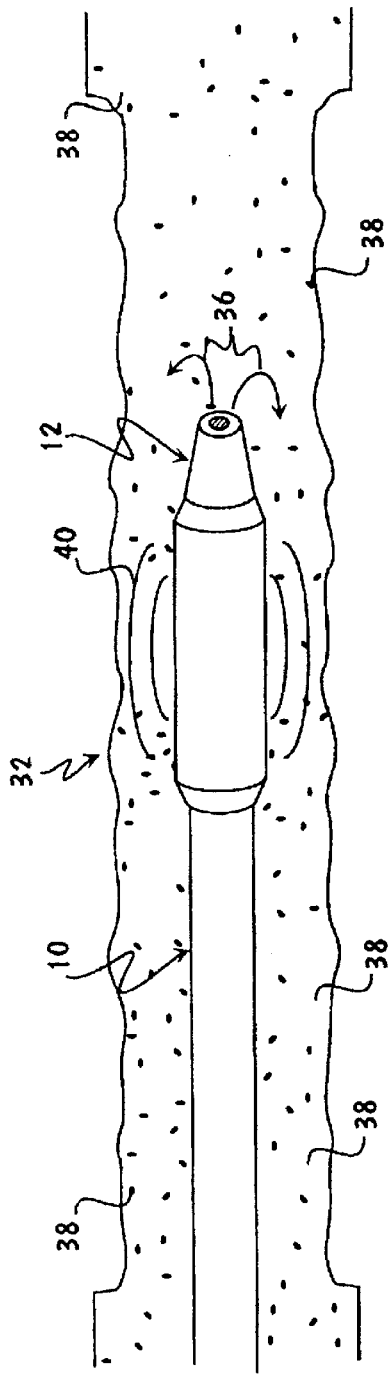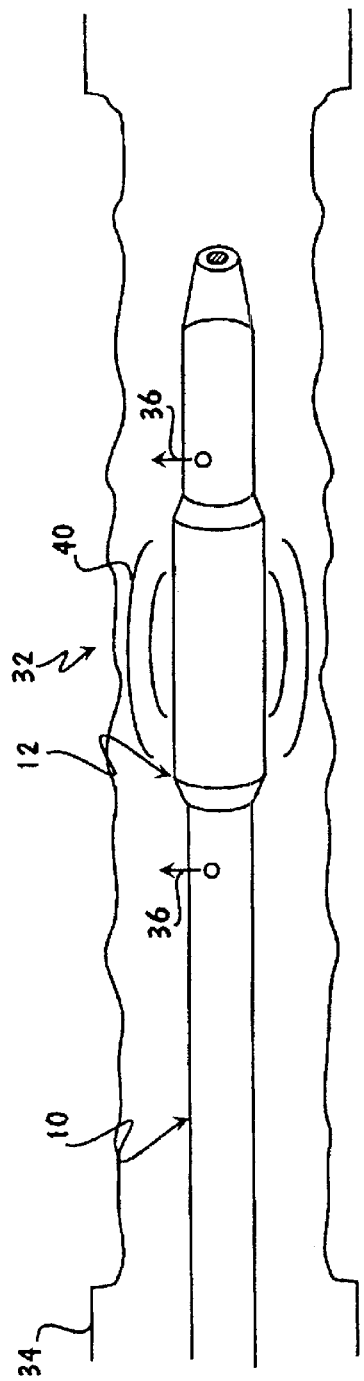
FIG. 9A
FIG. 9B

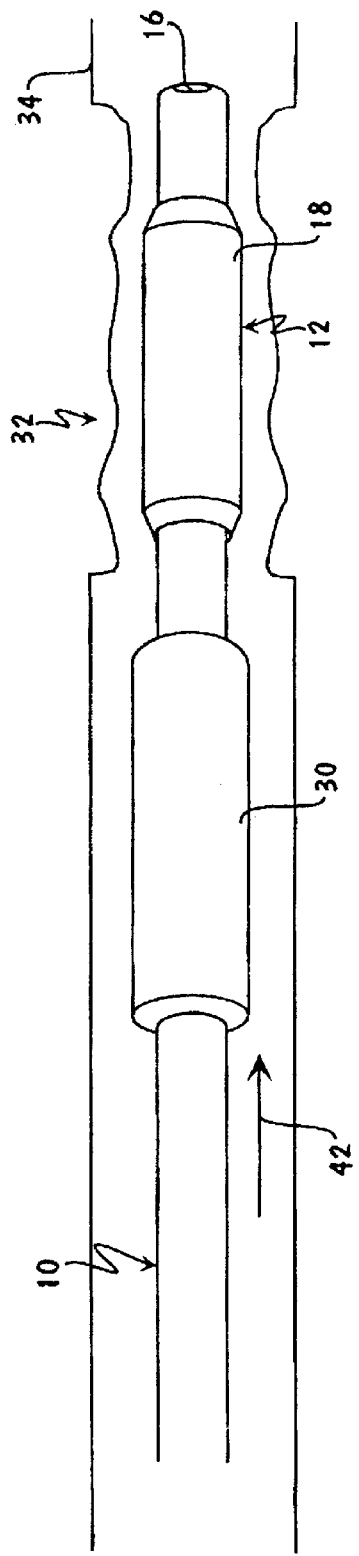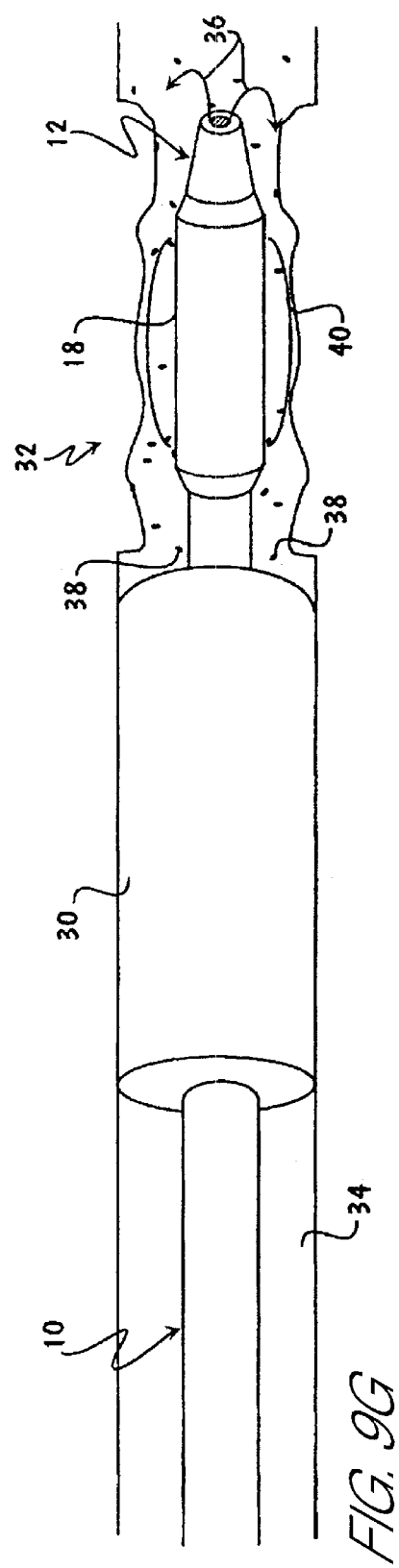
FIG. 9F
FIG. 9G

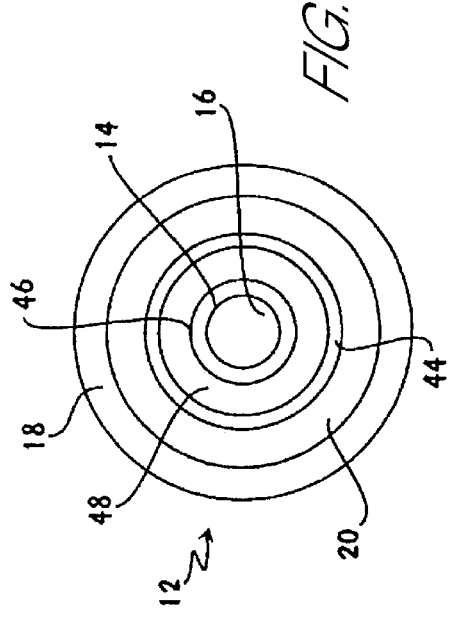
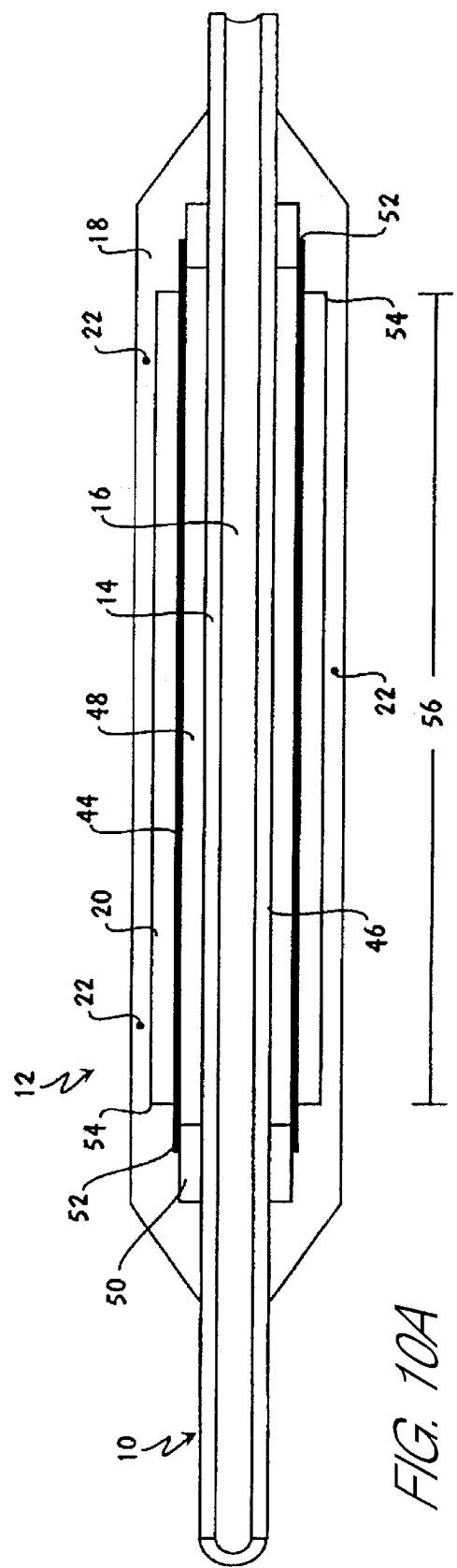
FIG. 10B
FIG. 10A

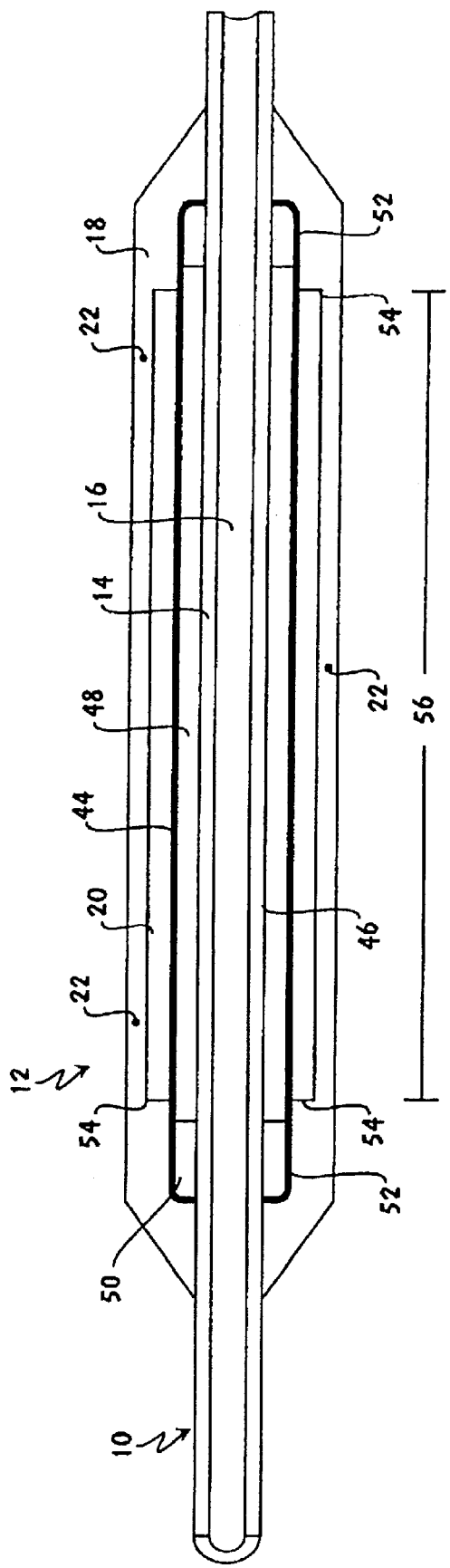

PORPHYRINA:
NATURALLY OCCURRING:

PROTOPORPHYRIA IX

SYNTHETIC:

VERDIA

CHLORINA
NATURALLY OCCURRING:

PHEOPHORBIDE

SYNTHETIC:

BPD MONO ACID RING A

FIG. 17E
SYNTHETIC:
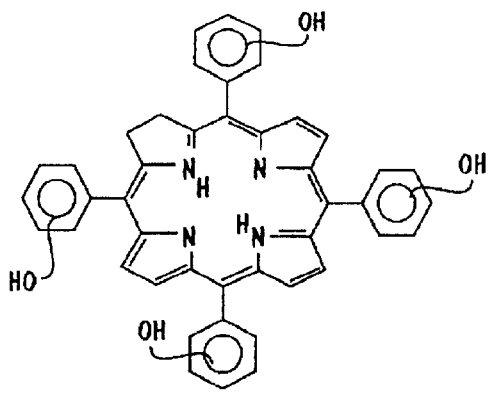
MESO-TETRA (HYDROXPHENYL) CHLORIA
FIG. 17F
SYNTHETIC:
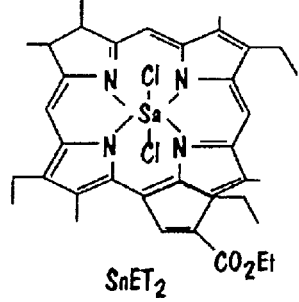
SnET₂
FIG. 17G
BACTERIACHLORINA:
NATURALLY OCCURRING:
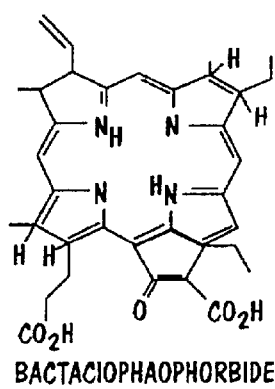
BACTACIOPHAOPHORBIDE
FIG. 17H
SYNTHETIC:
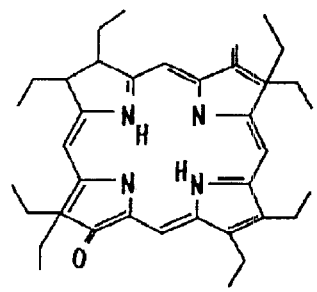
OCTAETHYLDIOXOBACTERIOCHLORIN
SYNTHETIC ISOBACTERIOCHLORIA:
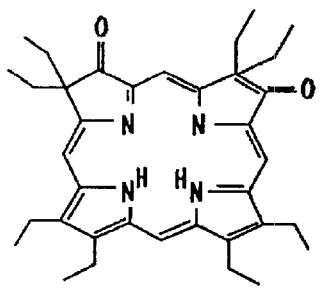
OCTAETHYLDIOXOBACTERIOCHLORIN
FIG. 17I
PHTHALOCYARINEA:
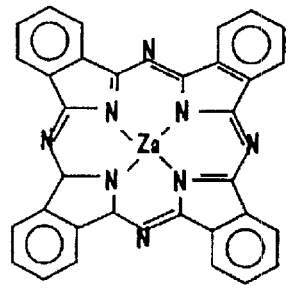
ZINC PHTHALCYANINE
FIG. 17J

NAPHTHALOCYANINE

PORPHYCENES:

SAPPHYRINS:

TEXAPHYRIAS:

FIG. 18E
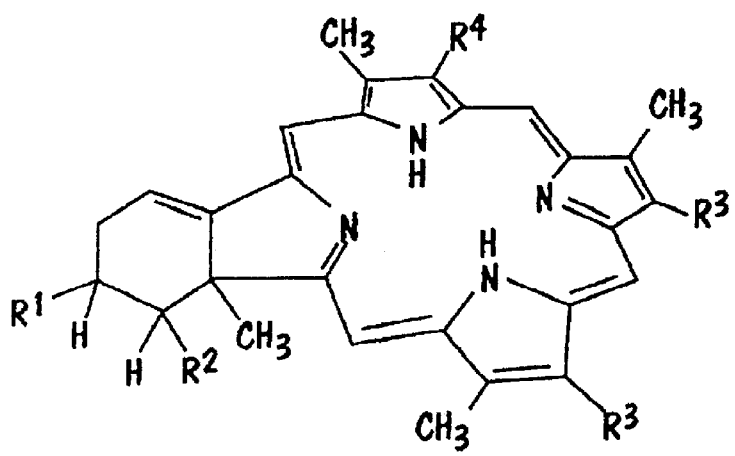
OR
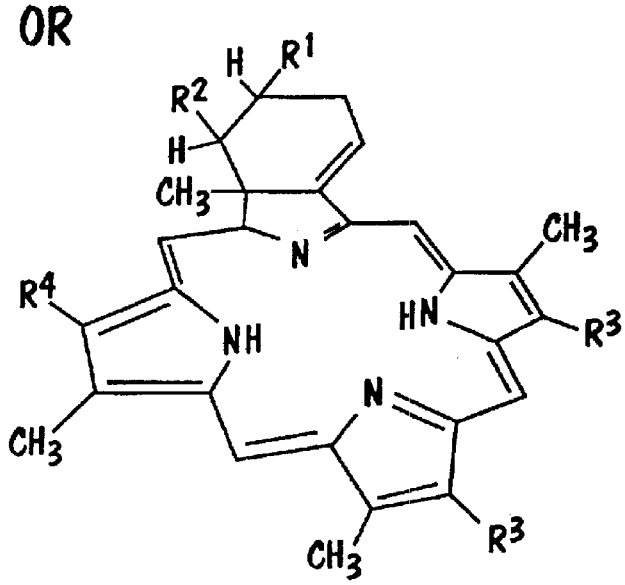
FIG. 18F

BPD - MA

AND

BPD - MB

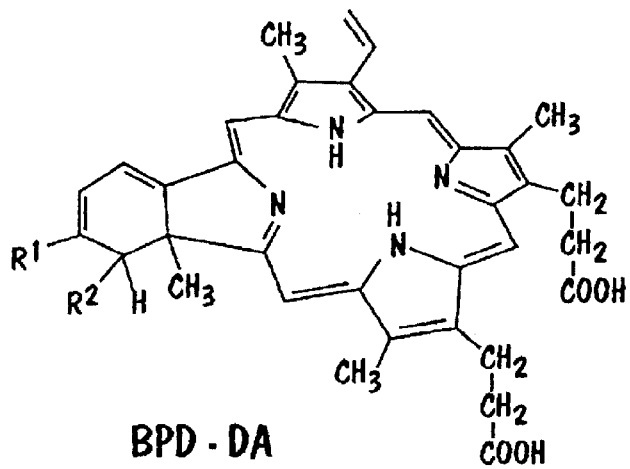
FIG. 20C
BPD - DA
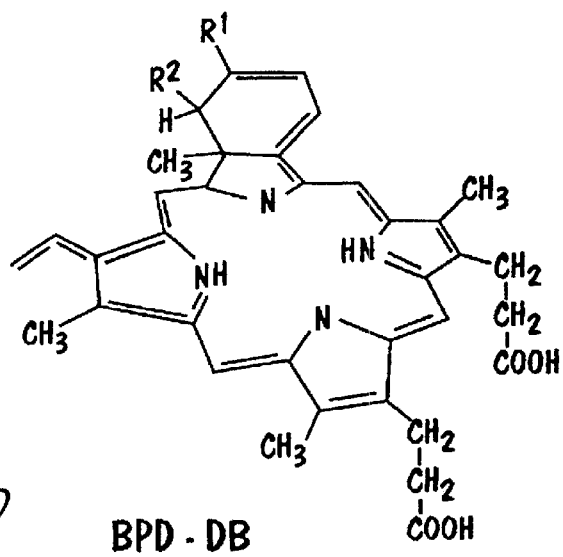
FIG. 20D   BPD - DB

HEMATOPORPHYRIN
[FORMULA A]
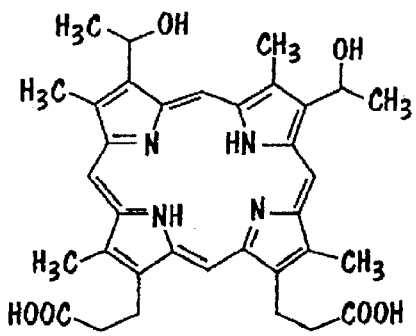
ROSE BENGAL
[FORMULA B]
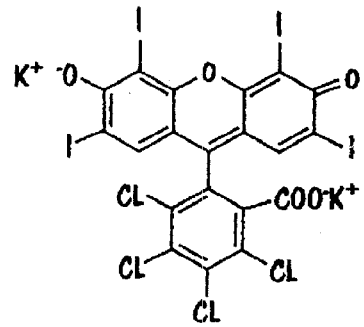
EROSIN Y
[FORMULA C]
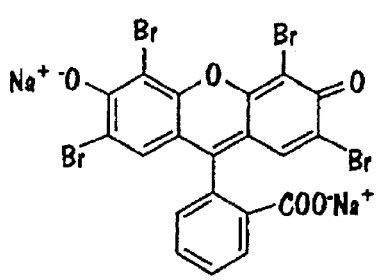
ERYTHROCIN
[FORMULA D]
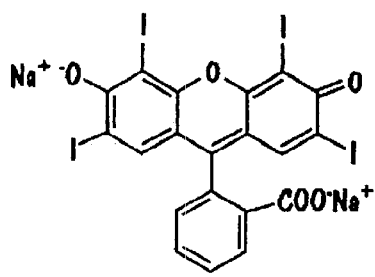
RHODAMINE B
[FORMULA E]
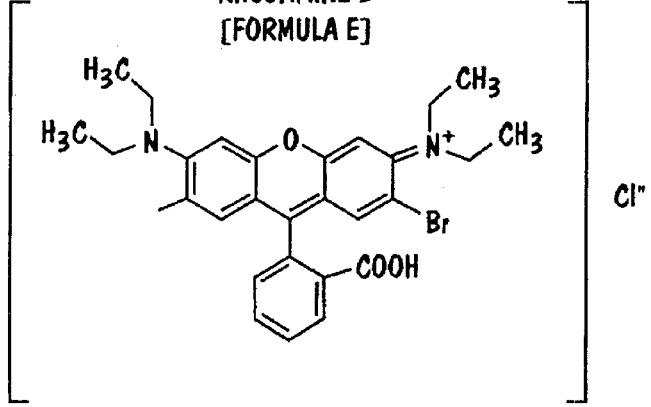
FIG. 21A

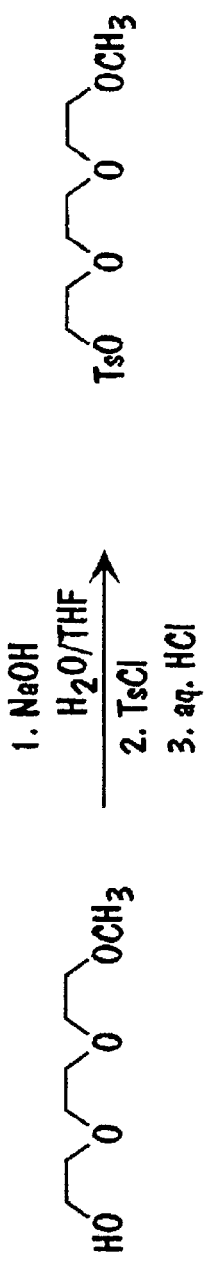
FIG. 22A
FIG. 22B
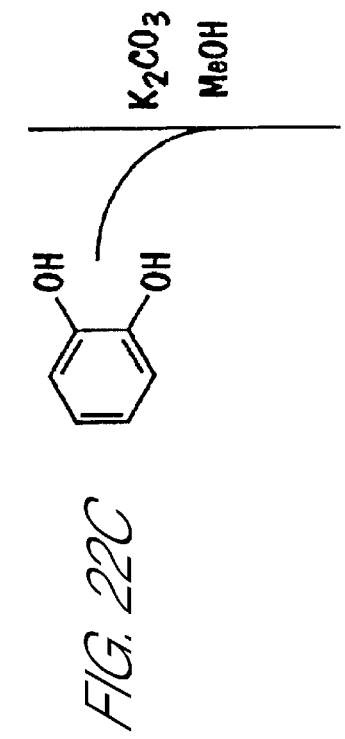
FIG. 22C
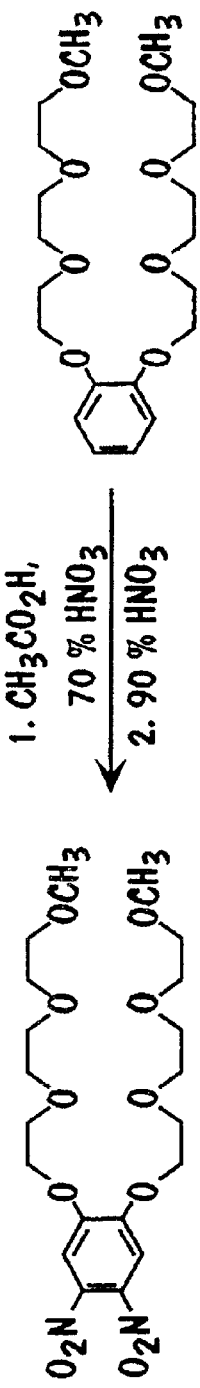
FIG. 22D
FIG. 22E

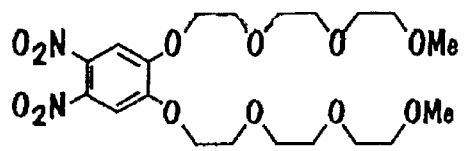
FIG. 22E (Continued)
↓ HYDRAZINE HYDRATE, 10% Pd/C, EtOH
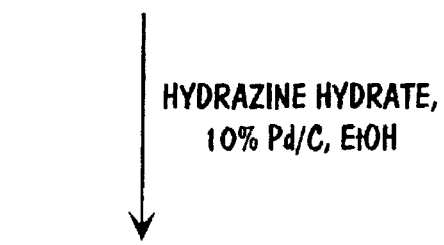 + 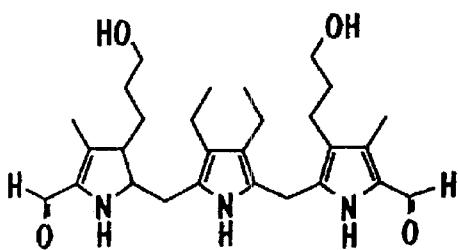
FIG. 22F
FIG. 22G
↓ 1.2 eq 12M HCl, MeOH
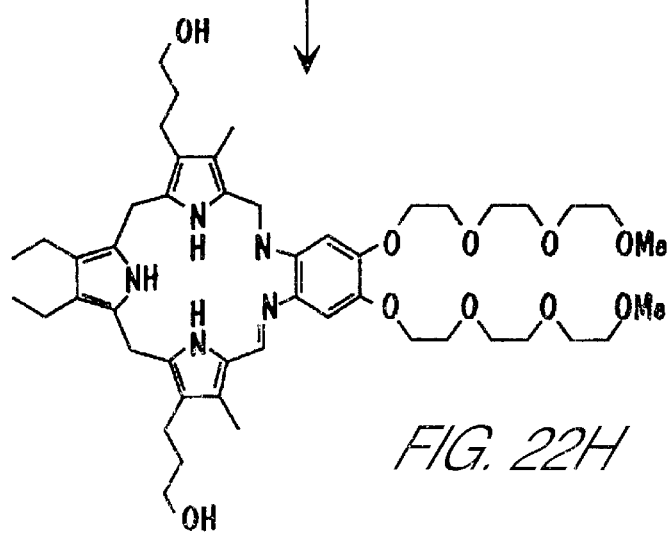
FIG. 22H

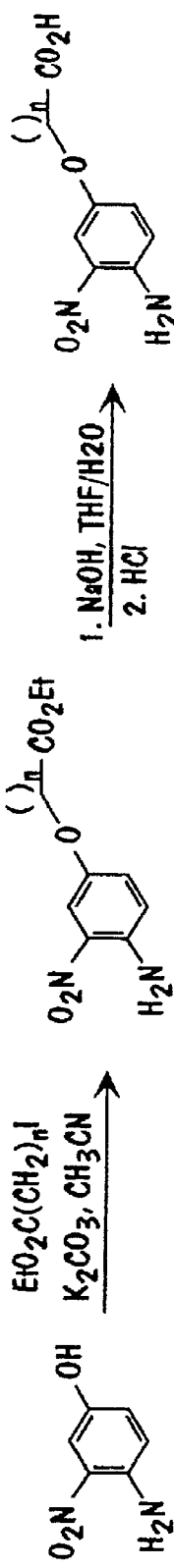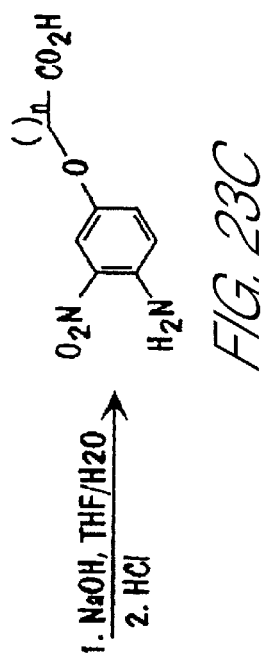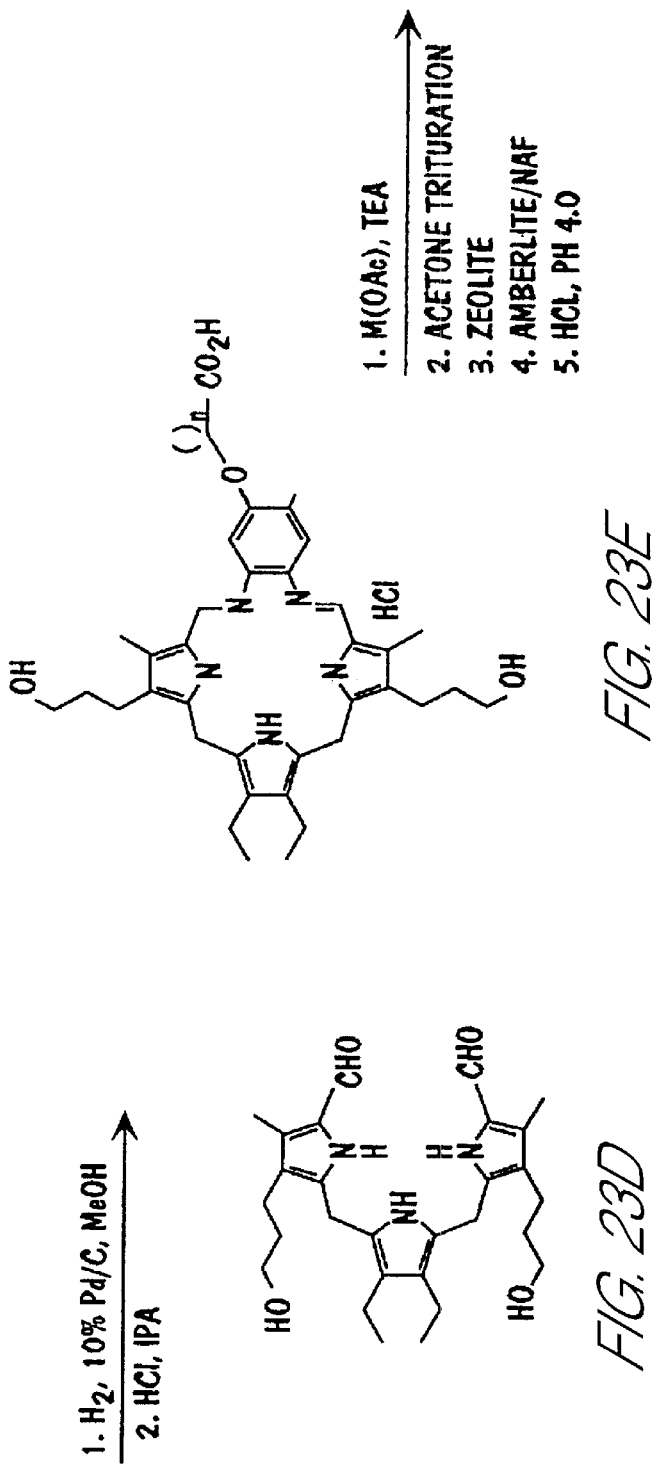
FIG. 23A
FIG. 23B
FIG. 23C
FIG. 23D
FIG. 23E

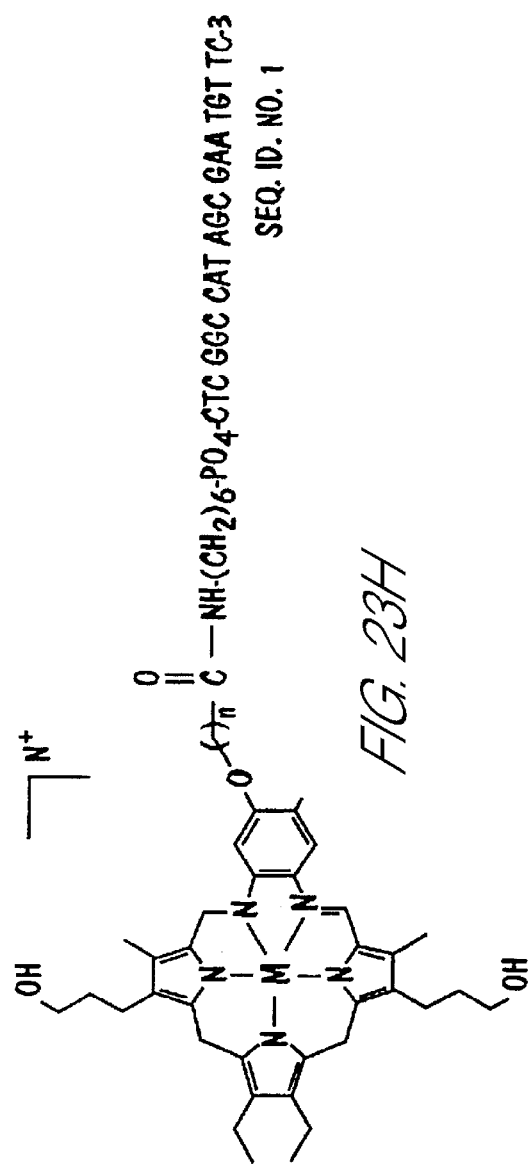
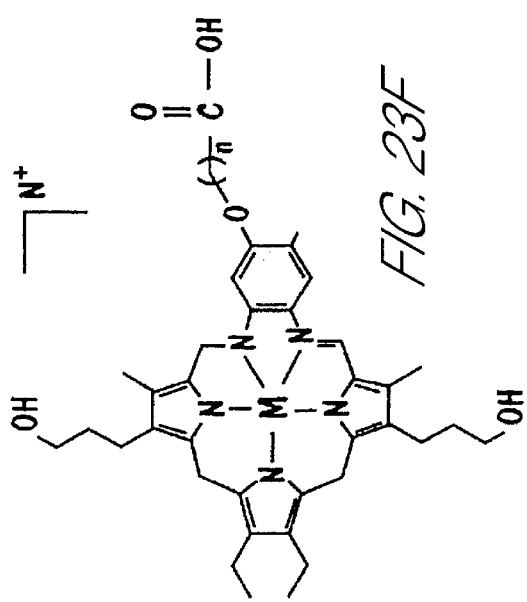
FIG. 23F
FIG. 23G
1. NHS, DCC, DMF
2. 5'-NH$_2$-(CH$_2$)$_6$-PO$_4$-CTC GGC CAT AGC GAA TGT TC-3' (0.4 M NaHCO$_3$, pH 8.6) SEQ. ID. NO. 1
FIG. 23H n = 1 - 7 n = 1 - 7

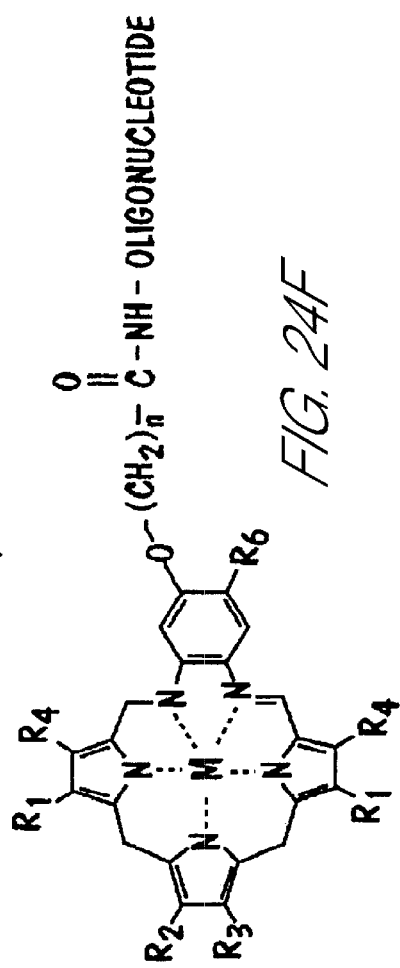
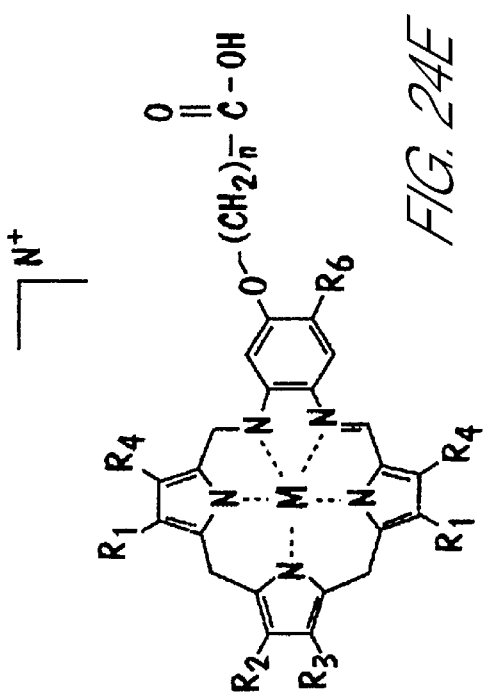
FIG. 24F
FIG. 24E
n = 1-7

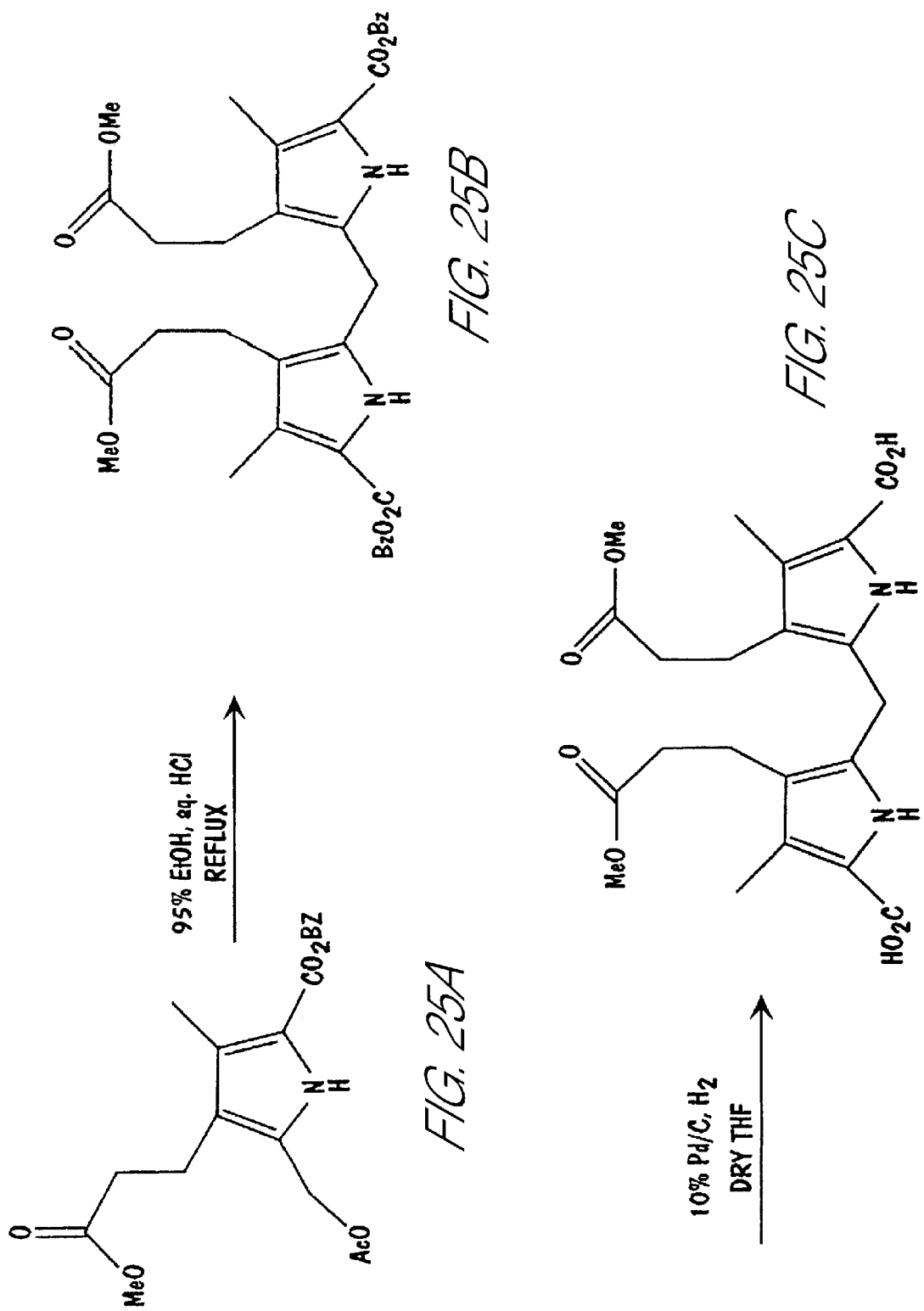

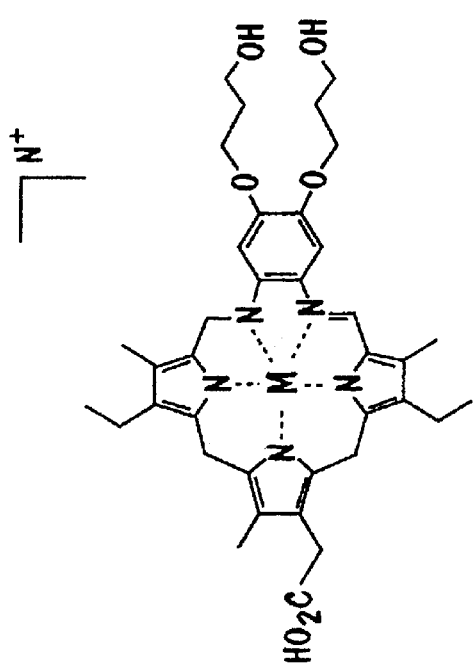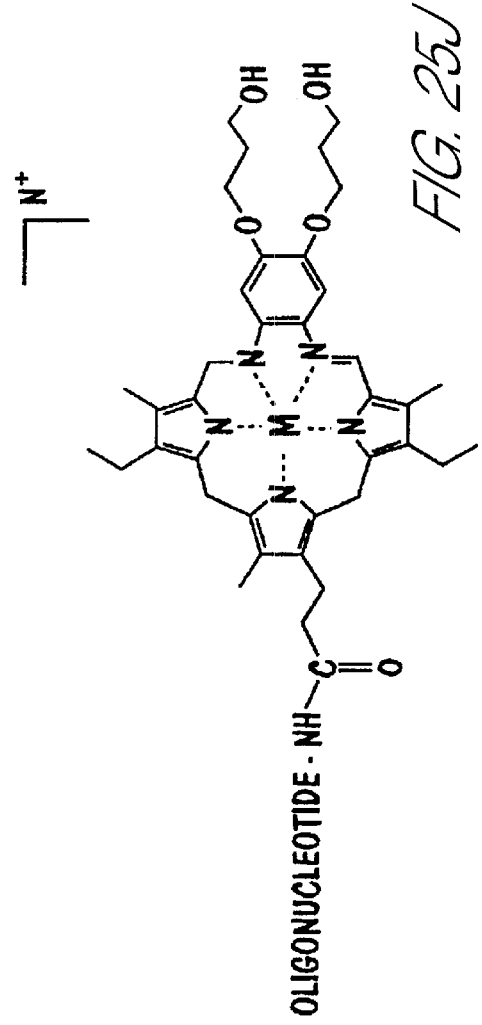
FIG. 25I
FIG. 25J
1. NHS, DCC, DMF
2. OLIGONUCLEOTIDE-NH₂ (0.4 M NaHCO₃, pH 8.6)

ULTRASOUND ASSEMBLY FOR USE WITH LIGHT ACTIVATED DRUGS

RELATED APPLICATIONS

This application is a division of U.S. patent application Ser. No. 09/158,316, entitled Ultrasound Assembly for Use With Light Activated Drugs, filed Sep. 21, 1998 now U.S. Pat. No. 6,176,842, which is a Continuation-In-Part of U.S. application Ser. No. 08/972,846; filed Nov. 18, 1997, now abandoned; entitled Ultrasound Therapy Device which is a Continuation of U.S. application Ser. No. 08/611,105; filed Mar. 5, 1996, now abandoned; entitled Ultrasound Therapy Device which claims priority to Japanese application number P07-048710; filed Mar. 8, 1995. This application is also a Continuation-In-Part of U.S. application Ser. No. 09/129,980, now U.S. Pat. No. 6,210,356; Aug. 5, 1998, and entitled Ultrasound Assembly for Use With a Catheter. This application is also a Continuation-In-Part of Japanese application number J970617JS0; filed Sep. 19, 1997; entitled Drug Carrier and Method of Using Same.

BACKGROUND OF THE INVENTION

1. Field of the Invention

The present invention relates to a method and catheter for treating biological tissues with light activated drugs, and more particularly, to a method and catheter for treating biological tissues by delivering a light activated drug to a biological tissue and exposing the light activated drug to ultrasound energy.

2. Description of Related Art

It is frequently desirable to kill targeted biological tissues such as tumors and atheroma. One technique for causing targeted tissue death is called photodynamic therapy which requires the use of light activated drugs. Light activated drugs are inactive until exposed to light of particular wavelengths, however, upon exposure to light of the appropriate wavelength activated drugs can exhibit a cytotoxic effect on the tissues where they are localized. It has been postulated that the cytotoxic effect is a result of the formation of singlet oxygen on exposure to light.

Photodynamic therapy begins with the systemic administration of a selected light activated drug to a patient. At first, the drug disperses throughout the body and is taken up by most tissues within the body. After a period of time usually between 3 and 48 hours, the drug clears from most normal tissue and is retained to a greater degree in lipid rich regions such as the liver, kidney, tumor and atheroma. A light source, such as a fiber optic, is then directed to a targeted tissue site which includes the light activated drug. The tissues of the tissue site are then exposed to light from the light source in order to activate any light activated drugs within the tissue site. The activation of the light activated drug causes tissue death within the tissue site.

Several difficulties can be encountered during photodynamic therapy. For instance, since the light activated drug is typically administered systemically, the concentration of the light activated drug within the targeted tissue site is limited by the quantity of light activated drug administered. The concentration of the light activated drug within a tissue site can also be limited by the degree of selective uptake of the light activated drug into the tissue site. Specifically, if the targeted tissue site does not selectively uptake the light activated drug, the concentration of light activated drug within the tissue site can be too low for an effective treatment.

An additional problem associated with photodynamic therapy concerns depth of treatment. Light cannot penetrate deeply into opaque tissues. As a result, the depth that light penetrates most tissue sites is limited. This limited depth can prevent photodynamic therapy from being used to treat tissues which are located deeply in the interior of a tissue site.

There is currently a need for a method and apparatus which can be used to cause death to tissues death deep within a tissue site. When the method and apparatus employ light activated drugs, the method and apparatus should be able to provide an appropriate concentration of light activated drug within the tissue site.

SUMMARY OF THE INVENTION

An object for an embodiment of the invention is causing tissue death within a tissue site.

Another object for an embodiment of the present invention is locally delivering a light activated drug to a tissue site and activating the light activated drug.

Yet another object for an embodiment of the present invention is locally delivering a light activated drug to a tissue site and delivering ultrasound energy to the delivered light activated drug to activate the light activated drug.

A further object for an embodiment of the present invention is using a catheter to locally deliver a light activated drug to a tissue site and delivering ultrasound energy from an ultrasound element on the catheter to activate the light activated drug.

Yet a further object for an embodiment of the present invention is including the light activated drug in an emulsion, locally delivering the emulsion to a tissue site and delivering ultrasound energy to the light activated drug within the tissue site to activate the light activated drug.

Even a further object for an embodiment of the present invention is including the light activated drug in a liposome, locally delivering the liposome to a tissue site and delivering ultrasound energy to the light activated drug within the tissue site to activate the light activated drug.

An additional object for an embodiment of the present invention is including the light activated drug in an aqueous solution, locally delivering the aqueous solution to a tissue site and delivering ultrasound energy to the light activated drug within the tissue site to activate the light activated drug.

Yet a further object for an embodiment of the present invention is including the light activated drug in an emulsion, systemically delivering the emulsion, providing the light activated drug sufficient time to localize within a tissue site and delivering ultrasound energy to the light activated drug within the tissue site to activate the light activated drug.

Even a further object for an embodiment of the present invention is including the light activated drug in liposomes, systemically delivering the liposomes, providing the light activated drug sufficient time to localize within a tissue site and delivering ultrasound energy to the light activated drug within the tissue site to activate the light activated drug.

An additional object for an embodiment of the present invention is including the light activated drug in an aqueous solution, systemically delivering the aqueous solution, providing the light activated drug sufficient time to localize within a tissue site and delivering ultrasound energy to the light activated drug within the tissue site to activate the light activated drug.

Another object for an embodiment of the present invention is coupling a site directing molecule to a light activated drug, locally delivering the light activated drug to a tissue site and activating the light activated drug within the tissue site.

Yet another object for an embodiment of the invention is providing a catheter for locally delivering a media including a light activated drug to a tissue site. The catheter including an ultrasound assembly configured to activate the light activated drug within the tissue site.

A further object for an embodiment of the invention is providing a catheter for delivering a media including a light activated drug to a tissue site. The catheter including an ultrasound assembly for reducing exposure of the light activated drug to ultrasound energy until the light activated drug has been delivered from within the catheter.

A kit for causing tissue death within a tissue site is disclosed. The kit includes a media with a light activated drug activatable upon exposure to a particular level of ultrasound energy. The kit also includes a catheter with a lumen coupled with a media delivery port through which the light activated drug can be locally delivered to the tissue site. The ultrasound transducer is configured to transmit the level of ultrasound energy which activates the light activated drug with sufficient power that the ultrasound energy can penetrate the tissue site.

A method for causing tissue death in a subdermal tissue site is also disclosed. The method includes providing a catheter for locally delivering a light activated drug to the subdermal tissue site, the catheter including an ultrasound transducer. The method also includes locally delivering the light activated drug to the tissue site; producing ultrasound energy from the ultrasound transducer, and directing the ultrasound energy to the subdermal tissue site following penetration of the light activated drug into the subdermal tissue site to activate least a portion of the light activated drug within the subdermal tissue site.

A method for activating a light activated drug is also disclosed. The method includes providing a catheter with an ultrasound transducer. The method also includes introducing the light activated drug into a patient's body where a subdermal tissue site absorbs at least a portion of the light activated drug; producing ultrasound energy; directing the ultrasound energy to the light activated containing subdermal tissue site including the light activated drug; and activating at least a portion of the light activated drug in the subdermal selected tissue site.

A method for releasing a therapeutic from a microbubble is also disclosed. The method includes providing a microbubble with a light activated drug activatable upon exposure to ultrasound energy; and delivering ultrasound energy to the microbubble at a frequency and intensity which activates the light activated drug to cause a rupture of the microbubble.

A microbubble is also disclosed. The microbubble includes a substrate defining a shell of the microbubble and having a thickness permitting hydraulic transport of the microbubble. The microbubble also includes a light activated drug activatable upon exposure to ultrasound energy. Activation of the light activated drug causes a disruption in the shell sufficient to cause a rupture of the microbubble. The microbubble further includes a therapeutic releasable from the microbubble upon rupture of the microbubble and yielding a therapeutic effect upon release from the microbubble.

BRIEF DESCRIPTION OF THE FIGURES

FIG. 1A is a side view of a catheter for locally delivering a media including a light activated drug to a tissue site.

FIG. 1B is an axial cross section of an ultrasound assembly for use with the catheter shown in FIG. 1A.

FIG. 1C is a lateral cross section of an ultrasound assembly for use with the catheter shown in FIG. 1A.

FIG. 2A is a side view of a catheter having an elongated body and an ultrasound assembly which is flush with the elongated body.

FIG. 2B is an axial cross section of the ultrasound assembly illustrated in FIG. 2A.

FIG. 2C is a lateral cross section of the ultrasound assembly illustrated in FIG. 2A.

FIG. 3A illustrates a catheter with a utility lumen and a second utility lumen.

FIG. 3B is an axial cross section of the ultrasound assembly illustrated in the catheter of FIG. 3A.

FIG. 4B is a cross section of an ultrasound assembly included on a catheter with a plurality of utility lumens.

FIG. 4C is a cross section of an ultrasound assembly included on a catheter with a plurality of utility lumens.

FIG. 5A is a side view of a catheter including a balloon.

FIG. 5B is a cross section of a catheter with a balloon which include an ultrasound assembly.

FIG. 6A is a side view of a catheter with a balloon positioned distally relative to an ultrasound assembly.

FIG. 6B is a side view of a catheter with an ultrasound assembly positioned distally relative to a balloon.

FIG. 6C is a cross section of a catheter with an ultrasound assembly positioned at the distal end of the catheter.

FIG. 7A is a side view of a catheter with a media delivery port positioned between an ultrasound assembly and a balloon.

FIG. 7B is a side view of a catheter with an ultrasound assembly positioned between a media delivery port and a balloon.

FIG. 7C is a cross section of a catheter with an ultrasound assembly positioned at the distal end of the catheter.

FIG. 8A is a side view of a catheter including a media delivery port and an ultrasound assembly positioned between first and second balloons.

FIG. 8B is a side view of a catheter including a media delivery port and an ultrasound assembly positioned between first and second balloons.

FIG. 8C is a cross section of a balloon included on a catheter having a first and second balloon.

FIG. 9A illustrates an ultrasound assembly positioned adjacent to a tissue site and microbubbles delivered via a utility lumen.

FIG. 9B illustrates an ultrasound assembly positioned adjacent to a tissue site and a media delivered via a media delivery port.

FIG. 9F illustrates a catheter with an ultrasound assembly outside a balloon positioned at a tissue site.

FIG. 9G illustrates the balloon of FIG. 9F expanded into contact with a vessel so as to occlude the vessel.

FIG. 10A is a cross section of an ultrasound assembly according to the present invention.

FIG. 10B is a cross section of an ultrasound assembly according to the present invention.

FIG. 10C illustrates a support member with integral supports.

FIGS. 18A–F illustrate the formula of preferred light emitting drugs for use with media including microbubbles.

FIGS. 20A–D illustrate the formula of four preferred forms of the hydromonobenzoporphyrin derivatives of the green porphyrins illustrated in formulae 3 and 4 of FIG. 18.

FIGS. 21A–B illustrate the formulae for specific examples of pyrrole-based macrocycle derivatives and xanthene derivatives which are preferred for inclusion in microbubbles to enhance rupture of the microbubbles upon activation.

FIGS. 22A–I schematically summarize the synthesis of an oligonucleotide conjugate of a texaphyrin metal complex.

FIGS. 23A–H illustrate the covalent coupling of texaphyrin metal complexes with amine, thiol, or hydroxy linked oligonucleotides.

FIGS. 24A–F illustrate the synthesis of diformyl monoic acid and oligonucleotide conjugate.

FIGS. 25A–J illustrate the synthesis of a texaphyrin based light activated drug.

DETAILED DESCRIPTION

Figure 4A:
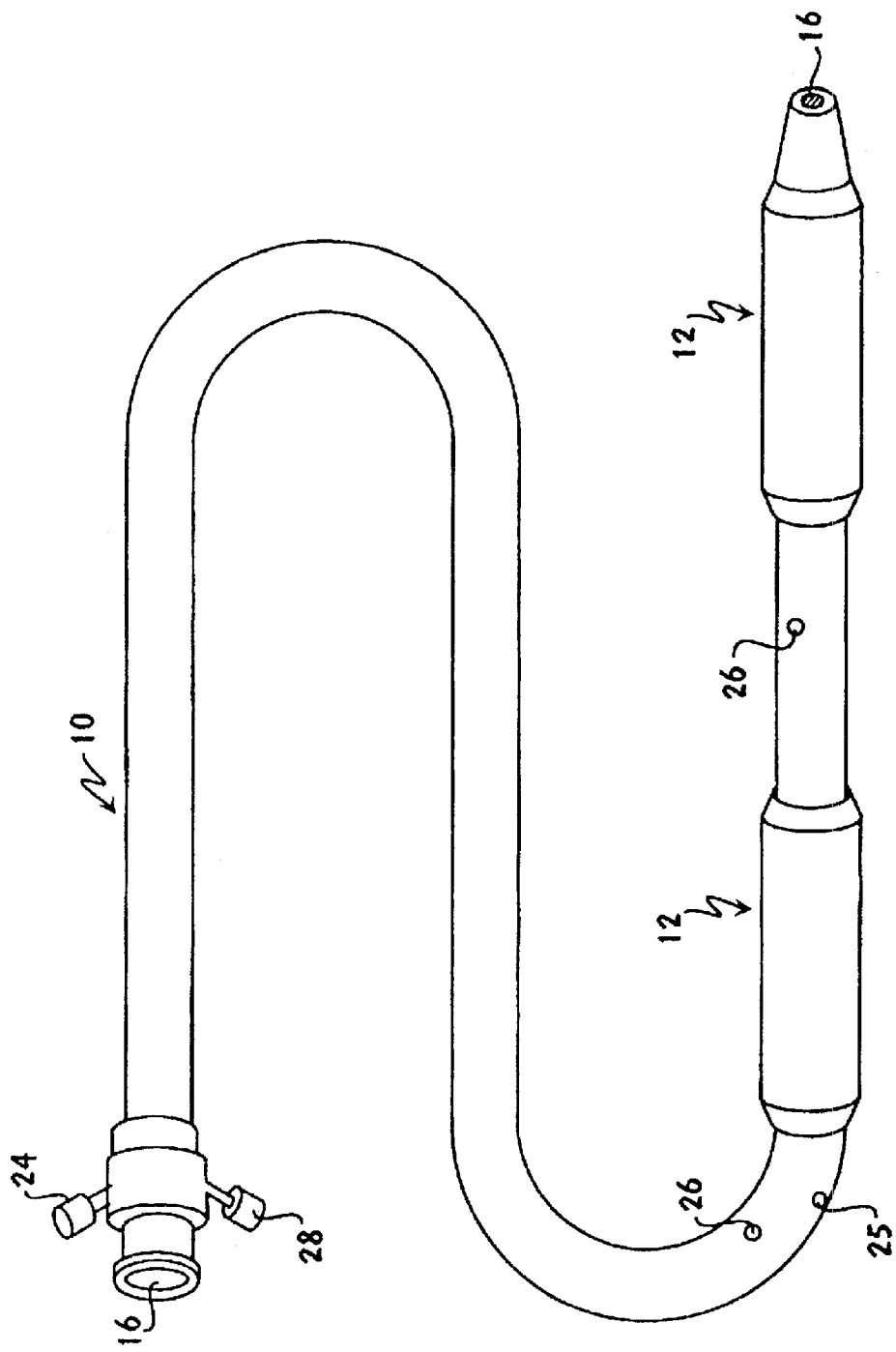
FIG. 4A is a side view of a catheter including a plurality of ultrasound assemblies.

The present invention relates to a method and catheter for delivering a light activated drug to a tissue site and delivering ultrasound energy to the light activated drug within the tissue site. Since many light activated drugs are also activated by ultrasound energy, the delivery of ultrasound energy to the light activated drug activates the light activated drug within the tissue site. Similar to activation of a light activated drug by light, activation by ultrasound causes death of tissues within the tissue site. The tissue death is believed to result from the release of a singlet oxygen. Suitable tissue sites include, but are not limited to, atheroma, cancerous tumors, thrombi and potential restenosis sites. A potential restenosis site is a tissue site where restenosis is likely to occur such as the portion of vessels previously treated by balloon angioplasty. In contrast to light, ultrasound energy can be transmitted through opaque tissues. As a result, the ultrasound energy can be used to treat tissues which are deeper within a tissue site than could be treated via light activation.

One explanation for the activation of light activated drugs via the application of ultrasound is a result of cavitation. Cavitation is known to occur when ultrasonic energy above a certain threshold is applied to a liquid. The mechanism of generation of cavitation is described in Apfel, Robert E., "Sonic Effervescence: Tutorial on Acoustic Cavitation" Journal of Acoustic Society of America 101 (3): 1227–1237 (March 1997) and Atchley A., Crum L., "Ultrasound—Its Chemical, Physical and Biological Effects: Acoustic Cavitation and Bubble Dynamics," pp. 1–64, 1988 VCH Publishers, New York (1998).

Cavitation results when gas dissolved in a solution forms bubbles under certain types of acoustic vibration. Cavitation can also occur when small bubbles already present in the solution oscillate or repeatedly enlarge and contract to become bubbles. When the size of these cavitation bubbles reaches a size that cannot be maintained, they suddenly collapse and release various types of energy. The various types of energy include, but are not limited to, mechanical energy, visible light, ultraviolet light and other types of electromagnetic radiation. Heat, plasma, magnetic fields, shock waves, free radicals, heat and other forms of energy are also thought to be generated locally. The light activated drug is believed to be activated by at least one of the various forms of energy generated at the time of cavitation collapse.

The delivery of light activated drug to the tissue site can be through traditional systemic administration of a media including the light activated drug or can be performed through localized delivery of the media. Localized delivery can be achieved through injection into the tissue site or through other traditional localized delivery techniques. A preferred delivery technique is using a catheter which includes a media delivery lumen coupled with a media delivery port. The catheter can be positioned such that the media delivery port is within the tissue site or is adjacent to the tissue site via traditional over-the-guidewire techniques. The media can then be locally delivered to the tissue site through the media delivery port.

The localized delivery of the light activated drug to the tissue sight serves to localize the light activated drug within the tissue site and can reduce the amount of light activated drug which concentrates in tissues outside the tissue site. Further, localized delivery of the light activated drug can serve to increase the concentration of the light activated drug within the tissue site above levels which would be achieved through systemic delivery of the light activated drug. Alternatively, the same concentration of light activated drug within the tissue site as would occur through systemic administration can be achieved by introducing smaller amounts of light activated drug into a patient's body.

Localized delivery of the light activated drug also permits treatment of tissue sites which do not have selective uptake of the light activated drug. As discussed above, many light activated drugs, such as the texaphyrins, are taken up by most tissues within the body and later localize within lipid rich tissues. As a result, a non-lipid rich tissue site can be treated by delivering the ultrasound energy to the tissue site before the light activated drug has an opportunity to localize in lipid rich tissues.

Localized delivery is also advantageous when the tissue site is lipid rich such as in an atheroma or a tumor. The localized delivery of the light activated drug combined with the inherent affinity of the light activated drug for tissue site can result in a high degree of localization of the light activated drug within lipid rich tissue sites.

To increase localization of the light activated drug within the tissue site, the light activated drug can be coupled with a sight directing molecule to form a light activated drug conjugate. The site directing molecule is chosen so the light activated drug conjugate specifically binds with the tissue site when the light activated drug conjugate is contacted with the tissue site under physiological conditions of temperature and pH. The specific binding may result from specific electrostatic, hydrophobic, entropic, or other interactions between certain residues on the conjugate and specific residues on the tissue site.

In one preferred embodiment, the light activated drug includes an oligonucleotide acting as a site specific molecule coupled with a texaphyrin. The oligonucleotide can have an affinity for a targeted site on a DNA strand. For instance, the oligonucleotide can be designed to have complementary Watson-Crick base pairing with the targeted DNA site. Activation of the light activated drug after the conjugate has bound the targeted DNA site can cause cleavage of the DNA strand at the targeted DNA site. As a result, the activated conjugate can be used for cleavage of targeted DNA sites. The light activated conjugate can be targeted to a site on viral DNA where activation of the light activated conjugate causes the virus to be killed. Similarly, the light activated conjugate can be targeted to oncogenes. Other applications of targeted DNA cleavage include, but are not limited to, antisense applications, specific cleavage and subsequent recombination of DNA; destruction of viral DNA; construction of probes for controlling gene expression at the cellular level and for diagnosis; and cleavage of DNA in footprinting analyses, DNA sequencing, chromosome analysis, gene isolation, recombinant DNA manipulations, mapping of large genomes and chromosomes, in chemotherapy and in site directing mutagenesis.

In another preferred embodiment, the light activated drug includes a hormone. The hormone may be targeted to a particular biological receptor which is localized at the tissue site.

The light activated drug can be included within several media suitable for delivery into the body. Many light activated drugs are known to have low water solubilities of less than 100 mg/L. As a result, achieving the desired concentration of light activated drug in an aqueous solution media for systemic delivery can often be difficult. However, localized delivery of the light activated drug requires a lower concentration of light activated drug within the media. As a result, when the light activated drug is delivered locally, the light activated drug can be included in an aqueous solution.

The media can also be an emulsion which includes a lipoid as a hydrophobic phase dispersed in a hydrophilic phase. These emulsions provide a media which is safe for delivery into the body with an effective concentration of light activated drug.

The media can also include microbubbles comprised from a substrate which forms a shell. Suitable substrates for the microbubble include, but are not limited to, biocompatible polymers, albumins, lipids, sugars or other substances. The light activated drug can be enclosed within the microbubble, coupled with the shell and/or distributed in the media outside the microbubble. A preferred microbubble comprises a lipid substrate such as liposome. Systemic administration of liposomes with light activated drug has been shown to result in an increased accumulation and more prolonged retention of light activated drugs within cultured malignant cells and within tumors in vivo. Jori et al., *Br. J. Cancer*, 48:307–309 (1983); Cozzani et al., *In Porphyrins in Tumor Phototherapy*, 173–183, Plenum Press (Andreoni et al. eds. 1984). As a result, inclusion of the light activated drug within a liposome combined with the localized delivery of the light activated drug can serve to enhance the localization of the light activated drug within the tissue site.

Including a light activated drug with the microbubbles has numerous advantages over microbubbles without light activated drug. After administration of microbubbles to a patient, the microbubbles often must be ruptured to achieve their therapeutic effects. One technique for rupturing microbubbles has been to expose the microbubbles to ultrasound energy. However, ultrasound energy of undesirably high intensity is frequently required to break the microbubbles. Further, the ultrasound energy frequently must be matched to the resonant frequency of the microbubbles. As a result, rupturing the microbubbles with ultrasound can present numerous challenges.

Activating a light activated drug within the microbubble and/or in the substrate of the microbubble can cause the microbubble to rupture. Activation of the light activated drug is believed to cause a disturbance which disrupts the shell of the microbubble enough to cause the microbubble to rupture. This disruption occurs when the light activated drug is coupled with the shell of the microbubble or is entirely within the microbubble. This disruption is also believed to occur when light activated drug located the media outside the microbubbles is activated in proximity of the microbubble. Accordingly, including a sufficient concentration light activated drug in the media outside the microbubble and activating a portion of that light activated drug can also cause rupture of the microbubbles. As a result, microbubbles can be ruptured by activating light activated drugs and without matching the ultrasound frequency to the resonant frequency of the microbubble. However, a more efficient rupturing of microbubbles can be achieved by delivering a level of ultrasound energy which is appropriate to activate the light activated drug and which is matched to the resonant frequency of the microbubble. Further, the cavitation threshold can require an ultrasound intensity which is lower than the intensity required to rupture microbubbles without light activated drugs. As a result, including light activated drug with microbubbles can reduce the intensity of ultrasound energy required to rupture the microbubble.

The threshold value of cavitation is also reduced in the proximity of many light activated drugs. As a result, the light activated drug encourages cavitation in the proximity of the light activated drug.

The interior of the microbubbles may include a gas or may be devoid of gas. When a gas is present, the gas can occupy any portion of the microbubble's volume but preferably occupies 0.01–50% of the volume of the microbubble interior, more preferably 5–30% and most preferably 10–20%. When the volume of gas is less than 0.01% of the volume, cavitation can be hindered and when the volume of gas is greater than 50% the structural integrity of the microbubble shell can become too weak for the microbubble to be transported to the tissue site. Suitable gasses for the interior of the microbubbles include, but are not limited to, biocompatible gasses such as air, nitrogen, carbon dioxide, oxygen, argon, fluorine, xenon, neon, helium, or combinations thereof. The presence of tiny bubbles is known to reduce the cavitation threshold. As a result, the presence of an appropriately sized gas bubble in the microbubble can enhance cavitation in the proximity of the light activated drug.

The microbubbles are preferably 0.01–100 μm in diameter. This size microbubble reduces excretion of the microbubble outside the body and also reduces interference of the microbubble with the flow of fluids within the body of the patient. Further, the microbubbles preferably have a shell thickness of 0.001–50 μm, 0.01–5 μm and 0.1–0.5 μm. This thickness provides the shells with sufficient thickness that the microbubble can withstand enough of the forces within the vasculature of a patient to be transported through at least a portion of the patient's vasculature. Similarly, the thickness can permit the microbubbles to be transported through a lumen in an apparatus such as a catheter. However, this thickness is also sufficiently thin that alteration of the ultrasound activated substance upon activation is sufficient to disrupt the shell of the microbubble and cause the microbubble rupture.

Activating the light activated drug to rupture microbubbles can cause the light activated drug to be released from the microbubble so the light activated drug can penetrate the tissue near the site of rupture. Further exposure of the light activated drug to ultrasound can activate the light activated drug within the tissue and cause death of the tissue as described above.

The microbubble can include a therapeutic in addition to the light activated drug. Activation of the light activated drug can serve to rupture the microbubble and release the therapeutic from the microbubble. As a result, the therapeutic is released in proximity to a tissue site by rupturing the microbubble in proximity to the tissue site. This is advantageous when the therapeutic can be detrimental when administered systemically. For instance, a therapeutic such as cisplatin is known to kill cancerous tissues but is also known to kill other tissues throughout the body. As a result, systemic administration of cisplatin can be detrimental. However, microbubbles can serve to protect tissues from the therapeutic agent until the therapeutic agent is released from the carrier. For instance, when the therapeutic is enclosed within the interior of the microbubble, contact between the therapeutic agent and tissues outside the carrier is reduced. As a result, the carrier increases protection of tissues outside the carrier are protected from the therapeutic agent until the microbubble is ruptured and the therapeutic released.

The therapeutics may be encapsulated in the microbubbles, included in the shell of the microbubbles or in the media outside the microbubbles. Therapeutic, as used herein, means an agent having beneficial effect on the patient.

Examples of therapeutics which can be included with the microbubbles include, but are not limited to, hormone products such as, vasopressin and oxytocin and their derivatives, glucagon and thyroid agents as iodine products and anti-thyroid agents; cardiovascular products as chelating agents and mercurial diuretics and cardiac glycosides; respiratory products as xanthine derivatives (theophylline & aminophylline); anti-infectives as aminoglycosides, antifungals (amphotericin), penicillin and cephalosporin antibiotics, antiviral agents as Zidovudine, Ribavirin, Amantadine, Vidarabine, and Acyclovir, anti-helmintics, antimalarials, and antituberculous drugs; biologicals as immune serums, antitoxins and antivenins, rabies prophylaxis products, bacterial vaccine, viral vaccines, toxoids; antineoplastics asnitrosureas, nitrogen mustards, antimetabolites (fluorouracil, hormones, asprogesings and estrogens and antiestrogens; antibiotics as Dactinomycin; mitotic inhibitors as Etoposide and the Vinca alkaloids, Radiopharmaceuticals as radioactive iodine and phosphorus products; as well as Interferon, hydroxyurea, procarbazine, Dacarbazine, Mitotane, Asparaginase and cyclosporins.

Other suitable therapeutics include, but are not limited to: thrombolytic agents such as urokinase; coagulants such as thrombin; antineoplastic agents, such as platinum compounds (e.g., spiroplatin, cisplatin, and carboplatin), methotrexate, adriamycin, taxol, mitomycin, ansamitocin, bleomycin, cytosine arabinoside, arabinosyl adsnine, mercaptopolylysine, vincristine, busulfan, chlorambucil, melphalan (e.g.,PAM, L-PAM or phenylalanine mustard), mercaptopurine, mitotane, procarbazine hydrochloride dactinomycin (actinomycin D), daunorubicinhydrochloride, doxorubicin hydrochloride, mitomycin, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase) Erwinaasparaginase, etoposide (VP-16), interferon alpha -2a, interferon alpha-2b, teniposide (VM-26), vinblastine sulfate (VLB), vincristine sulfate, bleomycin, bleomycin sulfate, methotrexate, adriamycin, and arabinosyl; blood products such as parenteral iron, hemin; biological response modifiers such as muramyldipeptide, muramyltripeptide, microbial cell wall components, lymphokines (e.g.,bacterial endotoxin such as lipopolysaccharide, macrophage activationfactor), sub-units of bacteria (such as Mycobacteria, Corynebacteria), the synthetic dipeptide N-acetyl-muramyl-L-alanyl-D-isoglutamine; antifungalagents such as ketoconazole, nystatin, griseofulvin, flucytosine (5-fc), miconazole, amphotericin B, ricin, and beta -lactam antibiotics (e.g.,sulfazecin); hormones such as growth hormone, melanocyte stimulating hormone, estradiol, beclomethasone dipropionate, betamethasone, betamethasone acetate and betamethasone sodium phosphate, vetamethasonedisodiumphosphate, vetamethasone sodium phosphate, cortisone acetate, dexamethasone, dexamethasone acetate, dexamethasone sodium phosphate, flunsolide, hydrocortisone, hydrocortisone acetate, hydrocortisonecypionate, hydrocortisone sodium phosphate, hydrocortisone sodium succinate, methylprednisolone, methylprednisolone acetate, methylprednisolonesodium succinate, paramethasone acetate, prednisolone, prednisoloneacetate, prednisolone sodium phosphate, prednisolone rebutate, prednisone, triamcinolone, triamcinolone acetonide, triamcinolone diacetate, triamcinolone hexacetonide and fludrocortisone acetate; vitamins such ascyanocobalamin neinoic acid, retinoids and derivatives such as retinolpalmitate, and alpha -tocopherol; peptides, such as manganese super oxidedimutase; enzymes such as alkaline phosphatase; anti-allergic agents such as amelexanox; anticoagulation agents such as phenprocoumon and heparin; circulatory drugs such as propranolol; metabolic potentiators such asglutathione; antituberculars such as para-aminosalicylic acid, isoniazid, capreomycin sulfate cycloserine, ethambutol hydrochloride ethionamide, pyrazinamide, rifampin, and streptomycin sulfate; antivirals such as acyclovir, amantadine azidothymidine (AZT or Zidovudine), Ribavirin andvidarabine monohydrate (adenine arabinoside, ara-A); antianginals such asdiltiazem, nifedipine, verapamil, erythrityl tetranitrate, isosorbidedinitrate, nitroglycerin (glyceryl trinitrate) and pentaerythritoltetranitrate; anticoagulants such as phenprocoumon, heparin; antibiotics such as dapsone, chloramphenicol neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin rifampin and tetracycline; antiinflammatories such as difunisal, ibuprofen, indomethacin, meclofenamate, mefenamic acid, naproxen, oxyphenbutazone, phenylbutazone, piroxicam, sulindac, tolmetin, aspirin and salicylates; antiprotozoans such as chloroquine, hydroxychloroquine, metronidazole, quinine and meglumine antimonate; antirheumatics such as penicillamine; narcotics such as paregoric; opiates such as codeine, heroin, methadone, morphine and opium; cardiac glycosides such as deslanoside, digitoxin, digoxin, digitalin and digitalis; neuromuscular blockers such as atracurium besylate, gallamine triethiodide, hexafluorenium bromide, metocurine iodide, pancuronium bromide, succinylcholine chloride (suxamethonium chloride), tubocurarine chloride and vecuronium bromide; sedatives (hypnotics) such as amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, pentobarbital sodium, phenobarbital sodium, secobarbital sodium, talbutal, temazepam and triazolam; local anesthetics such as bupivacaine hydrochloride, chloroprocaine hydrochloride, etidocainehydrochloride, lidocaine hydrochloride, mepivacaine hydrochloride, procainehydrochloride and tetracaine hydrochloride; general anesthetics such asdroperidol, etomidate, fentanyl citrate with droperidol, ketaminehydrochloride, methohexital sodium and thiopental sodium; and radioactive particles or ions such as strontium, iodide rhenium and yttrium.

In certain preferred embodiments, the therapeutic is a monoclonal antibody, such as a monoclonal antibody capable of binding to melanoma antigen.

Other preferred therapeutics include genetic material such as nucleic acids, RNA, and DNA, of either natural or synthetic origin, including recombinant RNA and DNA and antisense RNA and DNA. Types of genetic material that may be used include, for example, genes carried on expression vectors such as plasmids, phagemids, cosmids, yeast artificial chromosomes (YACs), and defective or "helper" viruses, antigene nucleic acids, both single and double stranded RNA and DNA and analogs thereof, such asphosphorothioate and phosphorodithioate oligodeoxynucleotides. Additionally, the genetic material may be combined, for example, with proteins or other polymers.

Examples of genetic therapeutics that may be included in the microbubbles include DNA encoding at least a portion of an HLAgene, DNA encoding at least a portion of dystrophin, DNA encoding at least a portion of CFTR, DNA encoding at least a portion of IL-2, DNA encoding at least a portion of TNF, an antisense oligonucleotide capable of binding the DNA encoding at least a portion of Ras.

DNA encoding certain proteins may be used in the treatment of many different types of diseases. For example, adenosine deaminase may be provided to treat ADA deficiency; tumor necrosis factor and/or interleukin-2 may be provided to treat advanced cancers; HDL receptor may be provided to treat liver disease; thymidine kinase may be provided to treat ovarian cancer, brain tumors, or HIV infection; HLA-B7 may be provided to treat malignant melanoma; interleukin-2 may be provided to treat neuroblastoma, malignant melanoma, or kidney cancer; interleukin-4 may be provided to treat cancer; HIV env may be provided to treat HIV infection; antisense ras/p53 may be provided to treat lung cancer; and Factor VIII may be provided to treat Hemophilia B. See, for example, Science 258, 744–746.

If desired, more than one therapeutic may be included in the media For example, a single microbubble may contain more than one therapeutic or microbubbles containing different therapeutics may be co-administered. By way of example, a monoclonal antibody capable of binding to melanoma antigen and an oligonucleotide encoding at least a portion of IL-2 may be administered in a single microbubble. The phrase "at least a portion of," as used herein, means that the entire gene need not be represented by the oligonucleotide, so long as the portion of the gene represented provides an effective block to gene expression. Further, microbubbles including a therapeutic can be administered before, after, during or intermittently with the administration of microbubbles without a therapeutic. For instance, microbubbles without a therapeutic and microbubbles including a coagulant such as thrombin can be administered to a patient having liver cancer. Activating the light activated drug included with the microbubbles serves to rupture the microbubbles and release the light activated drug and thrombin from the microbubbles. Further activation of the light activated drug can cause tissue death and the thrombin can cause coagulation in and around the damaged tissues.

Prodrugs may be included in the microbubbles, and are included within the ambit of the term therapeutic, as used herein. Prodrugs are well known in the art and include inactive drug precursors which, when exposed to high temperature, metabolizing enzymes, cavitation and/or pressure, in the presence of oxygen or otherwise, or when released from the microbubbles, will form active drugs. Such prodrugs can be activated via the application of ultrasound to the prodrug-containing microbubbles with the resultant cavitation, heating, pressure, and/or release from the microbubbles. Suitable prodrugs will be apparent to those skilled in the art, and are described, for example, in Sinkula et al., J. Pharm. Sci. 1975 64, 181–210, the disclosure of which is hereby incorporated herein by reference in its entirety. Prodrugs, for example, may comprise inactive forms of the active drugs wherein a chemical group is present on the prodrug which renders it inactive and/or confers solubility or some other property to the drug. In this form, the prodrugs are generally inactive, but once the chemical group has been cleaved from the prodrug, by heat, cavitation, pressure, and/or by enzymes in the surrounding environment or otherwise, the active drug is generated. Such prodrugs are well described in the art and comprise a wide variety of drugs bound to chemical groups through bonds such as esters to short, medium or long chain aliphatic carbonates, hemiesters of organic phosphate, pyrophosphate, sulfate, amides, amino acids, azo bonds, carbamate, phosphamide, glucosiduronate, N-acetylglucosamine and beta-glucoside. Examples of drugs with the parent molecule and the reversible modification or linkage are as follows: convallatoxin with ketals, hydantoin with alkyl esters, chlorphenesin with glycine or alanins esters, acetaminophen with caffeine complex, acetylsalicylic acid with THAM salt, acetylsalicylic acid with acetamidophenyl ester, naloxone with sulfateester, 15-methylprostaglandin F sub 2 with methyl ester, procaine with polyethylene glycol, erythromycin with alkyl esters, clindamycin with alkylesters or phosphate esters, tetracycline with betains salts, 7-acylaminocephalosporins with ring-substituted acyloxybenzyl esters, nandrolone with phenylproprionate decanoate esters, estradiol with enolether acetal, methylprednisolone with acetate esters, testosterone with n-acetylglucosaminide glucosiduronate (trimethylsilyl) ether, cortisol or prednisolone or dexamethasone with 21-phosphate esters. Prodrugs may also be designed as reversible drug derivatives and utilized as modifiers to enhance drug transport to site-specific tissues. Examples of parent molecules with reversible modifications or linkages to influence transport to a site specific tissue and for enhanced therapeutic effect include isocyanate with haloalkyl nitrosurea, testosterone with propionateester, methotrexate (3-5'-dichloromethotrexate) with dialkyl esters, cytosine arabinoside with 5'-acylate, nitrogen mustard (2,2'-dichloro-N-methyldiethylamine), nitrogen mustard with aminomethyltetracycline, nitrogen mustard with cholesterol or estradiol ordehydroepiandrosterone esters and nitrogen mustard with azobenzene. As one skilled in the art would recognize, a particular chemical group to modify a given drug may be selected to influence the partitioning of the drug into either the shell or the interior of the microbubbles. The bond selected to link the chemical group to the drug may be selected to have the desired rate of metabolism, e.g., hydrolysis in the case of ester bonds in the presence of serum esterases after release from the microbubbles. Additionally, the particular chemical group may be selected to influence the biodistribution of the drug employed in the microbubbles, e.g., N,N-bis(2-chloroethyl)-phosphorodiamidicacid with cyclic phosphoramide for ovarian adenocarcinoma. Additionally, the prodrugs employed within the microbubbles may be designed to contain reversible derivatives which are utilized as modifiers of duration of activity to provide, prolong or depot action effects. For example, nicotinic acid may be modified with dextran and carboxymethlydextran esters, streptomycin with alginic acid salt, dihydrostreptomycin with pamoate salt, cytarabine (ara-C) with 5'-adamantoats ester, ara-adenosine (ara-A) with 5-palmirate and 5'-benzoate esters, amphotericin B with methyl esters, testosterone with 17-beta -alkyl esters, estradiol with formate ester, prostaglandin with 2-(4imidazolyl) ethylamine salt, dopamine with amino acid amides, chloramphenicol with mono- and bis(trimethylsilyl) ethers, and cycloguanil with pamoate salt. In this form, a depot or reservoir of long-acting drug may be released in vivo from the prodrug bearing microbubbles. In addition, compounds which are generally thermally labile may be utilized to create toxic free radical compounds. Compounds with azolinkages, peroxides and disulfide linkages which decompose with high temperature are preferred. With this form of prodrug, azo, peroxide or disulfide bond containing compounds are activated by cavitation and/or increased heating caused by the interaction of ultra with the microbubbles to create cascades of free radicals from these prodrugs entrapped therein. A wide variety of drugs or chemicals may constitute these prodrugs, such as azo compounds, the general structure of such compounds being R—N=N—R, wherein R is a hydrocarbon chain, where the double bond between the two nitrogen atoms may react to create free radical products in vivo. Exemplary drugs or compounds which may be used to create free radical products include azo containing compounds such as azobenzene, 2,2'-azobisisobutyronitrile, azodicarbonamide, azolitmin, azomycin, azosemide, azosulfamide, azoxybenzene, aztreonam, sudan III, sulfachrysoidine, sulfamidochrysoidine and sulfasalazine, compounds containing disulfide bonds such as sulbentine, thiamine disulfide, thiolutin, thiram, compounds containing peroxides such as hydrogen peroxide and benzoylperoxide, 2,2'-azobisisobutyronitrile, 2,2'-azobis(2-amidopropane) dihydrochloride, and 2,2'-azobis(2,4dimethylvaleronitrile). A microbubble having oxygen gas on its interior should create extensive free radicals with cavitation. Also, metal ions from the transition series, especially manganese, iron and copper can increase the rate of formation of reactive oxygen intermediates from oxygen. By including metal ions within the microbubbles, the formation of free radicals in vivo can be increased. These metal ions may be incorporated into the microbubbles as freesalts, as complexes, e.g., with EDTA, DTPA, DOTA or desferrioxamine, or asoxides of the metal ions. Additionally, derivatized complexes of the metal ions may be bound to lipid head groups, or lipophilic complexes of the ions may be incorporated into a lipid bilayer, for example. When exposed to thermal stimulation, e.g., cavitation, these metal ions then will increase the rate of formation of reactive oxygen intermediates. Further, radiosensitizers such as metronidazole and misonidazole may be incorporated into the gas-filled liposomes to create free radicals on thermal stimulation. By way of an example of the use of prodrugs, an acylated chemical group may be bound to a drug via an ester linkage which would readily cleave in vivo by enzymatic action in serum. The acylated prodrug can be included in the microbubble. When the microbubble is ruptured, the prodrug will then be exposed to the serum. The ester linkage is then cleaved by esterases in the serum, thereby generating the drug. Similarly, ultrasound may be utilized not only to activate the light activated drug so as to burst the gas-filled liposome, but also to cause thermal effects which may increase the rate of the chemical cleavage and the release of the active drug from the prodrug. The microbubbles may also be designed so that there is a symmetric or an asymmetric distribution of the therapeutic both inside and outside of the microbubble. The particular chemical structure of the therapeutics may be selected or modified to achieve desired solubility such that the therapeutic may either be encapsulated within the interior of the microbubble or couple with the shell of the microbubble. The shell-bound therapeutic may bear one or more acyl chains such that, when the microbubble is popped or heated or ruptured via cavitation, the acylated therapeutic may then leave the surface and/or the therapeutic may be cleaved from the acyl chains chemical group. Similarly, other therapeutics may be formulated with a hydrophobic group which is aromatic or sterol in structure to incorporate into the surface of the microbubble.

When the microbubble is a liposome, the liposomes can be "fast breaking". In fast breaking liposomes, the light activated drug-liposome combination is stable in vitro but, when administered in vivo, the light activated drug is rapidly released into the bloodstream where it can associate with serum lipoproteins. As a result, the localized delivery of liposomes combined with the fast breaking nature of the liposomes can result in localization of the light activated drug and/or the therapeutic in the tissues near the catheter. Further, the fast breaking liposomes can prevent the liposomes from leaving the vicinity of the catheter intact and then concentrating in non-targeted tissues such as the liver. Delivery of ultrasound energy from the catheter can also serve to break apart the liposomes after they have been delivered from the catheter.

A catheter for locally delivering a media including a light activated drug includes an elongated body with at least one utility lumen extending through the elongated body. The utility lumens can be used to deliver the media including the light activated drug locally to a tissue site and/or to receive a guidewire so the catheter can be guided to the tissue site. The ultrasound assembly can include an ultrasound transducer designed to transmit ultrasound energy which activates the light activated drug.

A support member can support the ultrasound transducer adjacent to an outer surface of the elongated body so as to define a chamber between the ultrasound transducer and the elongated body. The chamber can be filled with a material which creates a low acoustic impedance to reduce the exposure of at least one utility lumen within the elongated body to ultrasound energy delivered from the ultrasound transducer. For instance, the chamber can be filled with a material which absorbs, reflects or prevents transmission of ultrasound energy through the chamber. Alternatively, the chamber can be evacuated to reduce transmission of ultrasound energy through the chamber. Reducing the exposure of at least one lumen to the ultrasound energy reduces exposure of media delivered through the at least one lumen to the ultrasound energy. As a result, the effect of the ultrasound energy on the light activated drug is reduced until the light activated drug has been delivered out of the catheter. Further, ultrasound energy is known to rupture microbubbles. As a result, when the media includes microbubbles, the chamber reduces the opportunity for the ultrasound energy to rupture the microbubbles within the catheter.

The support member can have ends which extend beyond the ultrasound member. As a result, the chamber can be positioned adjacent to the entire longitudinal length of the ultrasound transducer and can extend beyond the ends of the ultrasound transducer. This configuration maximizes the portion of the ultrasound transducer which is adjacent to the chamber. Increasing the portion of ultrasound transducer adjacent to the chamber can reduce the amount of ultrasound energy transmitted to the utility lumens. The ultrasound assembly can include an outer coating over the ultrasound transducer. Temperature sensors can be positioned in the outer coating adjacent to ultrasound transducer. The temperature sensors feedback information regarding the temperature adjacent to the ultrasound transducers where the thermal energy has a reduced opportunity to dissipate. As a result, the temperature sensors provide a measure of the temperature on the exterior surface of the transducer.

FIGS. 1A–1B illustrates a catheter 10 for delivering a media including a light activated drug to a tissue site. The catheter 10 includes an ultrasound assembly 12 for delivering ultrasound energy to light activated drug within the tissue site. The catheter 10 includes an elongated body 14 with a utility lumen 16 extending through the elongated body 14. The utility lumen 16 can receive a guidewire (not shown) so the catheter 10 can be threaded along the guidewire. The utility lumen 16 can also be used for the delivering media which include a light activated drug. A fiber optic can also be positioned in the utility lumen 16 to provide a view of the tissue site or to provide light to the tissue site. As a result, the catheter can also be used as an endoscope.

The ultrasound assembly 12 can also include an outer coating 18. Suitable outer coatings 18 include, but are not limited to, polyimide, parylene and polyester. An ultrasound transducer 20 is positioned within the outer coating 18. Suitable ultrasound transducers 20 include, but are not limited to, PZT-4D, PZT-4, PZT-8 and cylindrically shaped piezoceramics. When the ultrasound transducer 20 has a cylindrical shape, the ultrasound transducer 20 can encircle the elongated body 14 as illustrated in FIG. 1C. One or more temperature sensors 22 can be positioned in the outer coating 18. The temperature sensors 22 can be positioned adjacent to the ultrasound transducer 20 to provide feedback regarding the temperature adjacent to the ultrasound transducer 20. The temperature sensors can be in electrical communication with an electrical coupling 24. The electrical coupling 24 can be coupled with a feedback control system (not shown) which adjusts the level of the ultrasound energy delivered from the ultrasound transducer 20 in response to the temperature at the temperature sensors 22.

The catheter 10 can include a perfusion lumen 25. The perfusion lumen 25 allows fluid to flow from outside the catheter into the utility lumen 16. Once a guidewire has been removed from the utility lumen 16, fluid flow which is obstructed by the ultrasound assembly can continue through the perfusion lumen 25 and the utility lumen.

As illustrated in FIGS. 2A–2B, the ultrasound assembly 12 can be flush with the elongated body 14. Further, the ultrasound transducer 20 and the temperature sensors 22 can be positioned within the elongated body 14. This configuration of elongated body 14 and ultrasound transducer 20 can eliminate the need for the outer coating 18 illustrated in FIGS. 1A–1C.

As illustrated in FIG. 3A, the catheter 10 can also include a media delivery port 26, a media inlet port 28 and a second utility lumen 16A. The media inlet port 28 is designed to be coupled with a media source (not shown). Media can be transported from the media source and through the media delivery port 26 via the second utility lumen 16A. As a result, a guidewire can be left within the utility lumen 16 while media is delivered via the second utility lumen 16A.

FIG. 4A illustrates a catheter 10 including a plurality of ultrasound assemblies 12. FIGS. 4B–4C are cross sections of a catheter 10 with a second utility lumen 16A coupled with the media delivery ports 26. The second utility lumen 16A can also be coupled with the media inlet port 28 illustrated in FIG. 4A. The media inlet port 28 is designed to be coupled with a media source (not shown). Media can be transported from the media source and through the media delivery ports 26 via the second utility lumen 16A.

The catheter 10 can include a balloon 30 as illustrated in FIG. 5A. The balloon 30 can be constructed from an impermeable material or a permeable membrane or a selectively permeable membrane which allows certain media to flow through the membrane while preventing other media from flowing through the membrane. Suitable membranous materials for the balloon 30 include, but are not limited to cellulose, cellulose acetate, polyvinylchloride, polyolefin, polyurethane and polysulfone. When the balloon 30 is constructed from a permeable membrane or a selectively permeable membrane, the membrane pore sizes are preferably 5 A–2 μm, more preferably 50 A–900 A and most preferably 100 A–300 A in diameter.

As illustrated in FIG. 5B, an ultrasound assembly 12, a first media delivery port 26A and a second media delivery port 26B can be positioned within the balloon 30. The first and second media delivery ports 26A, 26B are coupled with a second utility lumen 16A and third utility lumen 16B. The second and third utility lumens 16A , 16B can be coupled with the same media inlet port 28 or with independent media inlet ports 28. When the first and second media delivery ports 26A, 26B are coupled with different media inlet ports 28, different media can be delivered via the second and third media delivery ports 26A, 26B. For instance, a medication media can be delivered via the third utility lumen 16B and an expansion media can be delivered via the second utility lumen 16A. The medication media can include drugs or other medicaments which can provide a therapeutic effect The expansion media can serve to expand the balloon 30 or wet the membrane comprising the balloon 30. Wetting the membrane comprising the balloon 30 can cause a minimally permeable membrane to become permeable.

The ultrasound assembly 12 can be positioned outside the balloon 30 as illustrated in FIGS. 6A–6C. In FIG. 6A the balloon 30 is positioned distally of the ultrasound assembly 12 and in FIG. 6B the ultrasound assembly 12 is positioned distally of the balloon 30. FIG. 6C is a cross section a catheter 10 with an ultrasound assembly 12 positioned outside the balloon 30. The catheter includes a second utility lumen 16A coupled with a first media delivery port 26A. The second utility lumen 16A can be used to deliver an expansion media and/or a medication media to the balloon 30. When the balloon 30 is constructed from a permeable membrane, the medication media and/or the expansion media can pass through the balloon 30. Similarly, when the balloon 30 is constructed from a selectively permeable membrane, particular components of the medication media and/or the expansion media can pass through the balloon 30. Pressure can be used to drive the media or components of the media across the balloon 30. Other means such as phoresis can also be used to drive the media or components of the media across the balloon 30.

As illustrated in FIG. 6C, the ultrasound assembly 12 may be positioned at the distal end of the catheter 10. The second utility lumen 16A can be used to deliver an expansion media and/or a medication media to the balloon 30. The utility lumen 16 can be used to deliver a medication media as well as to guide the catheter 10 along a guidewire.

As illustrated in FIGS. 7A–7C, the catheter 10 can include a second media assembly 12 and the second media delivery port 26B are positioned distally relative to a balloon 30, however, the balloon 30 can be positioned distally relative to the ultrasound assembly 12 and the second media delivery port 26B. In FIG. 7A the ultrasound assembly 12 is positioned distally of the second media delivery port 26B and in FIG. 7B the second media delivery port 26B is positioned distally of the ultrasound assembly 12.

FIG. 7C is a cross section of the catheter 10 illustrated in FIG. 7A. The catheter 10 includes first and second media delivery ports 26A, 26B coupled with a second utility lumen 16A and third utility lumen 16B. The second and third utility lumens 16A, 16B can be coupled with independent media inlet ports 28 (not shown). The second utility lumen 16A can be used to deliver an expansion media and/or a medication media to the balloon 30 while the third utility lumen 16B can be used to deliver a medication media through the second media delivery port 26B.

As illustrated in FIGS. 8A–8B, the catheter 10 can include a first balloon 30A and a second balloon 30B. The ultrasound assembly 12 can be positioned between the first and second balloons 30A, 30B. A second media delivery port 26B can optionally be positioned between the first and second balloons 30A, 30B. In FIG. 8A the second media delivery port 26B is positioned distally relative to the ultrasound assembly and in FIG. 8B the ultrasound assembly is positioned distally relative to the second media delivery port 26B.

FIG. 8C is a cross section of the first balloon 30A illustrated in FIG. 8B. The catheter includes a second, third and fourth utility lumens 16A, 16B, 16C. The second utility lumen 16A is coupled with a first media delivery port 26A within the first balloon. The third utility lumen 16B is coupled with the second media delivery port 26B and the fourth utility lumen 16C is coupled with a third media delivery port 26C in the second balloon 30B (not shown). The second and fourth utility lumens 16A, 16C can be used to deliver expansion media and/or medication media to the first and second balloon 30A, 30B. The second and fourth utility lumens 16A, 16C can be coupled with the same media inlet port or with independent media inlet ports (not shown). When the second and fourth utility lumens are coupled with the same media inlet port, the pressure within the first and second balloons 30A, 30B will be similar. When the second and fourth utility lumens are coupled with independent media inlet ports, different pressures can be created within the first and second balloons 30A, 30B. The third utility lumen 16B can be coupled with an independent media inlet port and can be used to deliver a medication media via the second media delivery port 26B.

FIGS. 9A–9I illustrate operation of various embodiments of catheters 10 for delivering ultrasound energy to a light activated drug within a tissue site. FIGS. 9A–9I illustrate the tissue site 32 as an atheroma in a vessel 34, however, it is contemplated that the catheter 10 can be used with other tissue sites 32 such as a tumor and that the catheter 10 can be positioned within the vasculature of the tumor. In each of FIGS. 9A–9I, the catheter 10 is illustrated as being within a vessel 34. The catheter 10 can be positioned within the vessel 34 by applying conventional over-the-guidewire techniques and can be verified by including radiopaque markers upon the catheter 10.

In FIG. 9A, the catheter 10 is positioned so the ultrasound assembly 12 is adjacent to a tissue site 32 within a vessel 34. When the catheter 10 is in position, the guidewire is removed from the utility lumen 16 and media can be delivered via the utility lumen 16 as illustrated by the arrows 36. In FIG. 9A, the media includes microbubbles 38 but can alternatively be an emulsion. The media is delivered to the tissue site 32 via the utility lumen 16 and ultrasound energy 40 is delivered from the ultrasound assembly 12. Suitable periods for delivering the ultrasound energy include., but are not limited to, 1 minute to three hours, 2 minutes to one hour and 10–30 minutes.

Suitable intensities for the ultrasound energy include, but are not limited to, 0.1–1000 W/cm$^2$, 1–100 W/cm$^2$ and 10–50 W/cm$^2$. Suitable frequencies for the ultrasound energy include, but are not lmited to, 10 kHz–100 MHz and 10 kHz–50 MHz but is preferably 20 kHz–10 MHz. Suitable ultrasound energies also include, but are not limited to 0.02 to 10 w/cm$^2$ at a frequency of about 20 KHz to about 10 MHz and more preferably about 0.3 W/cm$^2$ at a frequency of about 1.3 MHz. The ultrasound energy can be intermittently switched between a first and second frequency to increase the efficiency of microbubble rupture and to increase activation of the light activated drug. For instance, the ultrasound energy can be switched between about 100 kHz and about 270 kHz in short pulses of approximately 0.001–10 seconds duration. Similarly, the ultrasound energy can be switched between first and second intensities. When the catheter includes a plurality of ultrasound transducers as will be discussed below, the first and second frequencies can be provided by different ultrasound transducers. Similarly, the first and second intensities can be provided by different ultrasound transducers. Further, when the catheter includes a plurality of ultrasound transducers each transducer can simultaneously transmit ultrasound energy with different intensity and/or frequency.

The delivery of ultrasound energy 40 can be before, after, during or intermittently with the delivery of the microbubbles 38. As discussed above, the microbubbles 38 can be "fast breaking" so they rupture upon exiting the utility lumen and being exposed to the vessel 34. As described above, the ultrasound energy from the ultrasound assembly 12 can cause the microbubbles 38 within the delivered media to rupture. As will be described in more detail below, the ultrasound assembly can be designed to reduce the exposure of media within the catheter 10 to the ultrasound energy from the ultrasound assembly 12. When the catheter 10 is so designed, the number of microbubbles 38 which rupture within the catheter is reduced and the number of microbubbles 38 which rupture outside the catheter is increased.

Delivery of the ultrasound energy before delivery of the light activated drug can enhance absorption of the light activated drug into the tissue site. Delivery of the ultrasound energy a pre-determined time after delivery of the light activated drug can provide the light activated drug time to penetrate the tissue site. The predetermined time can be of sufficient duration that at least a portion of the light activated drug penetrates into the tissue site. The predetermined time can also be of sufficient duration that the light activated drug localizes within the lipid rich tissue of the atheroma. Sufficient time between delivery of the media and the ultrasound energy include but are not limited to, 1 minute to 48 hours, 1 minute to 3 hours, 1 to 15 minutes and 1 to 2 minutes. Once the light activated drug has penetrated the tissue site 32, the ultrasound energy from the ultrasound assembly 12 can activate the light activated dug within the tissue site 32 so as to cause tissue death within the tissue site 32.

Figure 9C:
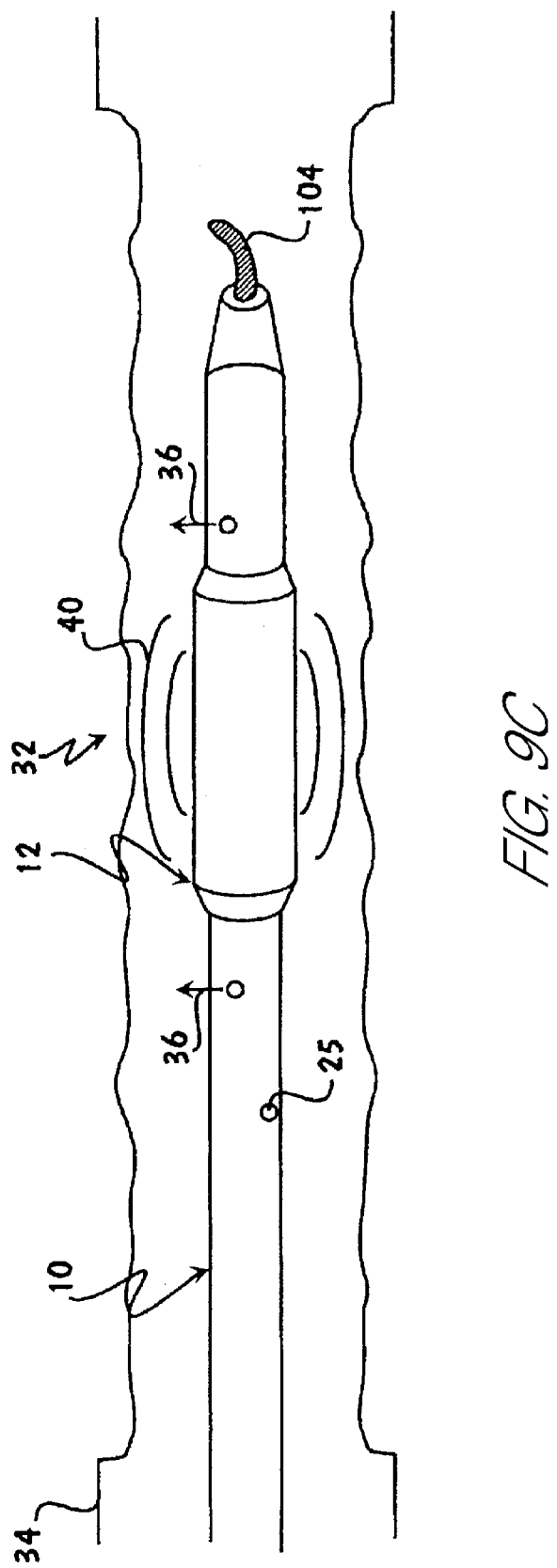
FIG. 9C illustrates an ultrasound assembly positioned adjacent to a tissue site and a media delivered via a media delivery port while a guidewire is positioned in a utility lumen.

In FIG. 9B, ultrasound energy 40 is delivered from the ultrasound transducer 20 and a media is delivered through the media delivery port 26 as illustrated by the arrows 36. The delivery of ultrasound energy 40 can be before, after, during or intermittently with the delivery of the media via the media delivery port 26. As illustrated in FIG. 9C, the guidewire 104 can remain in the utility lumen 16 during the delivery of the media via the media delivery ports 26. As will be discussed in further detail below, the ultrasound assembly can be designed to reduce the transmission of the ultrasound energy into the utility lumen. Because the transmission of ultrasound energy 40 into the utility lumen 16 is reduced, the change in the frequency of the ultrasound transducer 20 which is due to the presence of the guidewire in the utility lumen 16 is also reduced.

Figure 9D:
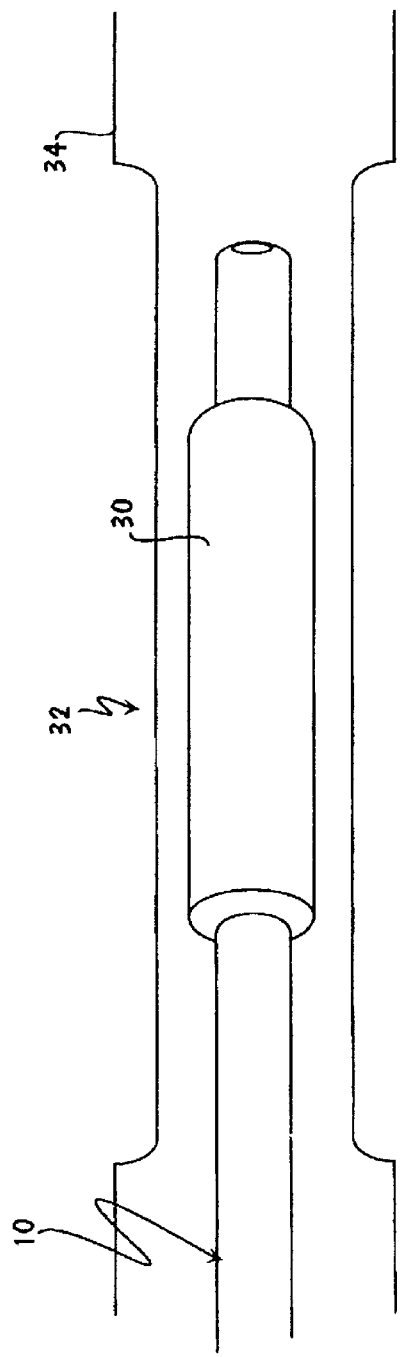
FIG. 9D illustrates a catheter including a balloon positioned adjacent to a tissue site.
Figure 9E:
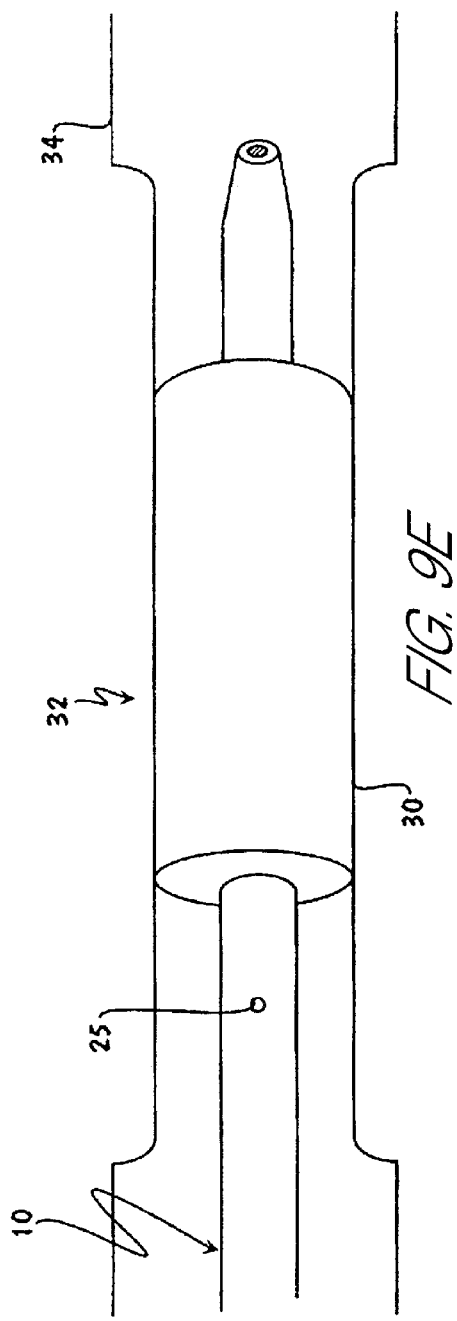
FIG. 9E illustrates a catheter including a balloon expanded into contact with a tissue site.

In FIG. 9D, a catheter 10 including a balloon 30 is positioned with the balloon adjacent to the tissue site 32. In FIG. 9E, the balloon 30 is expanded into contact with the tissue site 32. As discussed above, the catheter 10 can include a perfusion lumen which permits a continuous flow of fluid from the vessel through the utility lumen during the partial or full obstruction of the vessel by the balloon. When the balloon 30 is constructed from a membrane or a selectively permeable membrane a media can be delivered to the tissue site 32 via the balloon 30. The media can serve to wet the membrane or can include a drug or other medicament which provides a therapeutic effect. Ultrasound energy 40 can be delivered from the ultrasound assembly 12 before, after, during or intermittently with the delivery of the media. The ultrasound energy 40 can serve to drive the media across the membrane via phonophoresis or can enhance the therapeutic effect of the media In FIG. 9F a catheter 10 with an ultrasound assembly 12 outside a balloon 30 is positioned at the tissue site 32 so the ultrasound assembly 12 is adjacent to the tissue site 32. A fluid within the vessel flows past the balloon as indicated by the arrow 42. In FIG. 9G, the balloon 30 is expanded into contact with the vessel 34. The balloon 30 can be constructed from an impermeable material so the vessel 34 is occluded. As a result, the fluid flow through the vessel 34 is reduced or stopped. A medication media is delivered through the utility lumen 16 and ultrasound energy 40 is delivered from the ultrasound assembly 12. In embodiments of the catheter 10 including a media delivery port 26 outside of the balloon 30 (i.e. FIGS. 7A–7C), the medication media can be delivered via the media delivery port 26. Further, a first medication media can be delivered via the media delivery port 26 while a second medication media can be delivered via the utility lumen 16 or while a guidewire is positioned within the utility lumen 16. The ultrasound energy 40 can be delivered from the ultrasound assembly 12 before, after, during or intermittently with the delivery of the media. The occlusion of the vessel 34 before the delivery of the media can serve to prevent the media from being swept from the tissue site 32 by the fluid flow. Although the balloon 30 illustrated in FIGS. 9F–9G is positioned proximally relative to the ultrasound assembly 12, the fluid flow through the vessel 34 can also be reduced by expanding a single balloon 30 which is positioned distally relative to the ultrasound assembly 12.

Figure 9H:
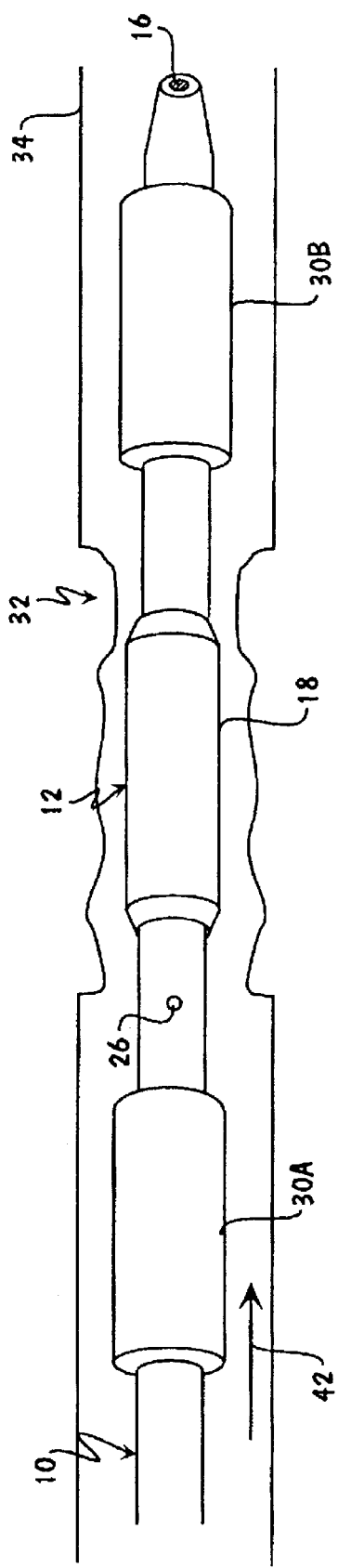
FIG. 9H illustrates a catheter with an ultrasound assembly outside a first and second balloon positioned at a tissue site.
Figure 9I:
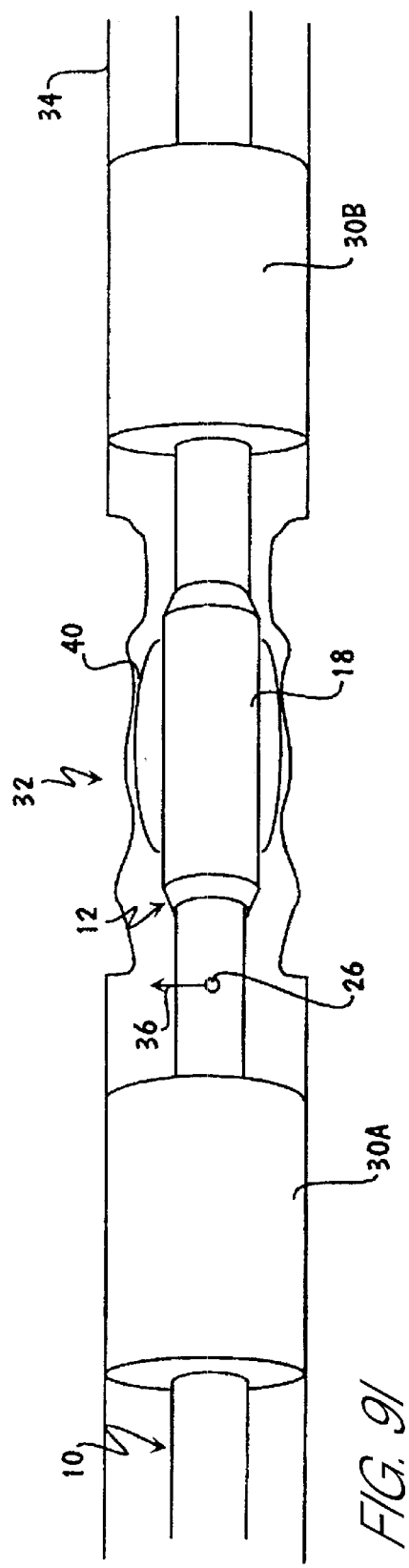
FIG. 9I illustrates the first and second balloon of FIG. 9H expanded into contact with a vessel so as to occlude the vessel.

In FIG. 9H a catheter 10 including a first balloon 30A and a second balloon 30B is positioned at a tissue site 32 so the ultrasound assembly 12 is positioned adjacent to the tissue site 32. A fluid within the vessel 34 flows past the balloon 30 as indicated by the arrow 42. In FIG. 9I, the first and second balloons 30A, 30B are expanded into contact with the vessel 34. The first and second balloons 30A, 30B can be constructed from an impermeable material so the vessel 34 is occluded proximally and distally of the ultrasound assembly 12. As a result, the fluid flow adjacent to the tissue site 32 is reduced or stopped. A medication media is delivered through the media delivery port 26 and ultrasound energy 40 is delivered from the ultrasound assembly 12. The ultrasound energy 40 can be delivered from the ultrasound assembly 12 before, after, during or intermittently with the delivery of the media The occlusion of the vessel 34 before the delivery of the media can serve to prevent the media from being swept from the tissue site 32 by the fluid flow.

In each of the FIGS. 9A–9I illustrated above, the media can be systemically delivered. The catheter 10 is positioned adjacent to the tissue site before, after or during the systemic administration of the media When the media includes microbubbles which must be burst before their therapeutic effect can be obtained, the ultrasound energy can be delivered after the microbubbles have had sufficient time to reach the desired tissue site in sufficient concentrations. A level of ultrasound which ruptures the microbubbles is then delivered from the ultrasound assembly. After rupture of the microbubbles, the delivery of ultrasound energy can be stopped to provide the light activated drug or other therapeutic time to penetrate the tissue site. The delivery of the ultrasound energy can also be continuous to maximize the number of microbubbles which are burst.

When the media is systemically delivered and the light activated drug is included in media which does not require an ultrasound activated release, the behavior of the light activated drug within the patient must be taken into consideration. As described above, many light drugs such as the macrocycles, initially disperse throughout the body and where they are taken up by most tissues. After a period of time, usually between 3 and 48 hours, the drug clears from most normal tissue and is retained to a greater degree in lipid rich regions such as the liver, kidney, tumor and atheroma. As a result, when the tissue site is not a lipid rich region, the ultrasound energy should be delivered to the tissue site within 3 to 48 hours of systemically administering the media. However, when the tissue site is lipid rich, improved results can be achieved by waiting 3 to 48 hours after systemic administration of the media before delivering the ultrasound energy.

FIG. 10A provides a cross section of an ultrasound assembly which reduces transmission of ultrasound energy from the ultrasound transducer into the catheter. The ultrasound assembly 12 includes a support member 44. Suitable support members 44 include, but are not limited to, polyimide, polyester and nylon. The support member 44 can be attached to the ultrasound transducer 20. Suitable means for attaching the ultrasound transducer 20 to the support member 44 include, but are not limited to, adhesive bonding and thermal bonding.

Figure 10D:
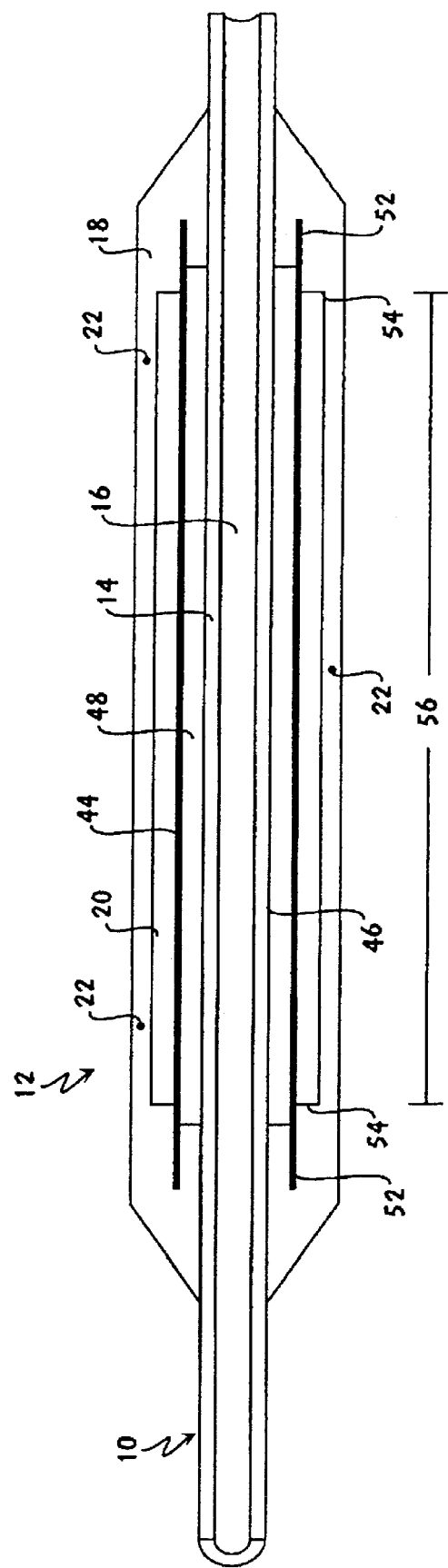
FIG. 10D illustrates a support member which is supported by an outer coating.

The support member 44 supports the ultrasound transducer 20 at an external surface 46 of the elongated body 14 such that a chamber 48 is defined between the ultrasound transducer 20 and the external surface 46 of the elongated body 14. The chamber 48 preferably has a height from 0.25–10 $\mu$m, more preferably from 0.50–5 $\mu$m and most preferably from 0.0–1.5 $\mu$m. The support member 44 can be supported by supports 50 positioned at the ends 52 of the support member 44 as illustrated in FIG. 10A. The supports 50 can be integral with the support member 44 as illustrated in FIG. 10C. The outer coating 18 can serve as the supports as illustrated in FIG. 10D.

The ends 52 of the support member 44 can extend beyond the ends 54 of the ultrasound transducer 20. The supports 50 can be positioned beyond the ends 54 of the ultrasound transducer 20. As a result, the chamber 48 can extend along the longitudinal length 56 of the ultrasound transducer 20, maximizing the portion of the ultrasound transducer 20 which is adjacent to the chamber 48. The chamber 48 can be filled with a medium which absorbs ultrasound energy or which prevents transmission of ultrasound energy. Suitable gaseous media for filling the chamber 48 include, but are not limited to, helium, argon, air and nitrogen. Suitable media for filling the chamber 48 include, but are not limited to, silicon and rubber. The chamber 48 can also be evacuated. Suitable pressures for an evacuated chamber 48 include, but are not limited to, negative pressures to −760 mm Hg.

Figure 11A:
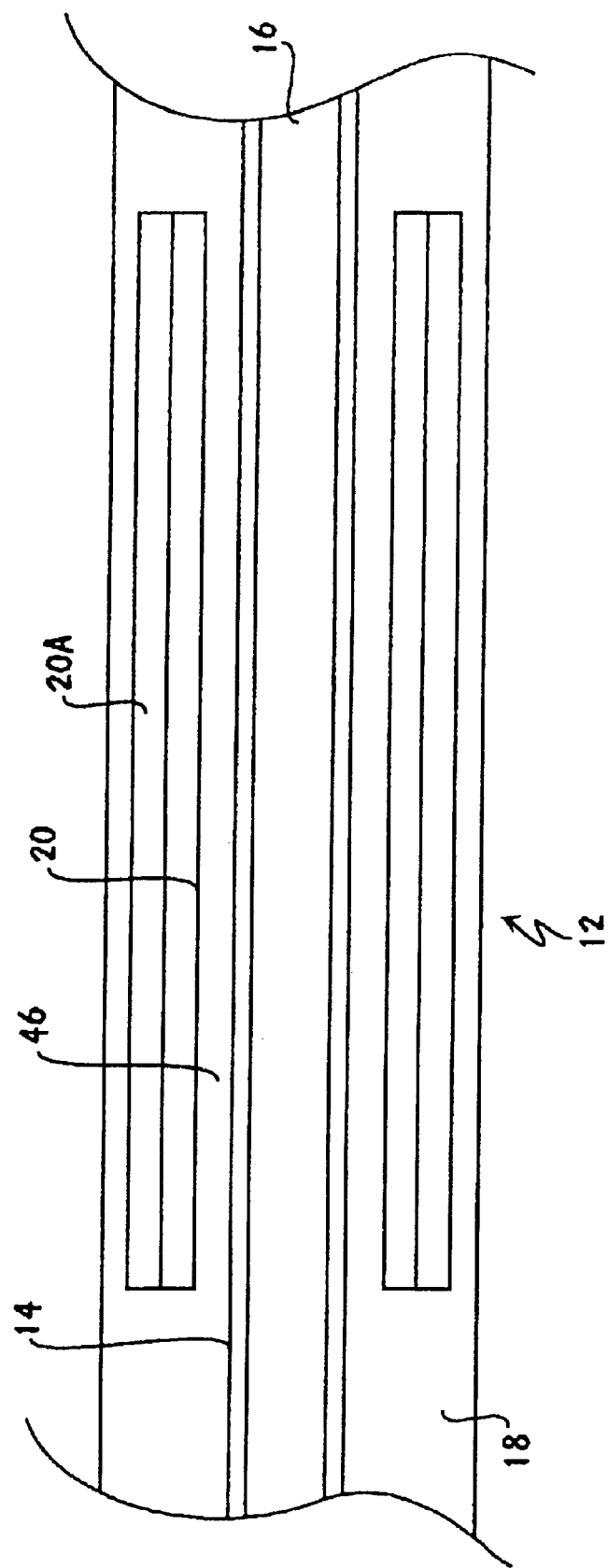
FIG. 11A is a cross section of an ultrasound assembly including two concentric ultrasound transducers in contact with one another.
Figure 11B:
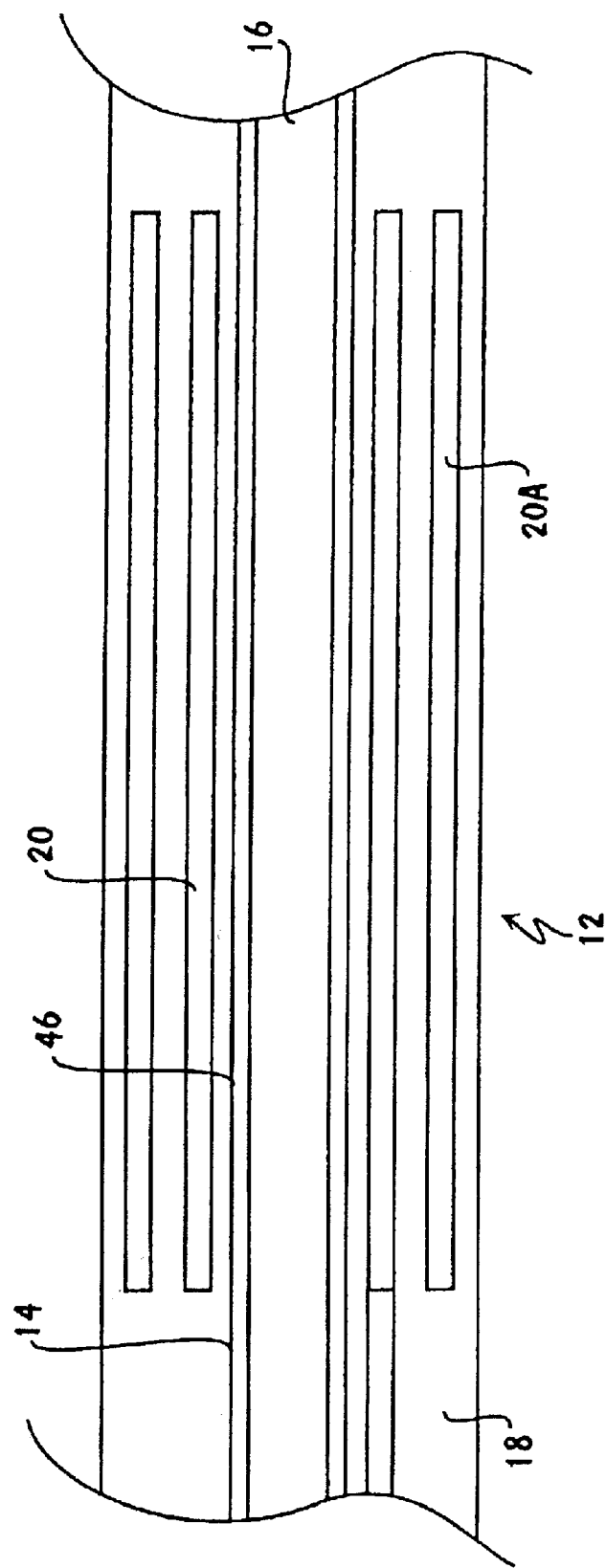
FIG. 11B is a cross section of an ultrasound assembly including two separated and concentric ultrasound transducers.
Figure 11C:
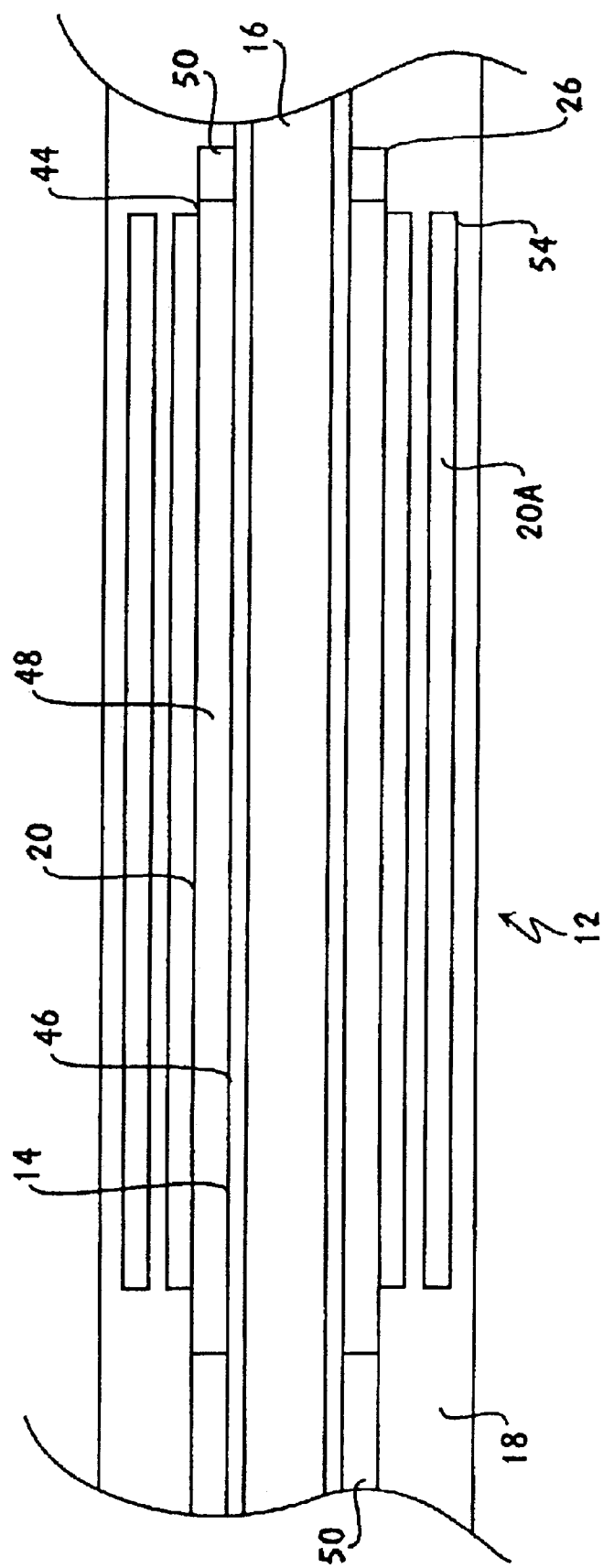
FIG. 11C is a cross section of an ultrasound assembly including two ultrasound transducers where a chamber is defined between one of the ultrasound transducers and an elongated body.
Figure 11D:
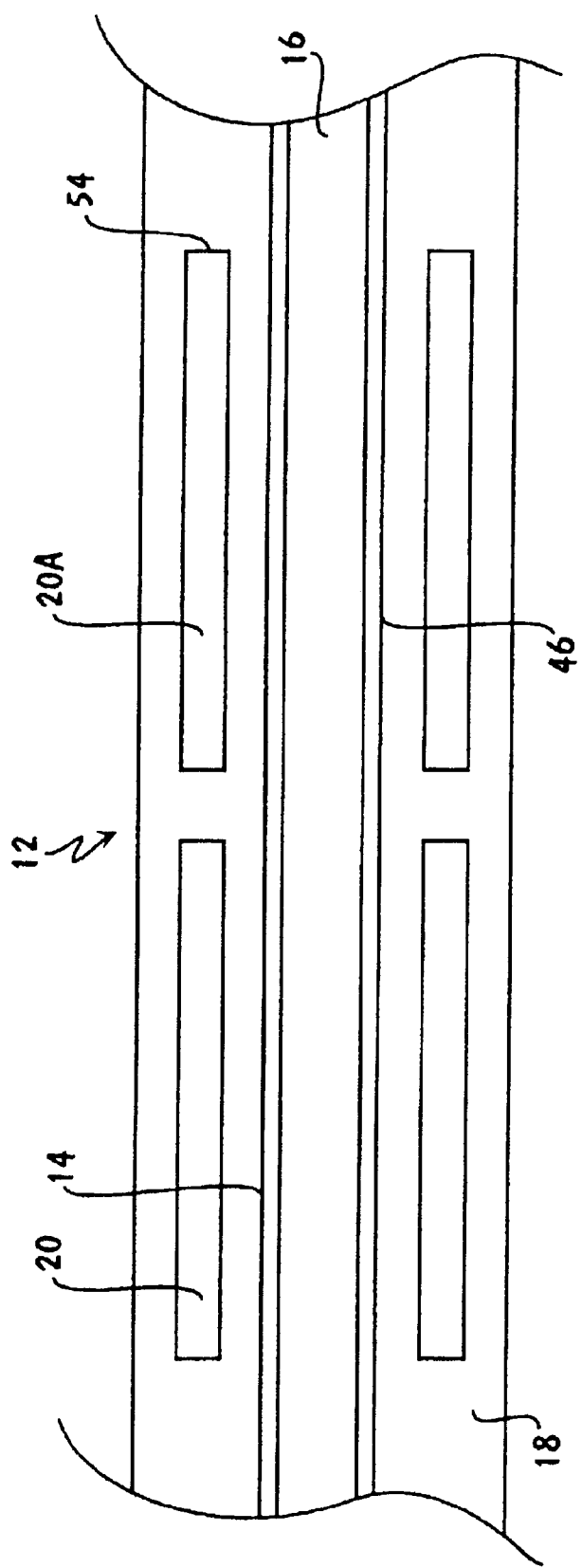
FIG. 11D is a cross section of an ultrasound assembly including two longitudinally adjacent ultrasound transducers in physical contact with one another.
Figure 11E:
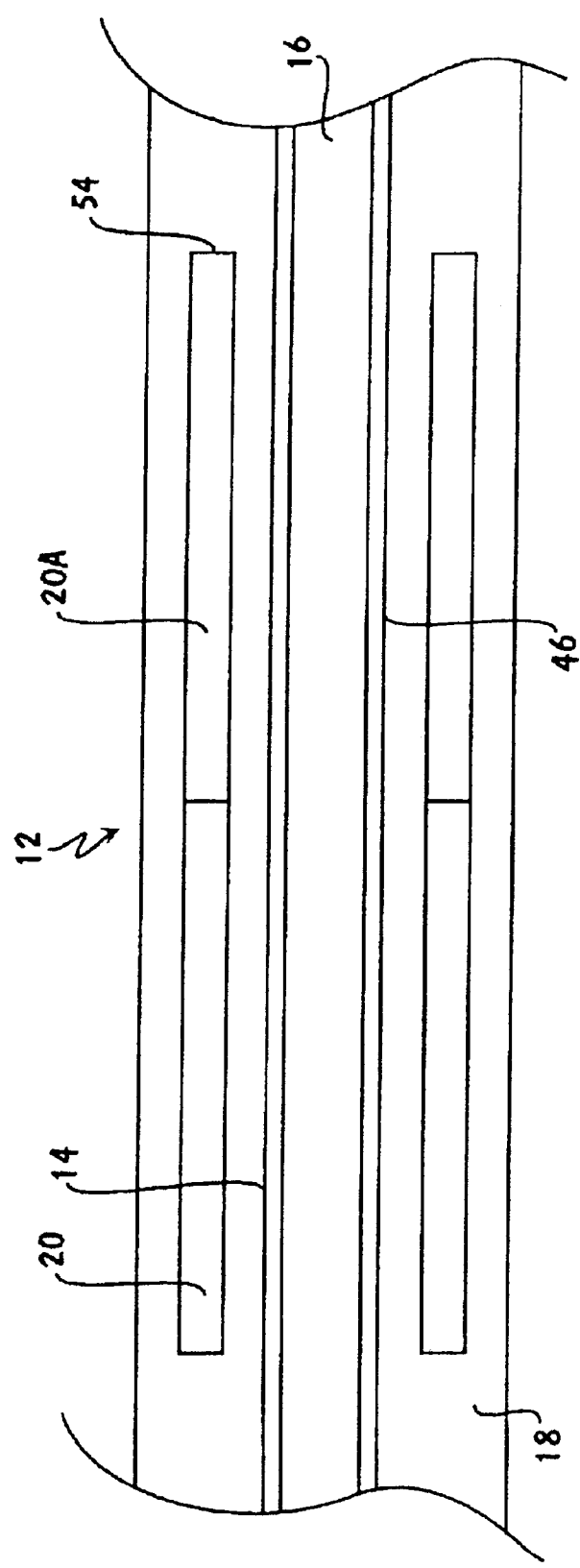
FIG. 11E is a cross section of an ultrasound assembly including two separated and longitudinally adjacent ultrasound transducers.
Figure 11F:
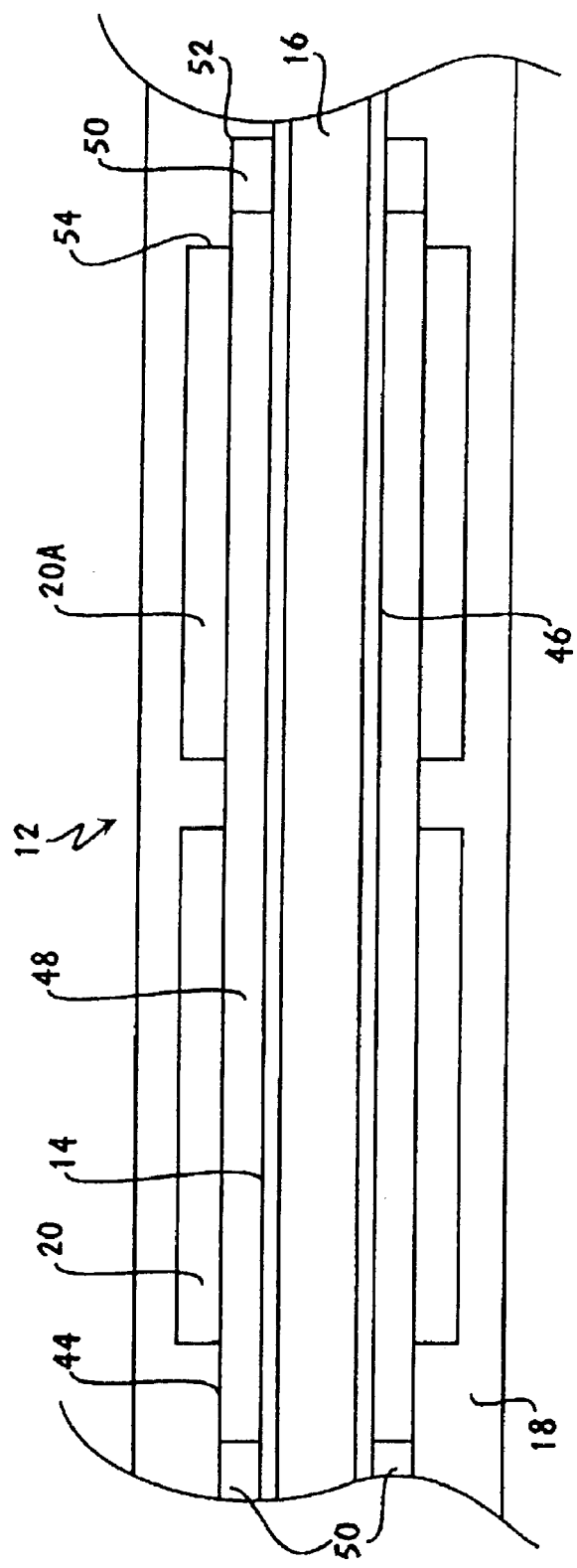
FIG. 11F is a cross section of an ultrasound assembly including two longitudinally adjacent ultrasound transducers with a single chamber positioned between both ultrasound transducers and an elongated body.
Figure 11G:
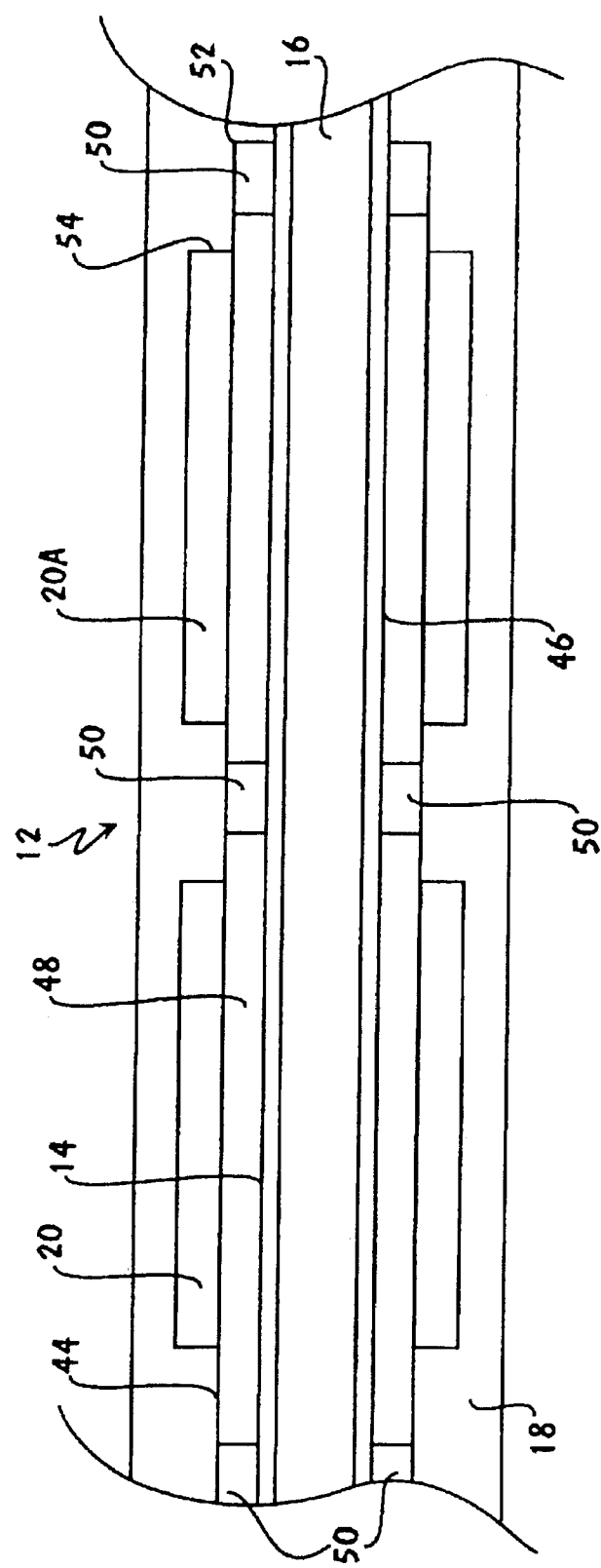
FIG. 11G is a cross section of an ultrasound assembly including two longitudinally adjacent ultrasound transducers with different chambers positioned between each ultrasound transducers and an elongated body.
Figure 11H:
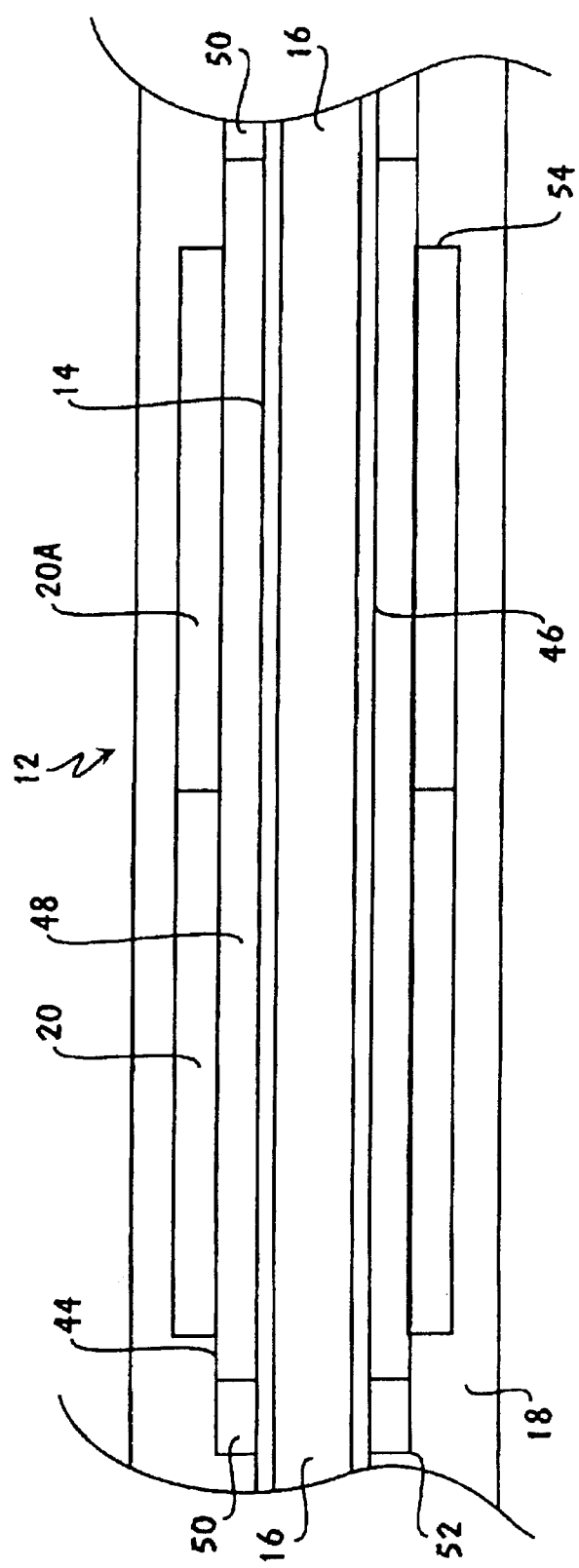
FIG. 11H is a cross section of an ultrasound assembly including two longitudinally adjacent ultrasound transducers in contact with one another and having a single chamber positioned between each ultrasound transducers and an elongated body.

The ultrasound assembly can include a second ultrasound transducer 20A as illustrated in FIGS. 11A–11H. In FIGS. 11A–11C one ultrasound transducer encircles the other and in FIGS. 11D–11H the ultrasound transducers are longitudinally adjacent to one another. The ultrasound transducers 20, 20A can be in contact with one another as illustrated in FIGS. 11A, 11E and 11H or separated from one another as illustrated in FIGS. 11B–11D, 11F and 11G. A single chamber 54 can be defined between the ultrasound transducers 20, 20A and the external surface 46 of the elongated body 14 as illustrated in FIGS. 11C, 11F and 11G or a different chamber can be defined between each of the ultrasound transducers 20, 20A and the external surface 46. Although the ultrasound transducers 20, 20A in FIGS. 11A–11C are illustrated as having the same longitudinal length, the longitudinal length may be different.

In FIGS. 11A–11H, the different temperature sensors can be positioned adjacent to different ultrasound transducers 20, 20A. As a result, the temperature adjacent to different ultrasound transducers 20, 20A can be detected and the level of ultrasound energy produced by each ultrasound transducer adjusted in response to the detected temperature.

When the ultrasound assembly includes a second transducer 20A, the transducers 20, 20A may be constructed from the same or different materials. Both transducers 20, 20A may be configured to radiate ultrasound energy in the same direction. Further, one transducer may be configured to transmit ultrasound energy in a radial direction and the other in a longitudinal direction in order to increase the angular spectrum over which ultrasound energy can be simultaneously transmitted. The ultrasound transducers can be configured to transmit ultrasound energy having the same or different characteristics. The transmission of ultrasound energy with different characteristics allows the same ultrasound assemblies e used to perform different functions. For instance, one ultrasound transducer can transmit a frequency which is appropriate for activating a light activated drug while the second ultrasound transducer transmits a frequency appropriate for enhancing penetration of a therapeutic agent into the treatment site. The transducers can be independently or simultaneously. When the transducers are operated simultaneously, the ultrasound assembly produces a waveform which is more complex than a single ultrasound transducer. More complex waveforms can provide advantages such as more efficient rupture of microbubbles. It is also contemplated that the ultrasound assembly can include three or more ultrasound transducers arranged similar to the transducers illustrated in FIGS. 11A–11H.

Figure 12A:
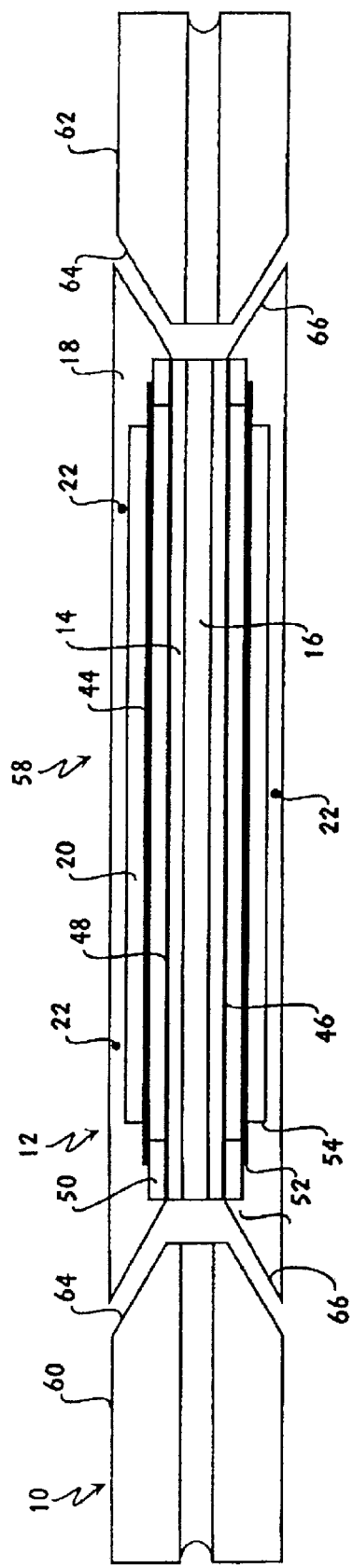
FIG. 12A is a cross section of a catheter which includes an ultrasound assembly module which is independent of a first catheter component and a second catheter component.
Figure 12B:
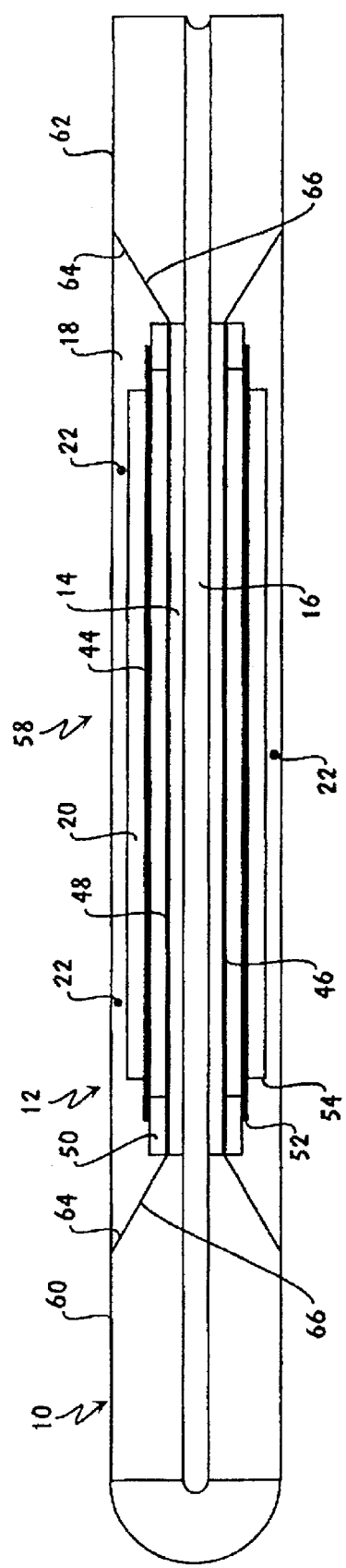
FIG. 12B illustrates the first and second catheter components coupled with the ultrasound assembly module.
Figure 12C:
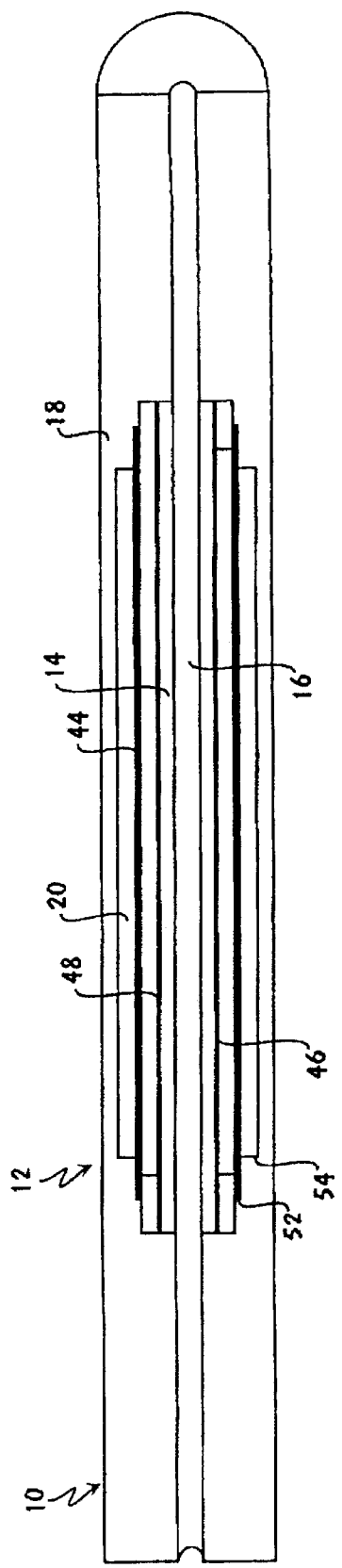
FIG. 12C is a cross section of an ultrasound assembly which is integral with a catheter.

The ultrasound assembly 12 can be a separate module 58 as illustrated in FIGS. 12A–12B. In FIG. 12A, the catheter 10 includes a first catheter component 60 a second catheter component 62 and an ultrasound assembly module 58. The first and second catheter components 60, 62 include component ends 64 which are complementary to the ultrasound assembly module ends 66. The component ends 64 can be coupled with the ultrasound assembly module ends 66 as illustrated in FIG. 12B. Suitable means for coupling the component ends 64 and the ultrasound assembly module ends 66 include, but are not limited to, adhesive, mechanical and thermal methods. The ultrasound assembly 12 can be integral with the catheter 10 as illustrated in FIG. 12C. Further, the outer coating 18 can have a diameter which is larger than the diameter of the elongated body 14 as illustrated in FIG. 10A or can be flush with the external surface 46 of the elongated body 14 as illustrated in FIGS. 12A–12C.

Figure 13A:
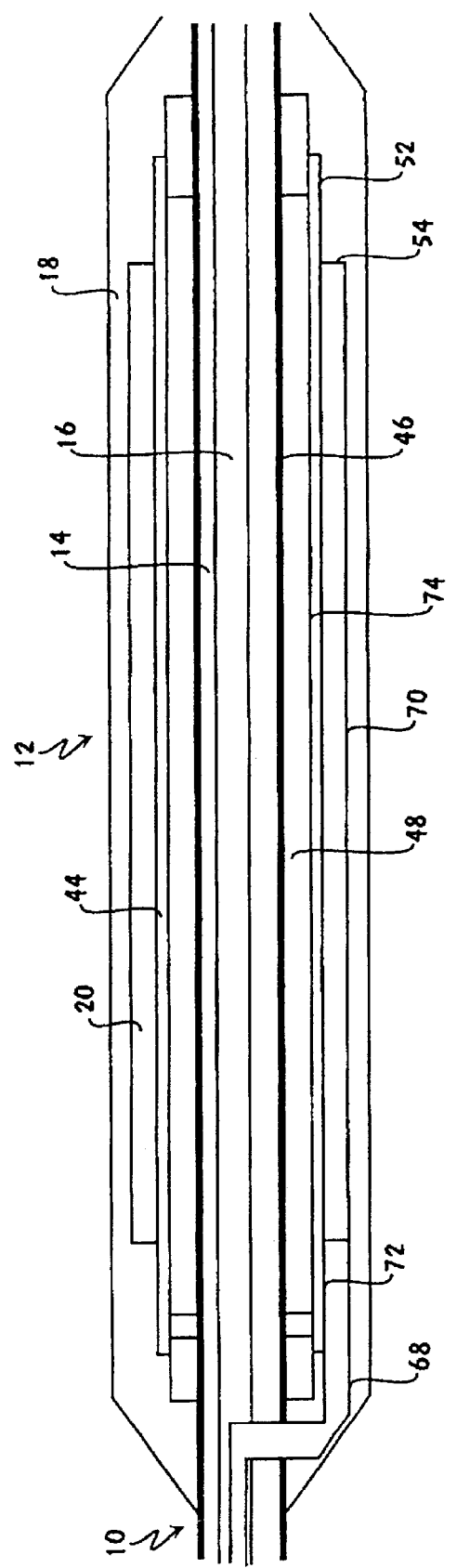
FIG. 13A is a cross section of an ultrasound assembly configured to radiate ultrasound energy in a radial direction. The lines which drive the ultrasound transducer pass through a utility lumen in the catheter.
Figure 13B:
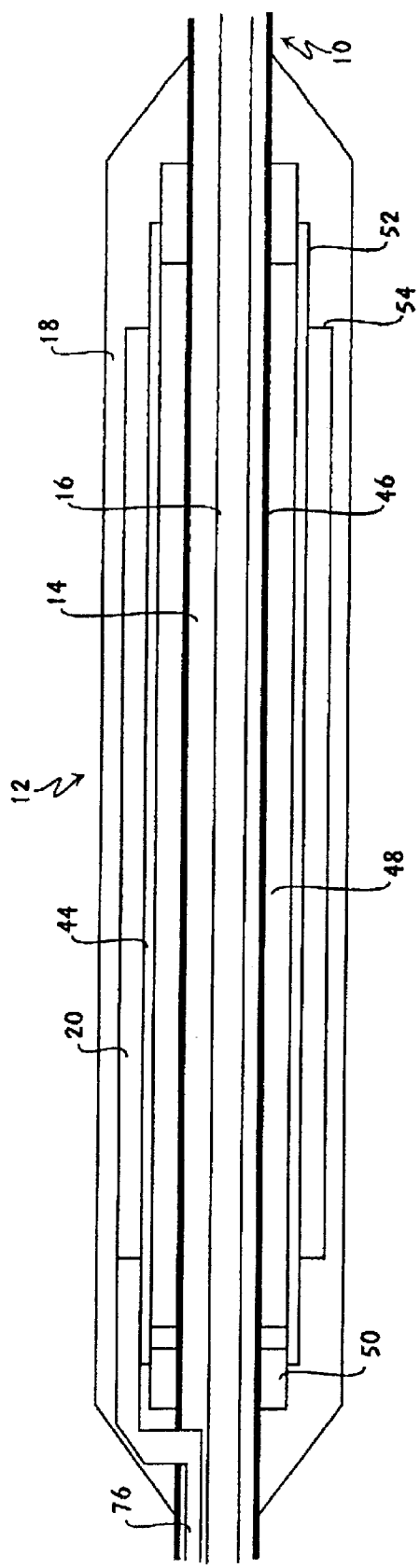
FIG. 13B is a cross section of an ultrasound assembly configured to radiate ultrasound energy in a radial direction. The lines which drive the ultrasound transducer pass through line lumens in the catheter.

The ultrasound assembly 12 can be electrically coupled to produce radial vibrations of the ultrasound transducer 20 as illustrated in FIGS. 13A–13B. A first line 68 is coupled with an outer surface 70 of the ultrasound transducer 20 while a second line 72 is coupled with an inner surface 74 of the ultrasound transducer 20. The first and second lines 68, 72 can pass proximally through the utility lumen 16 as illustrated in FIG. 13A. Alternatively, the first and second lines 68, 72 can pass proximally through line lumens 76 within The catheter 10 as illustrated in FIG. 13B. Suitable lines for the ultrasound transducer 20 include, but are not limited to, copper, gold and aluminum. Suitable frequencies for the ultrasound energy delivered by the ultrasound transducer 20 include, but are not limited to, 20 KHz to 2 MHz.

Figure 13C:
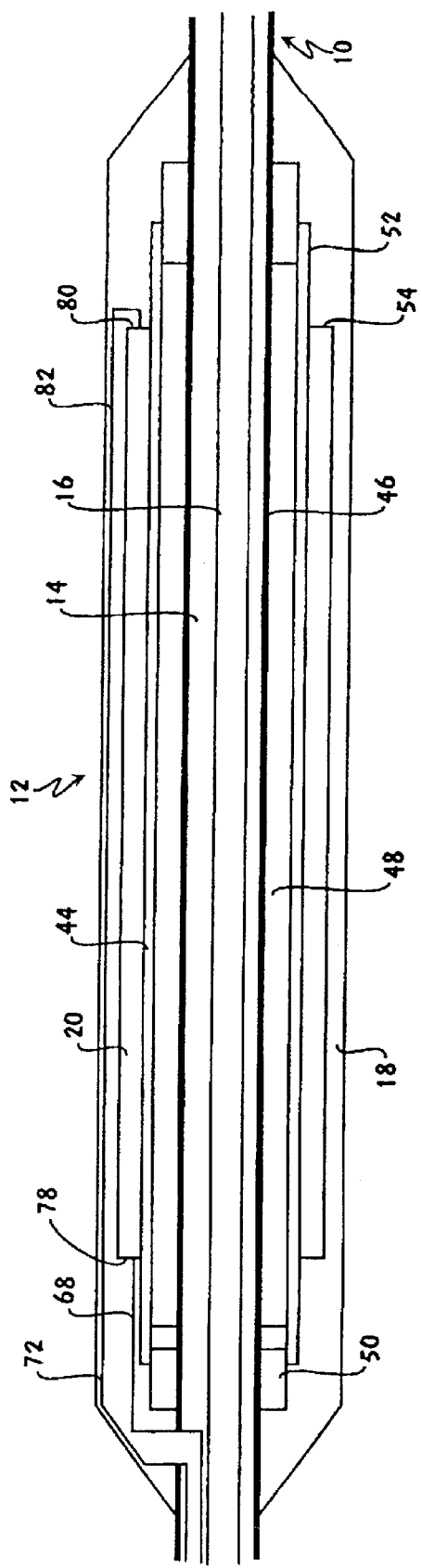
FIG. 13C is a cross section of an ultrasound assembly configured to longitudinally radiate ultrasound energy. The distal portion of one line travels proximally through the outer coating.
Figure 13D:
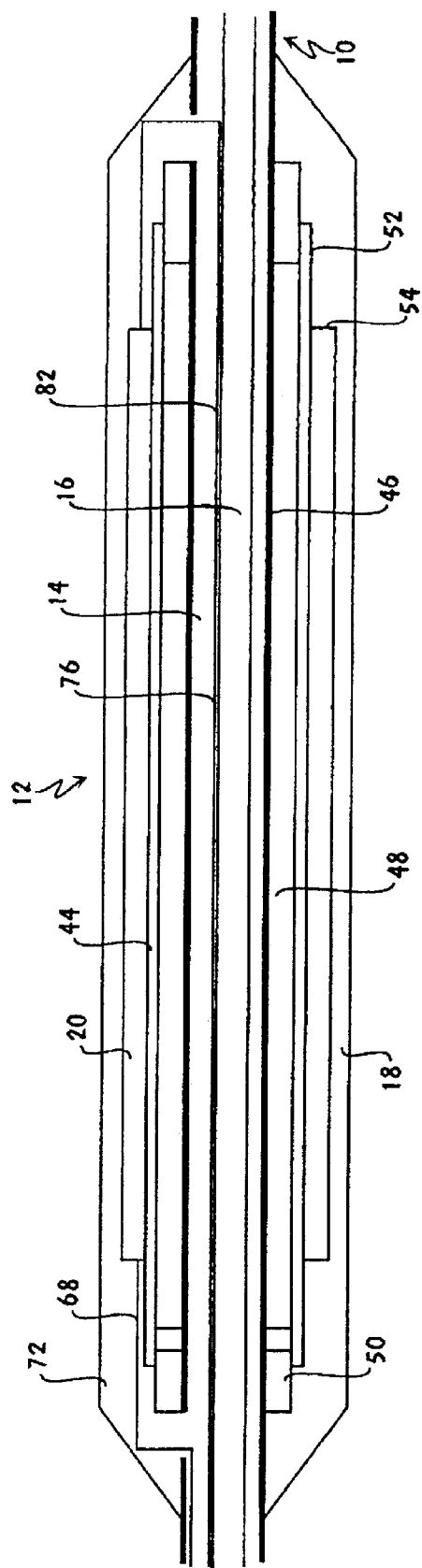
FIG. 13D is a cross section of an ultrasound assembly configured to longitudinally transmit ultrasound energy. The distal portion of one line travels proximally through a line lumen in the catheter.

The ultrasound assembly 12 can be electrically coupled to produce longitudinal vibrations of the ultrasound transducer 20 as illustrated in FIGS. 13C–13D. A first line 68 is coupled with a first end 78 of the ultrasound transducer 20 while a second line 72 is coupled with a second end 80 of the ultrasound transducer 20. The distal portion 82 of the second line 72 can pass through the outer coating 18 as illustrated in FIG. 13C. Alternatively, the distal portion 82 of the second line 72 can pass through line lumens 76 in the catheter 10 as illustrated in FIG. 13D. As discussed above, the first and second lines 68, 72 can pass proximally through the utility lumen 16.

As discussed above, the catheter 10 can include a plurality of ultrasound assemblies. When the catheter 10 includes a plurality of ultrasound assemblies, each ultrasound transducer 20 can each be individually powered. When the elongated body 14 includes N ultrasound transducers 20, the elongated body 14 must include 2N lines to individually power N ultrasound transducers 20. The individual ultrasound transducers 20 can also be electrically coupled in serial or in parallel as illustrated in FIGS. 14A–14B. These arrangements permit maximum flexibility as they require only 2 lines. Each of the ultrasound transducers 20 receive power simultaneously whether the ultrasound transducers 20 are in series or in parallel. When the ultrasound transducers 20 are in series, less current is required to produce the same power from each ultrasound transducer 20 than when the ultrasound transducers 20 are connected in parallel. The reduced current allows smaller lines to be used to provide power to the ultrasound transducers 20 and accordingly increases the flexibility of the elongated body 14. When the ultrasound transducers 20 are connected in parallel, an ultrasound transducer 20 can break down and the remaining ultrasound transducers 20 will continue to operate.

Figure 14C:
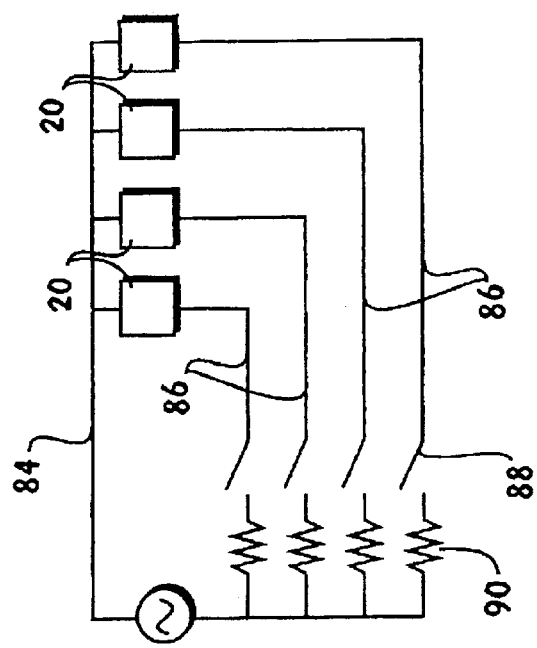
FIG. 14C illustrates ultrasound transducers connected with a common line.
Figure 14A:
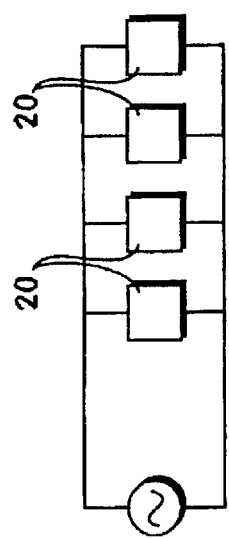
FIG. 14A illustrates ultrasound transducers connected in parallel.
Figure 14B:
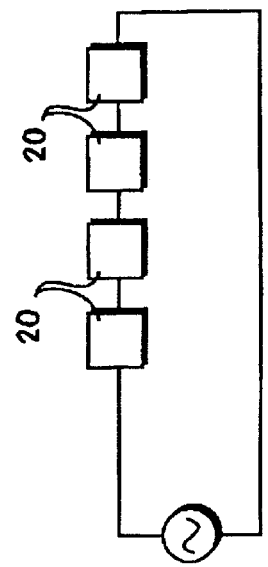
FIG. 14B illustrates ultrasound transducers connected in series.

As illustrated in FIG. 14C, a common line 84 can provide power to each ultrasound transducer 20 while each ultrasound transducer 20 has its own return line 86. A particular ultrasound transducer 20 can be individually activated by closing a switch 88 to complete a circuit between the common line 84 and the particular ultrasound transducer's 20 return line 86. Once a switch 88 corresponding to a particular ultrasound transducer 20 has been closed, the amount of power supplied to the ultrasound transducer 20 can be adjusted with the corresponding potentiometer 90. Accordingly, an catheter 10 with N ultrasound transducers 20 requires only N+1 lines and still permits independent control of the ultrasound transducers 20. This reduced number of lines increases the flexibility of the catheter 10. To improve the flexibility of the catheter 10, the individual return lines 86 can have diameters which are smaller than the common line 84 diameter. For instance, in an embodiment where N ultrasound transducers 20 will be powered simultaneously, the diameter of the individual return lines 86 can be the square root of N times smaller than the diameter of the common line 84.

As discussed above, the ultrasound assembly 12 can include at least one temperature sensor 22. Suitable temperature sensors 22 include, but are not limited to, thermistors, thermocouples, resistance temperature detectors (RTD)s, and fiber optic temperature sensors 22 which use thermalchromic liquid crystals. Suitable temperature sensor geometries include, but are not limited to, a point, patch, stripe and a band encircling the ultrasound transducer 20.

Figure 15:
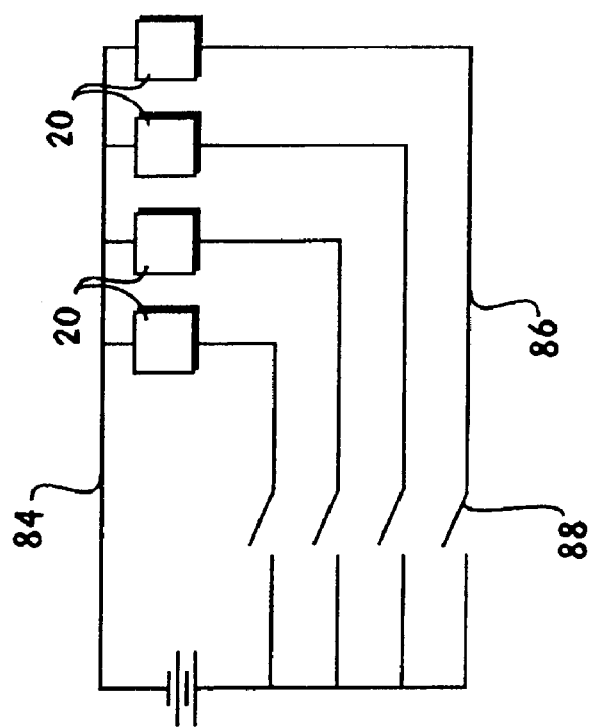
FIG. 15 illustrates a circuit for electrically coupling temperature sensors.

When the ultrasound assembly 12 includes a plurality of temperature sensors 22, the temperature sensors 22 can be electrically connected as illustrated in FIG. 15. Each temperature sensor 22 can be coupled with a common line 84 and then include its own return line 86. Accordingly, N+1 lines can be used to independently sense the temperature at the temperature sensors 22 when N temperature sensors 22 are employed. A suitable common line 84 can be constructed from Constantine and suitable return lines 86 can be constructed from copper. The temperature at a particular temperature sensor 22 can be determined by closing a switch 88 to complete a circuit between the thermocouple's return line 86 and the common line 84. When the temperature sensors 22 are thermocouples, the temperature can be calculated from the voltage in the circuit. To improve the flexibility of the catheter 10, the individual return lines 86 can have diameters which are smaller than the common line 84 diameter.

Each temperature sensor 22 can also be independently electrically coupled. Employing N independently electrically coupled temperature sensors 22 requires 2N lines to pass the length of the catheter 10.

The catheter 10 flexibility can also be improved by using fiber optic based temperature sensors 22. The flexibility can be improved because only N fiber optics need to be employed sense the temperature at N temperature sensors 22.

Figure 16:
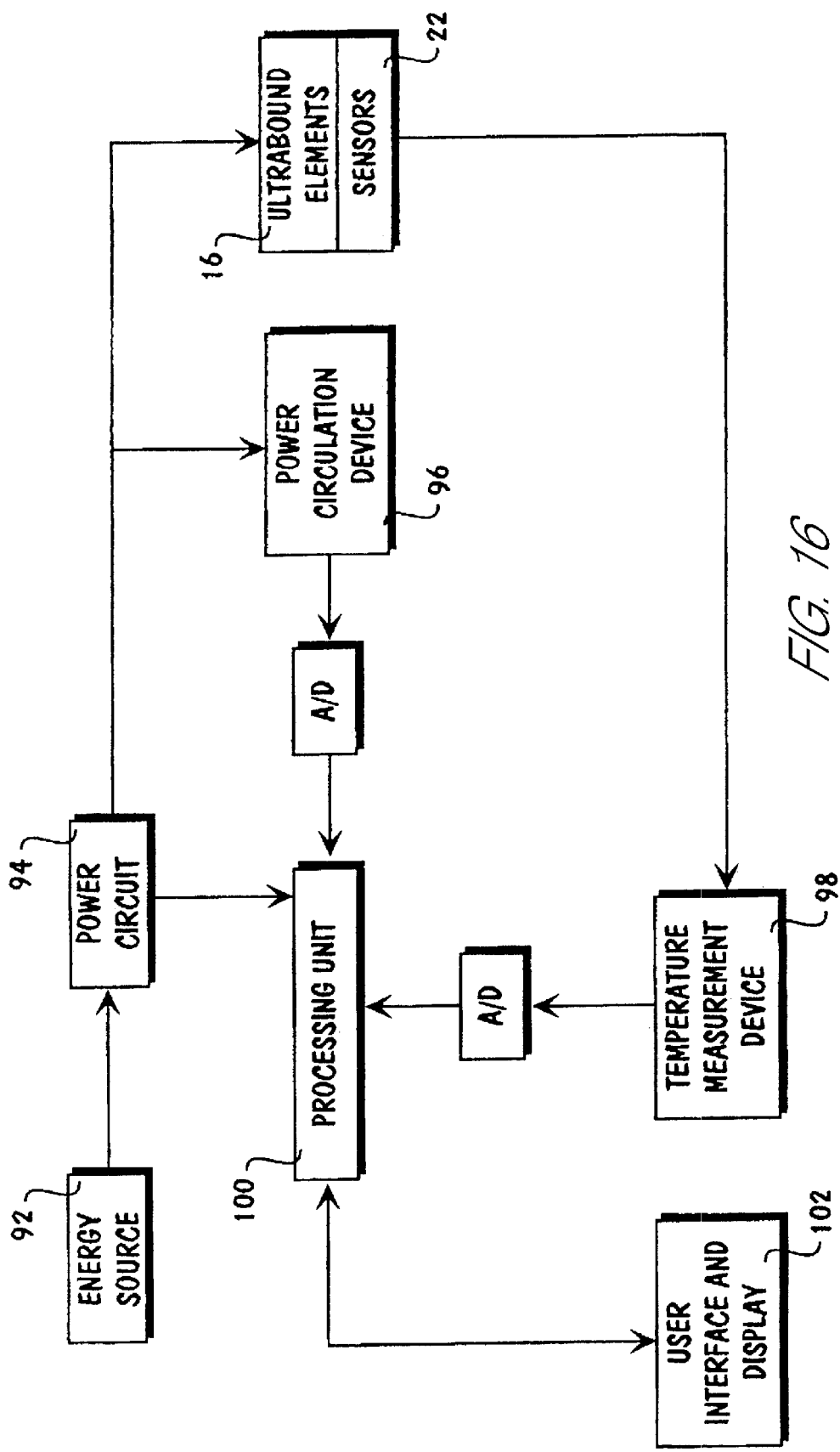
FIG. 16 illustrates a feedback control system for use with a catheter including an ultrasound assembly

The catheter 10 can be coupled with a feedback control system as illustrated in FIG. 16. The temperature at each temperature sensor 22 is monitored and the output. power of a energy source adjusted accordingly. The physician can, if desired, override the closed or open loop system.

The feedback control system includes an energy source 92, power circuits 94 and a power calculation device 96 coupled with each ultrasound transducer 20. A temperature measurement device 98 is coupled with the temperature sensors 22 on the catheter 10. A processing unit 100 is coupled with the power calculation device 96, the power circuits 94 and a user interface and display 102.

In operation, the temperature at each temperature sensor 22 is determined at the temperature measurement device 98. The processing unit 100 receive so signals indicating the determined temperatures from the temperature measurement device 98. The determined temperatures can then be displayed to the user at the user interface and display 102.

The processing unit 100 includes logic for generating a temperature control signal. The temperature control signal is proportional to the difference between the measured temperature and a desired temperature. The desired temperature can be determined by the user. The user can set the predetermined temperature at the user interface and display 102.

The temperature control signal is received by the power circuits 94. The power circuits 94 adjust the power level of the energy supplied to the ultrasound transducers 20 from the energy source 92. For instance, when the temperature control signal is above a particular level, the power supplied to a particular ultrasound transducer 20 is reduced in proportion to the magnitude of the temperature control signal. Similarly, when the temperature control signal is below a particular level, the power supplied to a particular ultrasound transducer 20 is increased in proportion to the magnitude of the temperature control signal. After each power adjustment, the processing unit 100 monitors the temperature sensors 22 and produces another temperature control signal which is received by the power circuits 94.

The processing unit 100 can also include safety control logic. The safety control logic detects when the temperature at a temperature sensor 22 has exceeded a safety threshold. The processing unit 100 can then provide a temperature control signal which causes the power circuits 94 to stop the delivery of energy from the energy source 92 to the ultrasound transducers 20.

The processing unit 100 also receives a power signal from the power calculation device 96. The power signal can be used to determine the power being received by each ultrasound transducer 20. The determined power can then be displayed to the user on the user interface and display 102.

The feedback control system can maintain the tissue adjacent to the ultrasound transducers 20 within a desired temperature range for a selected period of time. As described above, the ultrasound transducers 20 can be electrically connected so each ultrasound transducer 20 can generate an independent output. The output maintains a selected energy at each ultrasound transducer 20 for a selected length of time.

The processing unit 100 can be a digital or analog controller, or a computer with software. When the processing unit 100 is a computer it can include a CPU coupled through a system bus. The user interface and display 102 can be a mouse, keyboard, a disk drive, or other non-volatile memory systems, a display monitor, and other peripherals, as are known in the art. Also coupled to the bus is a program memory and a data memory.

In lieu of the series of power adjustments described above, a profile of the power delivered to each ultrasound transducer 20 can be incorporated in the processing unit 100 and a preset amount of energy to be delivered may also be profiled. The power delivered to each ultrasound transducer 20 can then be adjusted according to the profiles.

Figure 17A:
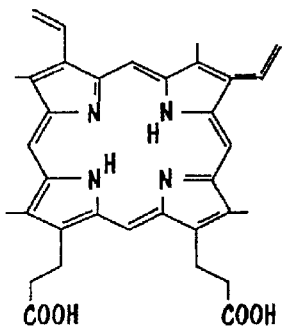
FIGS. 17A–N illustrate pyrrole-based macrocyclic classes of light emitting drugs.
Figure 17B:
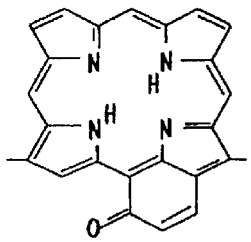
FIG. 17B-2 illustrates possible texaphyrin derivation sites.
Figure 17C:
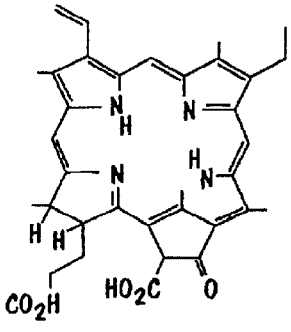
Figure 17D:
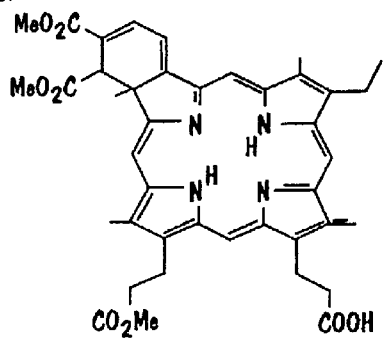
Figure 17K:
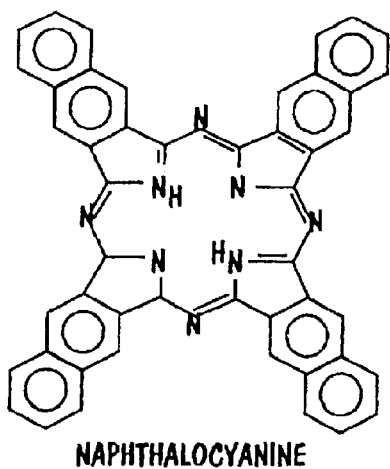
Figure 17L:
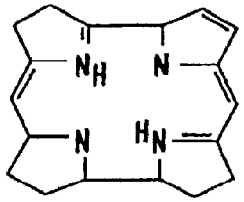
Figure 17M:
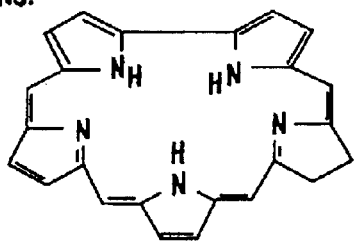
Figure 17N:
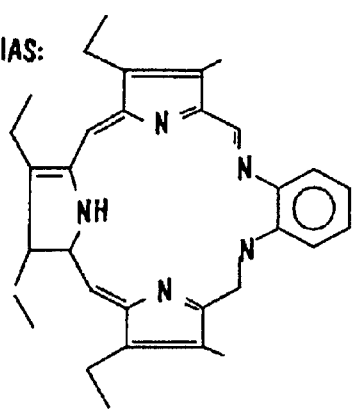

The above catheters are suitable for locally delivering a media including a light activated drug. Suitable light activated drugs include, but are not limited to, fluorescein, merocyanin. However, preferred light activated drugs include xanthene and its derivatives and the photoreactive pyrrole-derived macrocycles and their derivatives due to a reduced toxicity and an increased biological affinity. Suitable photoreactive pyrrole-derived macrocycles include, but are not limited to, naturally occurring or synthetic porphyrins, naturally occurring or synthetic chlorins, naturally occurring or synthetic bacteriochlorins, synthetic isobateriochlorins, phthalocyanines, naphtalocyanines, and expanded pyrrole-based macrocyclic systems such as porphycenes, sapphyrins, and texaphyrins. Examples of suitable pyrrole-based macrocyclic classes are illustrated in FIGS. 17A–N.

Figures 2, 17B:
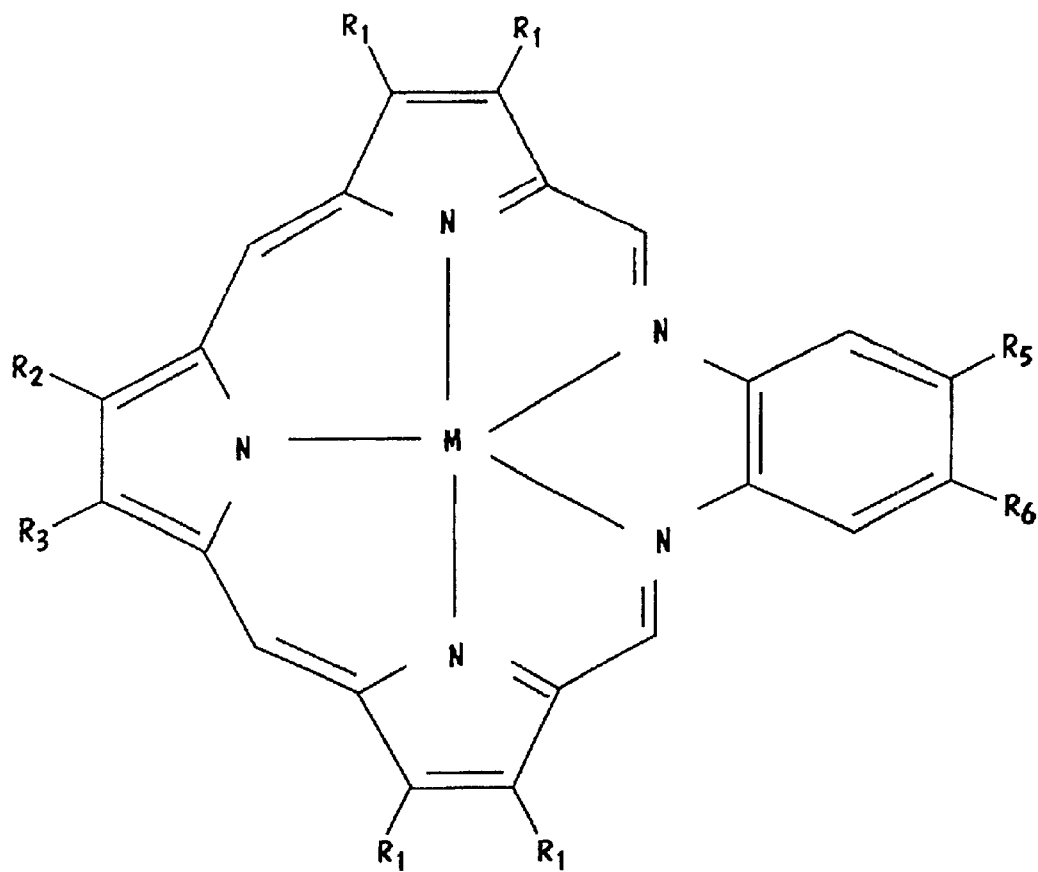
Figure 18A:
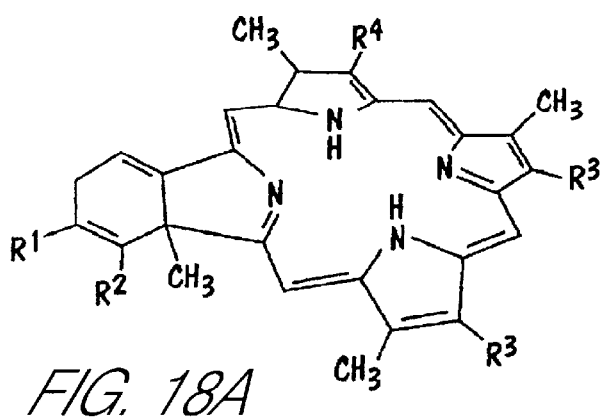
Figure 18B:
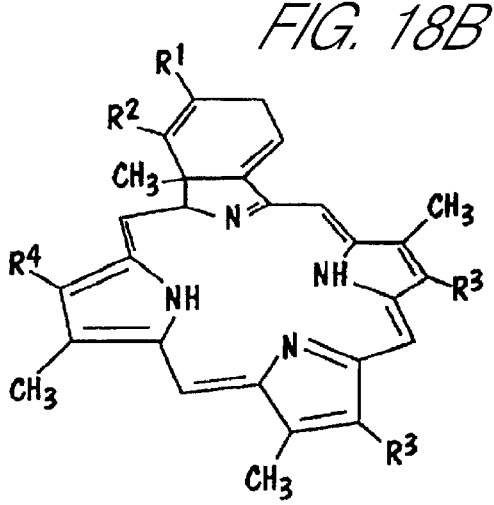
Figure 18C:
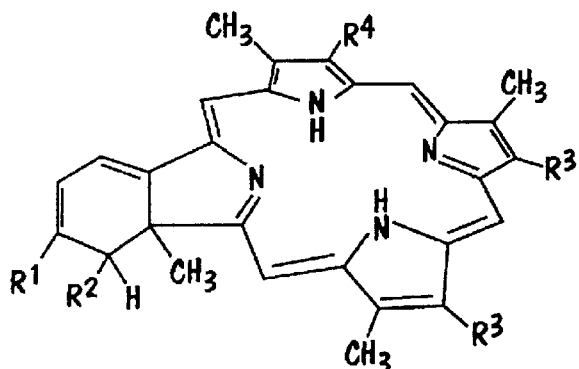
Figure 18D:
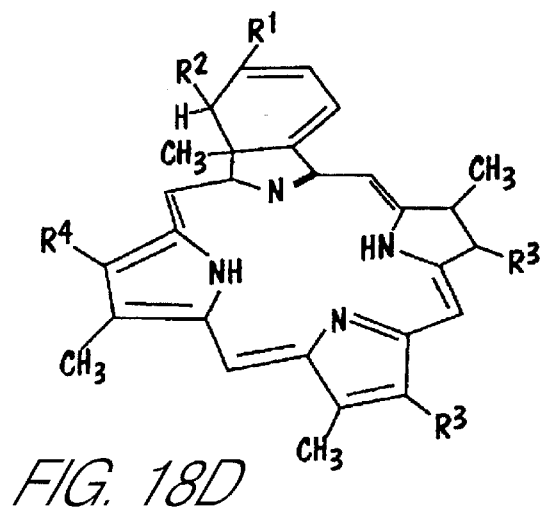

As described above, the derivative of the pyrrole-based macrocycle classes can be used. For the purposes of illustrating some of the derivatives a macrocycle class, FIG. 17B-2 illustrates a formula for the derivatives of texaphyrin: where M is H, $CH_3$, a divalent metal cation selected from the group consisting of Ca(II), Mn(II), Co(II), Ni(II), Zn(II), Cd(II), Hg(II), Fe(II), Sm(II), and UO(II) or a trivalent metal cation selected from the group consisting of Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), and U(III). Preferred metals include Lu(III), Dy(III), Eu(III), or Gd(III). M may be H or $CH_3$ in a non-metalated form of texaphyrin. $R_1$, $R_2$, $R_3$, $R_4$, $R_5$ and $R_6$ can independently be hydrogen, hydroxyl, alkyl, hydroxyalkyl, alkoxy, hydroxyalkoxy, saccharide, carboxyalkyl, carboxyamidealkyl, a site-directing molecule, or a linker to a site-directing molecule where at least one of $R_1$, $R_2$, $R_3$, $R_4$, $R_5$ and $R_6$ is hydroxyl, hydroxyalkoxy, saccharide, alkoxy, carboxyalkyl, carboxyamidealkyl, hydroxyalkyl, a site-directing molecule or a couple to a site-directing molecule; and N is an integer less than or equal to 2.

A preferred paramagnetic metal complex is the Gd(III) complex of 4,5-diethyl-10,23-dimethyl-9,24-bis(3-hydroxypropyl)-16,17-bis[2-(2-methoxyethoxy)ethoxy]ethoxy-13,20,25,26,27-pentaazapentacyclo[20.2.1.1$^{3,6}$.1$^{8,11}$.0$^{14,19}$]heptacosa-1,3,5,7,9,11 (27),12,14 (19),15,17,20,22(25),23-tridecaene ("GdT2BET") and a preferred diamagnetic metal complex is the Lu(III) complex of 4,5-diethyl-10,23-dimethyl-9,24-bis(3-hydroxypropyl)-16,17-bis[2-[2-(2-methoxyethoxy)ethoxy]ethoxy]-13,20,25,26,27-pentaazapentacyclo[20.2.1.1$^{3,6}$.1$^{8,11}$.0$^{14,19}$]heptacosa-1,3,5,7,9,11(27),12,14(19),15,17,20,22(25),23-tridecaene ("LuT2BET").

$R_1$, $R_2$, $R_3$, $R_4$, $R_6$ and may also independently be amino, carboxy, carboxamide, ester, amide sulfonato, aminoalkyl, sulfonatoalkyl, amidealkyl, aryl, etheramide or equivalent formulae conferring the desired properties. In a preferred embodiment, at least one of $R_1$, $R_2$, $R_3$, $R_4$, $R_5$ and $R_6$ is a site-directing molecule or is a couple to a site-directing molecule. For bulky R groups on the benzene ring portion of the molecule such as oligonucleotides, one skilled in the art would realize that derivatization at one position on the benzene potion is more preferred.

Hydroxyalkyl means alkyl groups having hydroxyl groups attached. Alkoxy means alkyl groups attached to an oxygen. Hydroxyalkoxy means alkyl groups having ether or ester linkages, hydroxyl groups, substituted hydroxyl groups, carboxyl groups, substituted carboxyl groups or the like. Saccharide includes oxidized, reduced or substituted saccharide; hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosacchrides, as well as open chain forms of various sugars, and the like. Examples of amine-derivatized sugars are galactosamine, glucosamine, and sialic acid. Carboxyamidealkyl means alkyl groups with secondary or tertiary amide linkages or the like. Carboxyalkyl means alkyl groups having hydroxyl groups, carboxyl or amide substituted ethers, ester linkages, tertiary amide linkages removed from the ether or the like.

For the above-described texaphyrins, hydroxyalkoxy may be alkyl having independently hydroxy substituents and ether branches or may be $C_{(n-x)}H_{((2n+1)-2x)}O_xO_y$ or $OC_{(n-x)}H_{(2n+2)-2x)}O_xO^y$ where n is a positive integer from 1 to 10, x is zero or a positive integer less than or equal to n, and y is zero or a positive integer less than or equal to $((2n+1)-2x)$. The hydroxyalkoxy or saccharide may be $C_nH_{((2n+1)-q)}O_yR^a_q$, $OC_nH_{(2n+1)-q)}O_yR^a_q$ or $(CH_2)_nCO_2R^a$ where n is a positive integer from 1 to 10, y is zero or a positive integer less than $((2n+1)-q)$, q is zero or a positive integer less than or equal to 2n+1, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$. In this case, m is a positive integer from 1 to 10, w is zero or a positive integer less than or equal to m, z is zero or a positive integer less than or equal to $((2m+1)-2w)$, and R is H, alkyl, hydroxyalkyl, or $C_mH_{(2m+1)-r)}O_zR^b_r$ where m is a positive integer from 1 to 10, z is zero or a positive integer less than $((2m+1)-r)$, r is zero or a positive integer less than or equal to 2m+1, and $R^b$ is independently H, alkyl, hydroxyalkyl, or saccharide.

Carboxyamidealkyl may be alkyl having secondary or tertiary amide linkages or $(CH_2)_nCONHR^a$, $O(CH_2)_nCONHR^a$, $(CH_2)_nCON(R^a)2$, or $O(CH_2)_nCON(R^a)2$ where n is a positive integer from 1 to 10, and R is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$, $N(R)OCC_{(m-w)}H_{((2m+1)-2w)}O_wO_z$, or site-directing molecule. In this case, m is a positive integer from 1 to 10, w is zero or a positive integer less than or equal to $((2M+1)-2w)$, and R is H, alkyl, hydroxyalkyl, or $C_mH_{((2m+1)-r)}O_zR^b_r$. In this case, m is a positive integer from 1 to 10, w is zero or a positive integer less than or equal to m, z is zero or a positive integer less than or equal to $((2M+1)-r)$, r is zero or a positive integer less than or equal to 2m+1, and $R^b$ is independently H, alkyl, hydroxyalkyl, or saccharide. In a preferred embodiment, $R^a$ is an oligonucleotide.

Carboxyalkyl may be alkyl having a carboxyl substituted ether, an amide substituted ether or a tertiary amide removed from an ether or $C_nH_{(2n+1)-q)}O_yR^c_q$ or $OC_nH_{(2n+1))-q)}O_yR^e_q$ where n is a positive integer from 1 to 10; y is zero or a positive integer less than $((2n+1)-q)$, q is zero or a positive integer less than or equal to 2n+1, and $R^c$ is $(CH_2)_nCO_2R^d$, $(CH_2)_nCOHR^d$, $(CH_2)_nCON(R^d)_2$ or a site-directing molecule. In this case, n is a positive integer from 1 to 10, $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{(2m+1)-2w)}O_wO_z$. In this case, m is a positive integer from 1 to 10, z is zero or a positive integer less than $((2m+1)-2w)$, and R is H, alkyl, hydroxyalkyl, or $C_mH_{((2m+1)-r)}O_zR^b_r$. In this case, m is a positive integer from 1 to 10, z is zero or a positive integer less than $((2m+1)-r)$, r is zero or a positive integer less than or equal to 2M+1, and $R^b$ is independently H, alkyl, hydroxyalkyl, or saccharide. In a preferred embodiment, $R^c$ is an oligonucleotide.

Exemplary texaphyrins are listed in Table 1.

TABLE 1

Representative Substitutes for Texaphyrin Macrocycles

| TXP | $R_1$ | $R_2$ | $R_3$ | $R_4$ | $R_5$ | $R_6$ |
|---|---|---|---|---|---|---|
| A1 | $CH_2(CH_2)_2OH$ | $CH_2H_3$ | $CH_2CH_3$ | $CH_3$ | $O(CH_2)_3OH$ | $O(CH2)3OH$ |
| A2 | " | " | " | " | $O(CH_2CH_2O)_3CH_3$ | $O(CH_2CH_2O)_3CH_3$ |
| A3 | " | " | " | " | $O(CH_2)_nCON$—linker-site-directing molecule, n = 1–7 | " |
| A4 | " | " | " | " | $O(CH_2)_nCON$—linker-site-directing molecule | H |
| A5 | " | " | " | " | $OCH_2CO$-hormone | " |
| A6 | " | " | " | " | $O(CH_2CH_2O)_3CH_3$ | " |
| A7 | " | " | " | " | $OCH_2CON$-linker-site-directing molecule | $O(CH_2CH_2O)_3CH_3$ |
| A8 | " | " | " | " | $OCH_2CO$-hormone | " |
| A9 | " | " | " | " | $O(CH_2CH_2O)_{120}CH_3$ | $O(CH_2CH_2O)_3CH_2$—$CH_2$—N-imidazole |
| A10 | " | " | " | " | saccharide | H |
| A11 | " | " | " | " | $OCH_2CON$—$(CH_2CH_2OH)_2$ | " |
| A12 | " | " | " | " | $CH_2CON(CH_3)CH_2$—$(CHOH)_4CH_2OH$ | " |
| A13 | " | COOH | COOH | " | $CH_2CON(CH_3)CH_2$—$(CHOH)_4CH_2OH$ | " |
| A14 | " | $COOCH_2CH_3$ | $COOCH_2CH_3$ | " | $CH_2CON(CH_3)CH_2$—$(CHOH)_4CH_2OH$ | " |

TABLE 1-continued

Representative Substitutes for Texaphyrin Macrocycles

| TXP | $R_1$ | $R_2$ | $R_3$ | $R_4$ | $R_5$ | $R_6$ |
|---|---|---|---|---|---|---|
| A15 | $Ch_2CH_2CON(CH_2CH_2OH)_2$ | $CH_2H_3$ | $CH_2CH_3$ | " | $CH_2CON(CH_2)CH_2$—$(CHOH)_4CH_2OH$ | " |
| A16 | $CH_3CH_2ON(CH_3)CH_2$—$(CHOH)_4CH_2OH$ | " | " | " | $OCH_3$ | $OCH_3$ |
| A17 | $CH_2(CH_2)_2OH$ | " | " | " | $O(CH_2)_nCOOH$, n = 1–7 | H |
| A18 | " | " | " | " | $(CH_2)_n$—CON—linker-site-directing molecule, n = 1–7 | " |
| A19 | " | " | " | " | $YCOCH_2$-linker-site-directing molecule Y = NH, O | " |
| A20 | $CH_2H_3$ | | $CH_3$ | $CH_2CH_2COOH$ | " | $O(CH_2)_2CH_2OH$ | $O(CH_2)_2CH_2OH$ |
| A21 | " | | " | $CH_2CH_2CON$-oligo | " | " | " |
| A22 | $CH_2(CH_2)_2OH$ | $CH_2CH_3$ | $CH_2CH_3$ | " | $O(CH_2)_2CO$-histamine | H |

Preferred pyrrole-based macrocycles include, but are not limited to the hydro-monobenzoporphyrins (the so-called "fi porphyrine" or "Gp" compounds) disclosed in U.S. Pat. Nos. 4,920,143 and 4,883,790 which are incorporated herein by reference. Typically, these compounds are poorly water-soluble (less than 1 mg/ml) or water-insoluble. Gp is preferably selected from the group consisting of those compounds having one of the formulae A–F set forth in FIGS. 18A–F, mixtures thereof, and the metalated and labeled forms thereof.

In FIGS. 18A–F, $R^1$ and $R^2$ can be independently selected from the group consisting of carbalkoxy (2–6C), alkyl (1–6C) sulfonyl, aryl (6–10C), sulfonyl, aryl (6–10C), cyano, and —$CONR^5CO$— wherein $R^5$ is aryl (6–10C) or alkyl (1–6C). Preferably, however, each of $R^1$ and $R^2$ is carbalkoxy (2–6C). $R^3$ can be independently carboxyalkyl (2–6C) or a salt, amide, ester or acylhydrazone thereof, or is alkyl (1–6C). Preferably $R^3$ is —$CH^2CH^2COOH$ or a salt, amide, ester or acylhydrazone thereof.

$R^4$ is —$CHCH_2$; —$CHOR^{4'}$ wherein $R^{4'}$ is H or alkyl (1–6C), optionally substituted with a hydrophilic substituent; —CHO; —$COOR^{4'}$; $CH(OR^{4'})CH_3$; $CH(OR^{4'})CH_2OR^{4'}$; —$(SR^")CH_3$; —$CHNR^{4'}{}_2)CH_3$; —$CH(CN)CH_3$; —$CH(COOR^{4'})CH_3$; —$CH(OOCR^{4'})CH_3$; $CH(halo)CH_3$; —$CH(halo)CH_2(halo)$; an organic group of <12C resulting from direct or indirect derivatization of a vinyl group; or $R^4$ consists of 1–3 tetrapyrrole-type nuclei of the formula —L—P, wherein —L— is selected from the group consisting of

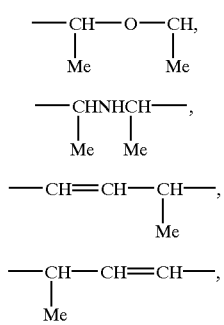

(a), (b), (c), (d), (e), (f)

Figure 19:
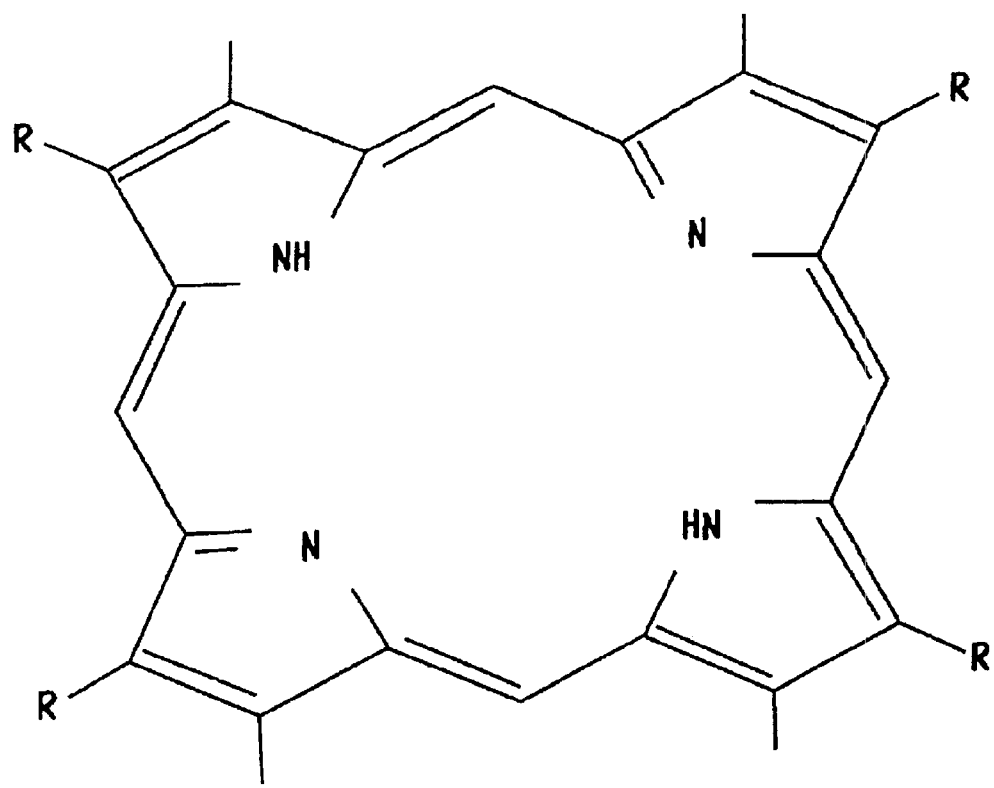
FIG. 19 illustrates a formula for a porphyrin group.
Figure 20A:
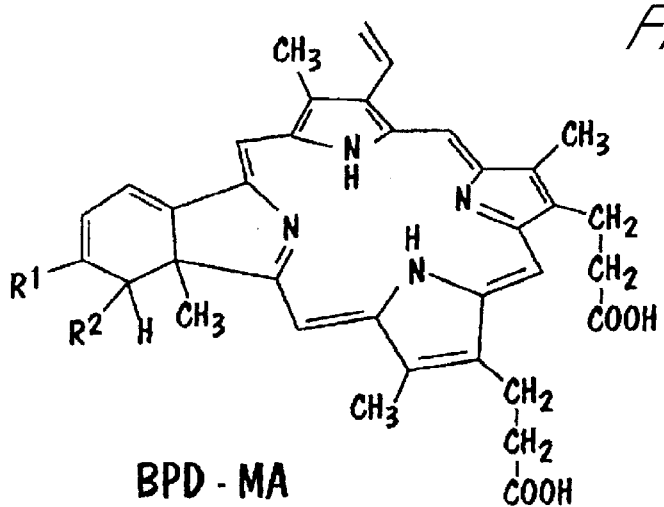
Figure 20B:
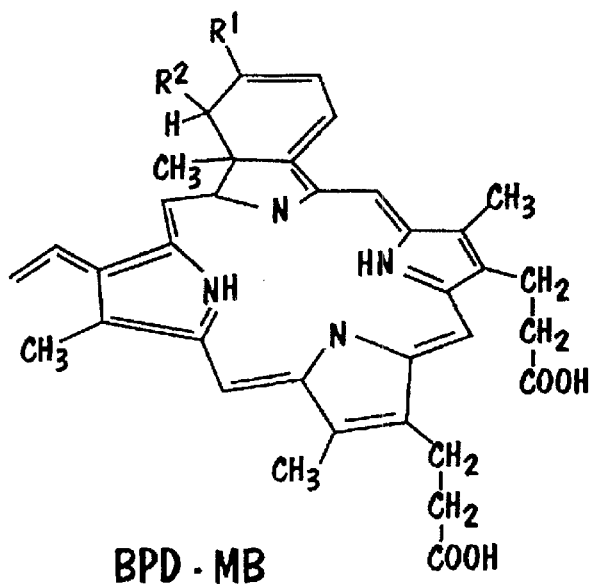

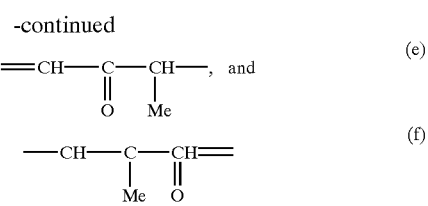

and P is a second Gp, which is one of the formulae A–F (FIG. 18) but lacks $R^4$, or another porphyrin group. When P is another porphyrin group, P preferably has the formula illustrated in FIG. 19: wherein each R is independently H or lower alkyl (1–4C); two of the four bonds shown as unoccupied on adjacent rings are joined to $R^3$; one of the remaining bonds shown as unoccupied is joined to $R^4$; and the other is joined to L; with the proviso that if $R^4$ is —$CHCH_2$, both $R^3$ groups cannot be carbalkoxyethyl. The preparation and use of such compounds is disclosed in U.S. Pat. Nos. 4,920,143 and 4,883,790, which are hereby incorporated by reference.

Even more preferred for including in liposomes are light activated drugs that are designated as benzoporphyrin derivatives ("BPD's"). BPD's are hydrolyzed forms, or partially hydrolyzed forms, of the rearranged products of formula A–C or formula A–D, where one or both of the protected carboxyl groups of $R^3$ are hydrolyzed. Particularly preferred is the compound referred to as BPD-MA in FIGS. 20A–D, which has two equally active regioisomers.

Figure 21B:
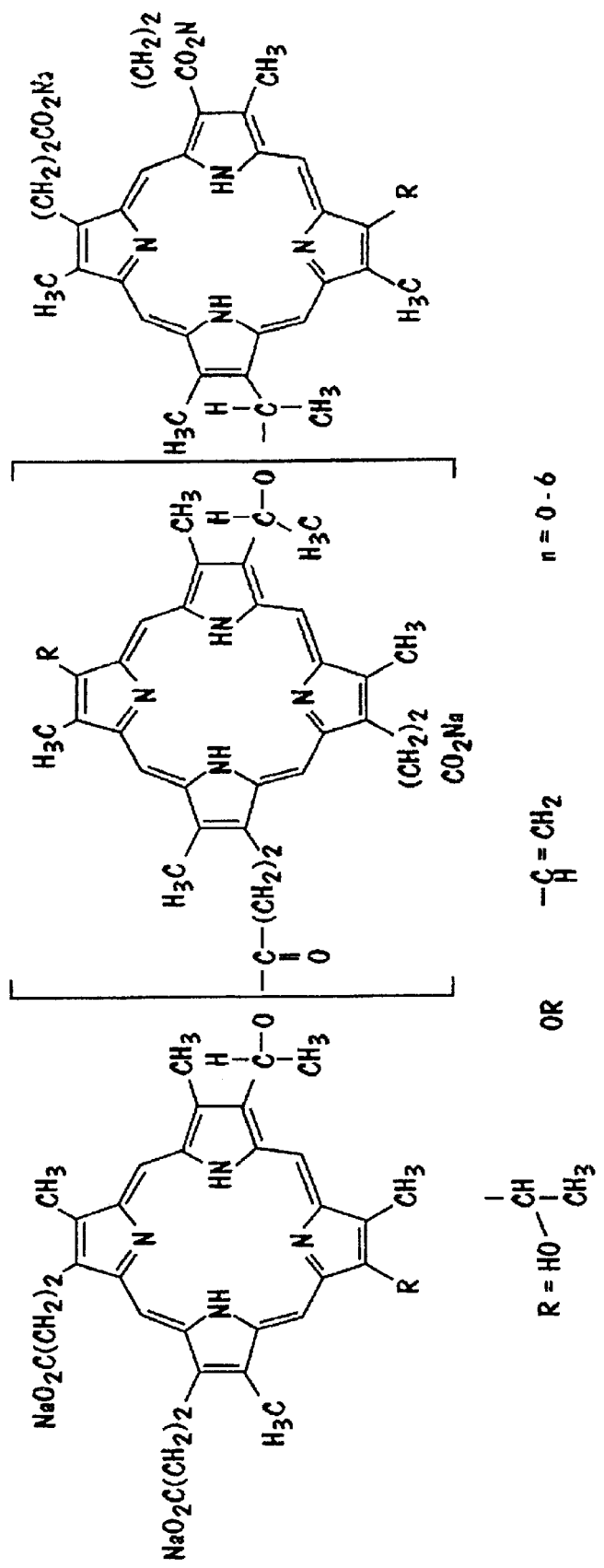

As described above, activating a light activated drug included in a microbubble can enhance rupture of the microbubble. Preferred light activated drugs for including in a microbubble to enhance rupture of the microbubble include Hematporphyrin, Rose Bengal, Eosin Y, Erythrocin, Rhodamine B, and PHOTOFRIN. The formulae for these preferred light activated drugs are illustrated in FIGS. 21A–B where Rose Bengal, Eosin Y, Erythrocin and Rhodamine B are xanthene derivatives.

As discussed above, the light activated drug can be coupled with a site directing molecule to form a light activated drug conjugate. Suitable site-directing molecules include, but are not limited to: polydeoxyribonucleotides, oligodeoxyribonucleotides, polyribonucleotide analogs, oligoribonucleotide analogs; polyamides including peptides having an affinity for a biological receptor and proteins such as antibodies; steroids and steroid derivatives; hormones such as estradiol or histamine; hormone mimics such as morphine and further macrocycles such as sapphyrins and rubyrins. It is understood that the terms "nucleotide", "polynucleotide", and "oligonucleotide", as used herein and in the appended claims, refer to both naturally occurring and synthetic nucleotides, poly- and oligonucleotides and to analogs and derivatives thereof such as methylphosphonates, phosphotriesters, phosphorothioates, and phosphoramidates and the like. Deoxyribonucleotides and ribonucleotide analogs are contemplated as site-directing molecules.

When the site-directing molecule is an oligonucleotide, the oligonucleotide may be derivatized at the bases, the sugars, the end of the chains, or at the phosphate groups of the backbone to promote in vivo stability. Modifications of the phosphate groups are preferred in one embodiment since phosphate linkages are sensitive to nuclease activity. Preferred derivatives are the methylphosphonates, phosphotriesters, phosphorothioates, and phosphoramidates. Additionally, the phosphate linkages may be completely substituted with non-phosphate linkages such as amide linkages. Appendages to the ends of the oligonucleotide chains also provide exonuclease resistance. Sugar modifications may include alkyl groups attached to an oxygen of a ribose moiety in a ribonucleotide. In particular, the alkyl group is preferably a methyl group and the methyl group is attached to the 2' oxygen of the ribose. Other alkyl groups may be ethyl or propyl.

A linker may be used to couple the light activated drug with the site directing molecule. Exemplary linkers include, but are not limited to, amides, amine, thioether, ether, or phosphate covalent bonds as described in the examples for attachment of oligonucleotides. In a preferred embodiment, an oligonucleotide or other site-directing molecules is covalently bonded to a texaphyrin or other light activated drugs via a carbon-nitrogen, carbon-sulfur, or a carbon-oxygen bond.

As described above, the media can be an emulsion which includes a light activated drug. The emulsions described below are suitable for delivery into a body since they avoid pharmaceutically undesirable organic solvents, solubilizers, oils or emulsifiers. A wide range of light activated drug concentrations can be used in the emulsion. Suitable concentrations of light activated drug within the emulsion include, but are not limited to, approximately 0.01 to 1 gram/100 ml, preferably about 0.05 to about 0.5 gram/100 ml, and approximately 0.1 g/100 ml.

The emulsion includes a lipoid as a hydrophobic component dispersed in a hydrophilic phase. The hydrophobic component of the emulsion comprises a pharmaceutically acceptable triglyceride, such as an oil or fat of a vegetable or animal nature, and preferably is selected from the group consisting of soybean oil, safflower oil, marine oil, black current seed oil, borage oil, palm kernel oil, cotton seed oil, corn oil, sunflower seed oil, olive oil or coconut oil. Physical mixtures of oils and/or interesterfied mixtures can be employed. The preferred oils are medium chain length triglycerides having $C_8$–$C_{10}$ chain length and more preferably saturated. The preferred triglyceride is a distillate obtained from coconut oil. The hydrophobic content of the emulsion is preferably approximately 5 to 50 g/100 ml, more preferably about 10 to about 30 g/100 ml and approximately 20 g/100 ml of the emulsion.

The emulsion can also contains a stabilizer such as phosphatides, soybean phospholipids, nonionic block copolymers of polyoxethylene and polyoxpropylene (e.g. poloxamers), synthetic or semi-synthetic phospholipids, and the like. The preferred stabilizer is purified egg yolk phospholipid. The stabilizer is usually present in the composition in amounts of about 0.1 to about 10, and preferably about 0.3 to about 3 grams/100 ml, a typical example being about 1.5 grams/100 ml.

The emulsion can also include one or more bile acids salts as a costablizer. The salts are pharmacologically acceptable salts of bile acids selected from the group of cholic acid, deoxycholic acid and gylcocholic acid, and preferably of cholic acid. The salts are typically alkaline metal or alkaline earth metal salts and preferably sodium, potassium, calcium or magnesium salts, and most preferably, sodium salts. Mixtures of bile acid salts can be employed if desired. The amount of bile acid salt employed is usually about 0.01 to about 1.0 and preferably about 0.05 to about 0.4 grams/100 ml, a typical example being about 0.2 grams/100 ml.

Suitable pH for the emulsion includes, but is not limited to approximately 7.5 to 9.5, and preferably approximately 8.5. The pH can be adjusted to the desired value, if necessary, by adding a pharmaceutically acceptable base, such as sodium hydroxide, potassium hydroxide, calcium hydroxide, magnesium hydroxide and ammonium hydroxide.

Water can be added to the emulsion to achieve the desired concentration of various components within the emulsion. Further, the emulsion can include auxiliary ingredients for regulating the osmotic pressure to make the emulsion isotonic with the blood. Suitable auxiliary ingredients include, but are not limited to, auxiliary surfactants, isotonic agents, antioxidants, nutritive agents, trace elements and vitamins. Suitable isotonic agents include, but are not limited to, glycerin, amino acids, such as alanine, histidine, glycine, and/or sugar alcohols, such as xylitol, sorbitol and/or mannitol. Suitable concentrations for isotonic agents within the emulsion include, but are not limited to, approximately 0.2 to about 8.0 grams/100 ml and preferably about 0.4 to about 4 grams/100 ml and most preferably 1.5 to 2.5 gram/100 ml.

Antioxidants can be used to enhance the stability of the emulsion, a typical example being α-tocopherol. Suitable concentrations for the antioxidants include, but are not limited to approximately 0.005 to 0.5 grams/100 ml, approximately 0.02 to about 0.2 grams/100 ml and most preferably approximately 0.05 to 0.15 grams/100 ml.

The emulsions can also contain auxiliary solvents, such as an alcohol, such as ethyl alcohol or benzyl alcohol, with ethyl alcohol being preferred. When employed, such is typically present in amounts of about 0.1 to about 4.0, and preferably about 0.2 to about 2 grams/100 ml, a typical example being about 1 gram/100 ml. The ethanol is advantageous since it facilitates dissolution of poorly water-soluble light activated drugs and especially those that form crystals which may be very difficult to dissolve in the hydrophobic phase. Accordingly, the ethanol must be added directly to the hydrophobic phase during preparation to be effective. For maximum effectiveness, the ethanol should constitute about 5% to 15% by weight of the hydrophobic phase. In particular, if ethanol constitutes less than 5% by weight of the hydrophobic phase, dissolution of the light activated drug can become unacceptably slow. When the ethanol concentration exceeds 15%, large (>5 μm diameter) and poorly emulsified oil droplets can form in the emulsion. The particles in the emulsion are preferably less than about 5.0 μm in diameter, more preferably less than 2.0 μm in diameter and most preferably less than 0.5 μm or below.

A typical emulsion is prepared using the following technique. The triglyceride oil is heated to 50°–70° C. while sparging with nitrogen gas. The required amounts of stabilizer (e.g. egg yolk phospholipids), bile acid salt, alcohol (e.g. ethanol), antioxidant (e.g. α-to-copherol) and light activated drug are added to the triglyceride while processing for about 5 to about 20 minutes with a high speed blender or overhead mixer to ensure complete dissolution or uniform suspension.

In a separate vessel, the required amounts of water and isotonic agent (e.g.-glycerin) are heated to the above temperature (e.g. 50°–70°) while sparging with nitrogen gas. Next, the aqueous phase is transferred into the prepared hydrophobic phase and high speed blending is continued for another 5 to 10 minutes to produce a uniform but coarse preemulsion (or premix). This premix is then transferred to a conventional high pressure homogenizer (APV Gaulin) for emulsification at about 8,000–10,000 psi. The diameter of the dispersed oil droplets in the finished emulsion will be less than 5 µm, with a large proportion less than 1 µm. The mean diameter of these oil droplets will be less than 1 µm, preferably from 0.2 to 0.5 µm. The emulsion product is then filled into borosilicate (Type 1) glass vials which are stoppered, capped and terminally heat sterilized in a rotating steam autoclave at about 121° C.

These emulsions can withstanding autoclaving as well as freezing at about 0° to −20° C. Such can be stored for a relatively long time with minimal physical and chemical breakdown, i.e. at least 12–18 months at 4°–8° C. The vehicle composition employed is chemically inert with respect to the incorporated pharmacologically active light activated drug.

The emulsions can exhibit very low toxicity following intravenous administration and exhibit no venous irritation and no pain on injection. The emulsions exhibit minimal physical and chemical changes (e.e. formation of non-emulsified surface oil) during controlled shake-testing on a horizontal platform. Moreover, the oil-in-water emulsions promote desirable pharmacoldnetics and tissue distribution of the light activated drug in vivo.

As discussed above, the light activated drug can also be delivered to the body in a media which includes microbubbles. Suitable substrates for the microbubble include, but are not limited to, biocompatible polymers, albumins, lipids, sugars or other substances. U.S. Pat. Nos. 5,701,899 and 5,578,291 teaches a method for synthesizing microbubbles with a sugar and protein substrate and is incorporated herein by reference. U.S. Pat. Nos. 5,665,383 and 5,665, 382 teaches a method for synthesizing microbubbles with a polymeric substrate and is incorporated herein by reference. U.S. Pat. Nos. 5,626,833 and 5,798,091 teach methods for synthesizing microbubbles with a surfactant substrate and are incorporated herein by reference. A preferred microbubble has a lipid substrate. U.S. Pat. Nos. 5,772,929 teaches methods for synthesizing microbubbles with a lipid substrate. U.S. Pat. Nos. 5,776,429, 5,715,824 and 5,770,222 teach preferred methods for synthesizing microbubbles with a lipid substrate and a gas interior and are incorporated herein by reference.

Suitable microbubbles with a lipid substrate can be liposomes. The liposomes can be unilamellar vesicles having a single membrane bilayer or multilamellar vesicles having multiple membrane bilayers, each bilayer being separated from the next by an aqueous layer. A liposome bilayer is composed of two lipid monolayers having a hydrophobic "tail" region and a hydrophilic "head" region. The formula of the membrane bilayer is such that the hydrophobic (nonpolar) "tails" of the lipid monolayers orient themselves towards the center of the bilayer, while the hydrophilic "heads" orient themselves toward the aqueous phase. Either unilamellar or multilamellar or other types of liposomes may be used.

A hydrophilic light activated drug can be entrapped in the aqueous phase of the liposome before the drug is delivered into the patient. Alternatively, if the light activated drug is lipophilic, it may associate with the lipid bilayer. Liposomes may be used to help "target" the light activated drug to an active site or to solubilize hydrophobic light activated drugs. Light activated drugs are typically hydrophobic and form stable drug-lipid complexes.

As discussed above, many light activated drugs have low solubility in water at physiological pH's, but are also insoluble in (1) pharmaceutically acceptable aqueous-organic co-solvents, (2) aqueous polymeric solutions and (3) surfactant/micellar solutions. However, such light activated drugs can still be "solubilized" in a form suitable for delivery into a body by using a liposome composition. For example, one example of a light activated drug BPD-MA (See Formula A of FIG. 20) can be "solubilized" at a concentration of about 2.0 mg/ml in aqueous solution using an appropriate mixture of phospholipids to form encapsulating liposomes.

Although the light activated drug can be included in many different types of liposomes, the following description discloses particular liposome compositions and methods for making the liposomes which are known to be "fast breaking". In fast breaking liposomes, the light activated drug-liposome combination is stable in vitro but, when administered in vivo, the light activated drug is rapidly released into the bloodstream where it can associate with serum lipoproteins. As a result, the localized delivery of liposomes combined with the fast breaking nature of the liposomes can result in localization of the light activated drug in the tissues near the catheter. Further, the fast breaking liposomes can prevent the liposomes from leaving the vicinity of the catheter intact and then concentrating in non-targeted tissues such as the liver. Delivery of ultrasound energy from the catheter can also serve to break apart the liposomes after they have been delivered from the catheter.

Liposomes are typically formed spontaneously by adding water to a dry lipid film. Liposomes which include light activated drugs can include a mixture of the commonly encountered lipids dimyristoyl phosphatidyl choline ("DMPC") and egg phosphatidyl glycerol ("EPG"). The presence of DMPC is important because DMPC is the major component in the composition to form liposomes which can solubilize and encapsulate insoluble light activated drugs into a lipid bilayer. The presence of EPG is important because the negatively charged, polar head group of this lipid can prevent aggregation of the liposomes.

Other phospholipids, in addition to DMPC and EPG, may also be present. Examples of suitable additional phospholipids that may also be incorporated into the liposomes include phosphatidyl cholines (PCS), including mixtures of dipalmitoyl phosphatidyl choline (DPPC) and distearoyl phosphatidyl choline (DSPC). Examples of suitable phosphatidyl glycerols (PGs) include dimyristoyl phosphatidyl glycerol (DMPG), DLPG and the like.

Other types of suitable lipids that may be included are phosphatidyl ethanolamines (PEs), phosphatidic acids (PAs), phosphatidyl serines, and phosphatidyl inositols.

The molar ratio of the light activated drug to the DMPC/EPG phospholipid mixture can be as low as 1:7.0 or may contain a higher proportion of phospholipid, such as 1:7.5. Preferably, this molar ratio is 1:8 or more phospholipid, such as 1:10, 1:15, or 1:20. This molar ratio depends upon the exact light activated drug being used, but will assure the presence of a sufficient number of DMPC and EPG lipid molecules to form a stable complex with many light activated drugs. When the number of lipid molecules is not sufficient to form a stable complex, the lipophilic phase of the lipid bilayer becomes saturated with light activated drug molecules. Then, any slight change in the process conditions can force some of the previously encapsulated light activated drug to leak out of the vesicle, onto the surface of the lipid bilayer, or even out into the aqueous phase.

If the concentration of light activated drug is high enough, it can actually precipitate out from the aqueous layer and promote aggregation of the liposomes. The more unencapsulated light activated drug that is present, the higher the degree of aggregation. The more aggregation, the larger the mean particle size will be, and the more difficult aseptic or sterile filtration will be. As a result, small changes in the molar ratio can be important in achieving proper filterability of the liposome composition.

Accordingly, slight increases in the lipid content can increase significantly the filterability of the liposome composition by increasing the ability to form and maintain small particles. This is particularly advantageous when working with significant volumes of 500 ml, a liter, five liters, 40 liters, or more, as opposed to smaller batches of about 100–500 ml or less. This volume effect is thought to occur because larger homogenizing devices tend to provide less efficient agitation than can be accomplished easily on a small scale. For example, a large size Microfluidizer™ has a less efficient interaction chamber than that one of a smaller size.

A molar ratio of 1.05:3:5 BPD-MA:EPG:DMPC (i.e., slightly less phospholipid than 1:8.0 light activated drug:phospholipid) may provide marginally acceptable filterability in small batches of up to 500 ml. However, when larger volumes of the composition are being made, a higher molar ratio of phospholipid provides more assurance of reliable aseptic filterability. Moreover, the substantial potency losses that are common in scale-up batches, due at least in part to filterability problems, can thus be avoided.

Any cryoprotective agent known to be useful in the art of preparing freeze-dried formulations, such as di- or polysaccharides or other bulking agents such as lysine, may be used. Further, isotonic agents typically added to maintain isomolarity with body fluids may be used. In a preferred embodiment, a di-saccharide or polysaccharide is used and functions both as a cryoprotective agent and as an isotonic agent.

In a particular embodiment, the particular combination of the phospholipids, DMPC and EPG, and a disaccharide or polysaccharide form a liposomal composition having liposomes of a particularly narrow particle size distribution. When the process of hydrating a lipid film is prolonged, larger liposomes tend to be formed, or the light activated drug can even begin to precipitate. The addition of a disaccharide or polysaccharide provides instantaneous hydration and the large surface area for depositing a thin film of the drug-phospholipid complex. This thin film provides for faster hydration so that, when the liposome is initially formed by adding the aqueous phase, the liposomes formed are of a smaller and more uniform particle size. This provides significant advantages in terms of manufacturing ease.

However, it is also possible that, when a saccharide is present in the composition, it is added after dry lipid film formation, as a part of the aqueous solution used in hydration. In a particularly preferred embodiment, a saccharide is added to the dry lipid film during hydration.

Disaccharides or polysaccharides are preferred to monosaccharides for this purpose. To keep the osmotic pressure of the liposome composition similar to that of blood, no more than 4–5% monosaccharides could be added. In contrast, about 9–10% of a disaccharide can be used without generating an unacceptable osmotic pressure. The higher amount of disaccharide provides for a larger surface area, which results in smaller particle sizes being formed during hydration of the lipid film.

Accordingly, the preferred liposomal composition comprises a disaccharide or polysaccharide, in addition to the light activated drug and the mixture of DMPC and EPG phospholipids. When present, the disaccharide or polysaccharide is preferably chosen from among the group consisting of lactose, trehalose, maltose, maltotriose, palatinose, lactulose or sucrose, with lactose or trehalose being preferred. Even more preferably, the liposomes comprise lactose or trehalose.

Also, when present, the disaccharide or polysaccharide is formulated in a preferred ratio of about 10–20 saccharide to 0.5–6.0 DMPC/EPG phospholipid mixture, respectively, even more preferably at a ratio from about 10 to 1.5–4.0. In one embodiment, a preferred but not limiting formulation is lactose or trehalose and a mixture of DMPC and EPG in a concentration ratio of about 10 to 0.94–1.88 to about 0.65–1.30, respectively.

The presence of the disaccharide or polysaccharide in the composition not only tends to yield liposomes having extremely small and narrow particle size ranges, but also provides a liposome composition in which light activated drugs, in a particular, may be stably incorporated in an efficient manner, i.e., with an encapsulation efficiency approaching 80–100%. Moreover, liposomes made with a saccharide typically exhibit improved physical and chemical stability, such that they can retain an incorporated light activated drug without leakage upon prolonged storage, either as a reconstituted liposomal or as a cryodesiccated powder.

Other optional ingredients include minor amounts of nontoxic, auxiliary substances in the liposomal composition, such as antioxidants, e.g., butylated hydroxytoluene, alphatocopherol and ascorbyl palmitate; pH buggering, agents e.g., phosphates, glycine, and the like.

Liposomes containing a light activated drug may be prepared by combining the light activated drug and the DMPC and EPG phospholipids (and any other optional phospholipids or excipients, such as antioxidants) in the presence of an organic solvent. Suitable organic solvents include any volatile organic solvent, such as diethyl ether, acetone, methylene chloride, chloroform, piperidine, piperidine-water mixtures, methanol, tert-butanol, dimethyl sulfoxide, N-methyl-2-pyrrolidone, and mixtures thereof. Preferably, the organic solvent is water-immiscible, such as methylene chloride, but water immiscibility is not required. In any event, the solvent chosen should not only be able to dissolve all of the components of the lipid film, but should also not react with, or otherwise deleteriously affect, these components to any significant degree.

The organic solvent is then removed from the resulting solution to form a dry lipid film by any known laboratory technique that is not deleterious to the dry lipid film and the light activated drug. Preferably, the solvent is removed by placing the solution under a vacuum until the organic solvent is evaporated. The solid residue is the dry lipid film. The thickness of the lipid film is not critical, but usually varies from about 30 to about 45 mg/cm$^2$, depending upon the amount of solid residual and the total area of the glass wall of the flask. Once formed, the film may be stored for an extended period of time, preferably not more than 4 to 21 days, prior to hydration. While the temperature during a lipid film storage period is also not an important factor, it is preferably below room temperature, most preferably in the range from about −20 to about 4° C.

The dry lipid film is then dispersed in an aqueous solution, preferably containing a disaccharide or polysaccharide, and homogenized to form the desired particle size. Examples of useful aqueous solutions used during the hydration step include sterile water, a calcium- and magnesium-free, phosphate-buffered (pH 7.2–7.4) sodium chloride solution; a 9.75% w/v lactose solution; a lactose-saline solution; 5% dextrose solution; or any other physiologically acceptable aqueous solution of one or more electrolytes. Preferably, however, the aqueous solution is sterile. The volume of aqueous solution used during hydration can vary greatly, but should not be so great as about 98% nor so small as about 30–40%. A typical range of useful volumes would be from about 75% to about 95%, preferably about 85% to about 90%.

Upon hydration, coarse liposomes are formed that incorporate a therapeutically effective amount of the light activated drugs-phospholipid complex. The "therapeutically effective amount" can vary widely, depending on the tissue to be treated and whether it is coupled to a target-specific ligand, such as an antibody or an immunologically active fragment. It should be noted that the various parameters used for selective photodynamic therapy are interrelated. Therefore, the therapeutically effective amount should also be adjusted with respect to other parameters, for example, fluence, irradiance, duration of the light used in photodynamnic therapy, and the time interval between administration of the light activated drug and the therapeutic irradiation. Generally, all of these parameters are adjusted to produce significant damage to tissue deemed undesirable, such as neovascular or tumor tissue, without significant damage to the surrounding tissue, or to enable the observation of such undesirable tissue without significant damage to the surrounding tissue.

Typically, the therapeutically effective amount is such to produce a dose of light activated drug within a range of from about 0.1 to about 20 mg/kg, preferably from about 0.15–2.0 mg/kg and, even more preferably, from about 0.25 to about 0.75 mg/kg. Preferably, the w/v concentration of the light activated drug in the composition ranges from about 0.1 to about 8.0–10.0 g/L. Most preferably, the concentration is about 2.0 to 2.5 g/L.

The hydration step should take place at a temperature that does not exceed about 30° C., preferably below the glass transition temperature of the light activated drug-phospholipid complex formed, even more preferably at room temperature or lower, e.g., 15°–20° C. The glass transition temperature of the light activated drug-lipid complex can be measure by using a differential scanning microcalorimeter.

In accordance with the usual expectation that the aqueous solubility of a substance should increase as higher temperatures are used, at a temperature around the transition temperature of the complex, the lipid membrane tends to undergo phase transition from a "solid" gel state to a pre-transition state and, finally, to a more "fluid" liquid crystal state. At these higher temperatures, however, not only does fluidity increase, but the degree of phase separation and the proportion of membrane defects also increases. This results in an increasing degree of leakage of the light-activated drug from inside the membrane to the interface and event out into the aqueous phase. Once a significant amount of liposome leakage has occurred, even slight changes in the conditions such as a small drop in temperature, can shift the equilibrium away from aqueous "solubility" in favor of precipitation of the light activated drug. Moreover, once the typically water-insoluble light activated drug begins to precipitate, it is not possible to re-encapsulate it when the lipid bilayer. The precipitate is thought to contribute significantly to filterability problems.

In addition, the usual thickness of a lipid bilayer in the "solid" gel state (about 47 Å) decreases in the transition to the "liquid" crystalline state to about 37 Å, thus shrinking the entrapped volume available for the light activated drugs to occupy. The smaller "room" is not capable of containing as great a volume of light activated drug, which can then be squeezed out of the saturated lipid bilayer interstices. Any two or more liposomes exuding light activated drug may aggregate together, introducing further difficulties with respect to particle size reduction and ease of sterile filtration. Moreover, the use of higher hydration temperatures, such as, for example, about 35° to 45° C., can also result in losses of light activated drug potency as the light activated drug either precipitates or aggregates during aseptic filtration.

The particle sizes of the coarse liposomes first formed in hydration are then homogenized to a more uniform size, reduced to a smaller size range, or both, to about 150 to 300 nm, preferably also at a temperature that does not exceed about 30° C., preferably below the glass transition temperature of the light activated drug-phospholipid complex formed in the hydration step, and even more preferably below room temperature of about 25° C. Various high-speed agitation devices may be used during the homogenization step, such as a Microfluidizer™ model 110F; a sonicator, a high-shear mixer; a homogenizer; or a standard laboratory shaker.

It has been found that the homogenization temperature should be at room temperature or lower, e.g., 15°–20° C. At higher homogenization temperatures, such as about 32°–42° C., the relative filterability of the liposome composition may improve initially due to increased fluidity as expected, but then, unexpectedly, tends to decrease with continuing agitation due to increasing particle size.

Preferably, a high pressure device such a Microfluidizer™ is used for agitation. In microfluidization, a great amount of heat is generated during the short-period of time during which the fluid passes through a high pressure interaction chamber. In the interaction chamber, two streams of fluid at a high speed collide with each other at a 90° angle. As the nicrofluidization temperature increases, the fluidity of the membrane also increases, which initially makes particle size reduction easier, as expected. For example, filterability can increase by as much as four times with the initial few passes through a Microfluidizer™ device. The increase in the fluidity of the bilayer membrane promotes particle size reduction, which makes filtration of the final composition easier. In the initial several passes, this increased fluidity mechanism advantageously dominates the process.

However, as the number of passes and the temperature both increase, more of the hydrophobic light activated drug molecules are squeezed out of the liposomes, increasing the tendency of the liposomes to aggregate into larger particles. At the point at which the aggregation of vesicles begins to dominate the process, the sizes cannot be reduced any further. Surprisingly, particle sizes actually then tend to grow through aggregation.

For this reason, the homogenization temperature is cooled down to and maintained at a temperature no greater than room temperature after the composition passes through the zone of maximum agitation, e.g., the interaction chamber of a Microfluidizer™ device. An appropriate cooling system can easily be provided for any standard agitation device in which homogenization is to take place, e.g., a Microfluidizer™, such as by circulating cold water into an appropriate cooling jacket around the mixing chamber or other zone of maximum turbulence. While the pressure used in such high pressure devices is not critical, pressures from about 10,000 to about 16,000 psi are not uncommon.

As a last step, the compositions are preferably aseptically filtered through a filter having an extremely small pore size, i.e., 0.22 μm. Filter pressures used during sterile filtration can vary widely, depending on the volume of the composition, the density, the temperature, the type of filter, the filter pore size, and the particle size of the liposomes. However, as a guide, a typical set of filtration conditions would be as follows: filtration pressure of 15–25 psi; filtration load of 0.8 to 1.5 ml/cm$^2$; and filtration temperature of about 25° C.

A typical general procedure is described below with additional exemplary detail:

(1) Sterile filtration of organic solvent through a hydrophobic, 0.22 μm filter.

(2) Addition of EPG, DMPC, light activated drug, and excipients to the filtered organic solvent, dissolving both the excipients and the light activated drug.

(3) Filtration of the resulting solution through a 0.22 μm hydrophobic filter.

(4) Transfer of the filtrate to a rotary evaporator apparatus, such as that commercially available under the name Rotoevaporator™.

(5) Removal of the organic solvent to form a dry lipid film.

(6) Analysis of the lipid film to determine the level of organic solvent concentration.

(7) Preparation of a 10% lactose solution.

(8) Filtration of the lactose solution through a 0.22 μm hydrophilic filter.

(9) Hydration of the lipid film with a 10% lactose solution to form coarse liposomes.

(10) Reduction of the particle sizes of the coarse liposomes by passing them through a Microfluidizer™ three times.

(11) Determination of the reduced particle size distribution of liposomes.

(12) Aseptic filtration of the liposome composition through a 0.22 μm hydrophilic filter. (Optionally, the solution may first be pre-filtered with a 5.0 μm prefilter.)

(13) Analysis of light activated drug potency.

(14) Filling of vials with the liposome composition.

(15) Freeze-drying.

Once formulate the liposome composition may be freeze-dried for long-term storage if desired. For example, BPD-MA, a preferred light activated drug, has maintained its potency in a cryodesiccated liposome composition for a period of at lest nine months at room temperature, and a shelf life of at least two years has been projected. If the composition is freeze dried, may be packed in vials for subsequent reconstitution with a suitable aqueous solution, such as sterile water or sterile water containing a saccharide and/or other suitable excipients, prior to administration, for example, by injection.

Preferably, liposomes that are to be freeze-dried are formed upon the addition of an aqueous vehicle contain a disaccharide or polysaccharide during hydration. The composition is then collected, placed into vials, freeze-dried, and stored, ideally under refrigeration. The freeze-dried composition can then be reconstituted by simply adding water for injection just prior to administration.

The liposomal composition provides liposomes of a sufficiently small and narrow particle size that the aseptic filtration of the composition through a 0.22 μm hydrophilic filter can be accomplished efficiently and with large volumes of 500 ml to a liter or more without significant clogging of the filter. A particularly preferred particle size range is below about 300 nm, more preferably below from about 250 nm. Most preferably, the particle size is below about 220 nm.

Generally speaking, the concentration of the light activated drugs in the liposome depends upon the nature of the light activated drug used. When BPD-MA is used for example, the light activated drug is generally incorporated in the liposomes at a concentration of about 0.10% up to 0.5% w/v. If freeze-dried and reconstituted, this would typically yield a reconstituted solution of up to about 5.0 mg/ml light activated drug.

For diagnosis, the light activated drugs incorporated into liposomes may be used along with, or may be labeled with, a radioisotope or other detecting means. If this is the case, the detection means depends on the nature of the label. Scintigraphic labels such as technetium or indium can be detected using ex vivo scanners. Specific fluorescent labels can also be used but, like detection based on fluorescence of the light activated drugs themselves, these labels can require prior irradiation.

The methods of preparing various light activated drugs, light activated drug conjugates, emulsions and microbubbles are described in greater detail in the examples below. These examples are readily adapted to preparing analogous light activated drugs, light activated drug conjugates, emulsions and microbubbles by substitutions of appropriate light activated drugs, site directing molecule, phospholipids, and other analogous components. The following examples are being presented to describe the preferred components, embodiments, utilities and attributes of the media. For example, although BPD-MA is used as the light activated drugs in the microbubble (liposome) examples, the invention is not intended to be limited to this particular light activated drug.

Example 1 describes the synthesis of a preferred texaphyrin derivative. Examples 2–4 describe different light activated drugs conjugated with oligonucleotides as site directing molecules. Examples 5 and 6 describes a synthesis of an emulsion including a light activated drug. Example 7 describes preparation of microbubbles which include a light activated drug.

EXAMPLE 1

Synthesis of Texaphyrin T2BET Metal Complexes

The synthesis of texaphyrins is provided in U.S. Pat. Nos. 4,935,498, 5,162,509 and 5,252,720, all incorporated by reference herein. The present example provides the synthesis of a preferred texaphyrin, named T2BET, having substituents containing ethoxy groups.

Lutetium(III) acetate hydrate can be purchased from Strem Chemicals, Inc. (Newburyport, Mass.), gadolinium (III) acetate tetrahydrate can be purchased from Aesar/Johnson Matthey (Ward Hill, Mass.) and LZY-54 zeolite can be purchased from UOP (Des Plaines, Ill.). Acetone, glacial acetic acid, methanol, ethanol isopropyl alcohol, and n-heptanes can be purchased from J. T. Baker (Phillipsburg, N.J.). Triethylamine and Amberlite 904 anion exchange resin can be purchased from Aldrich (Milwaukee, Wis.). All chemicals should be ACS grade and used without further purification.

Figure 22I:
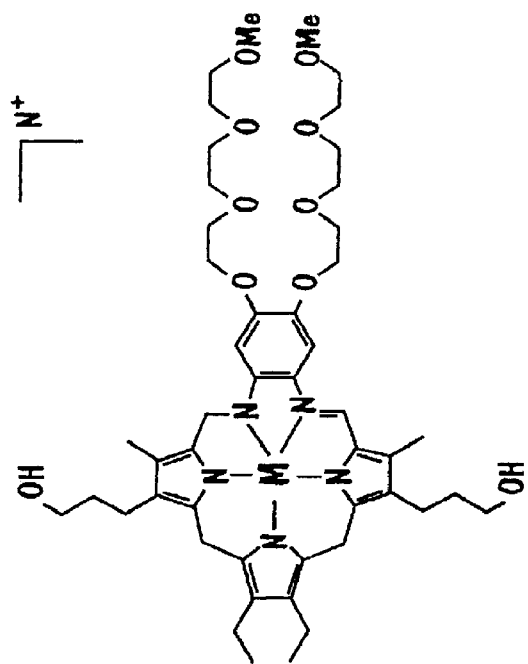
Figure 22H:
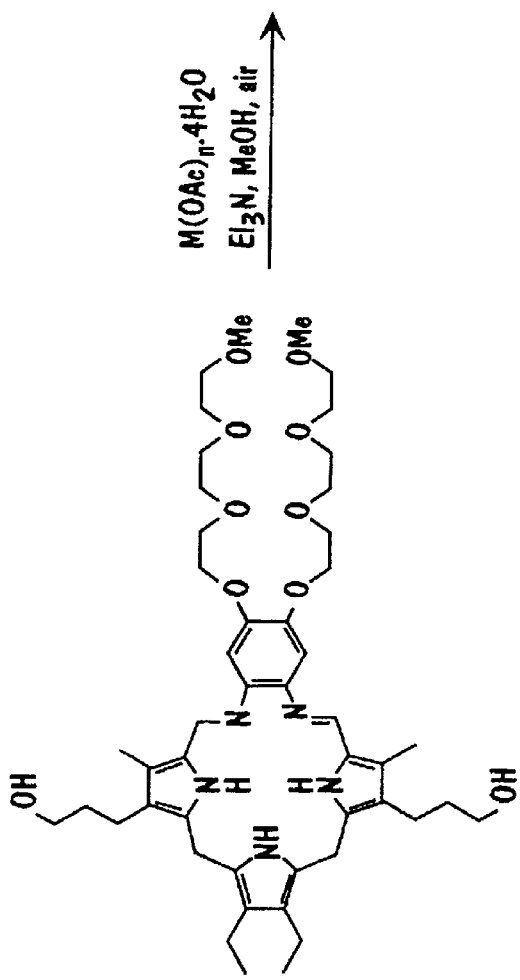
Figure 24A:
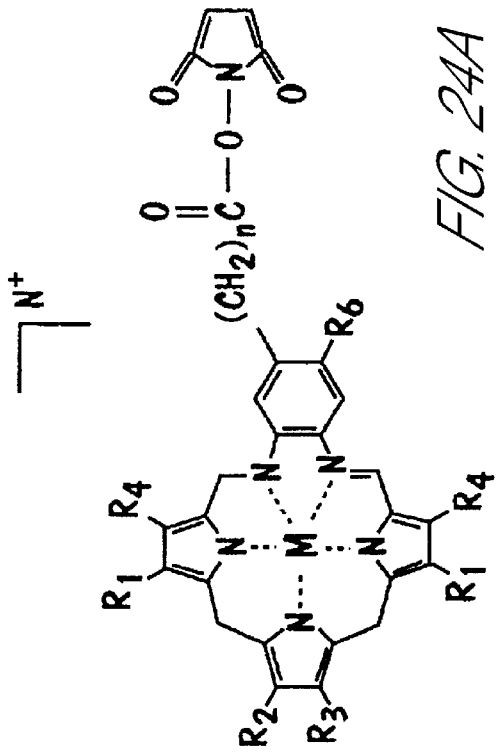
Figure 24B:
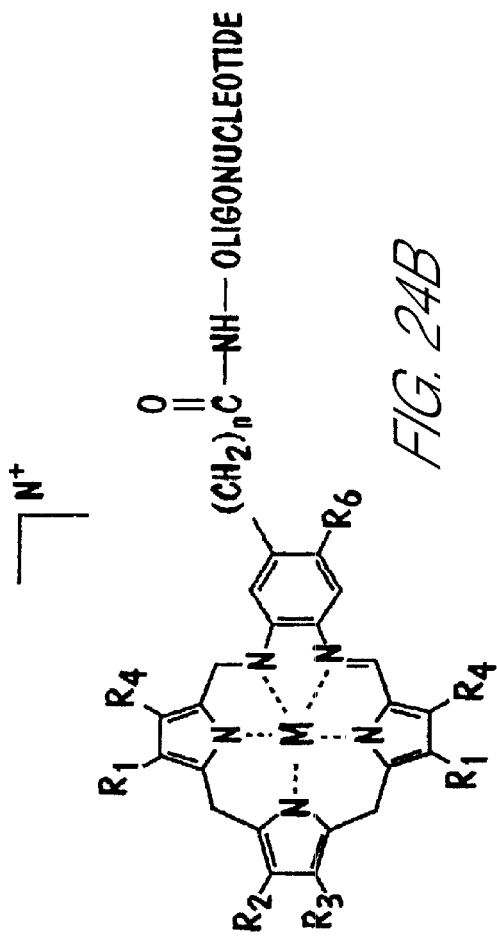
Figure 24C:
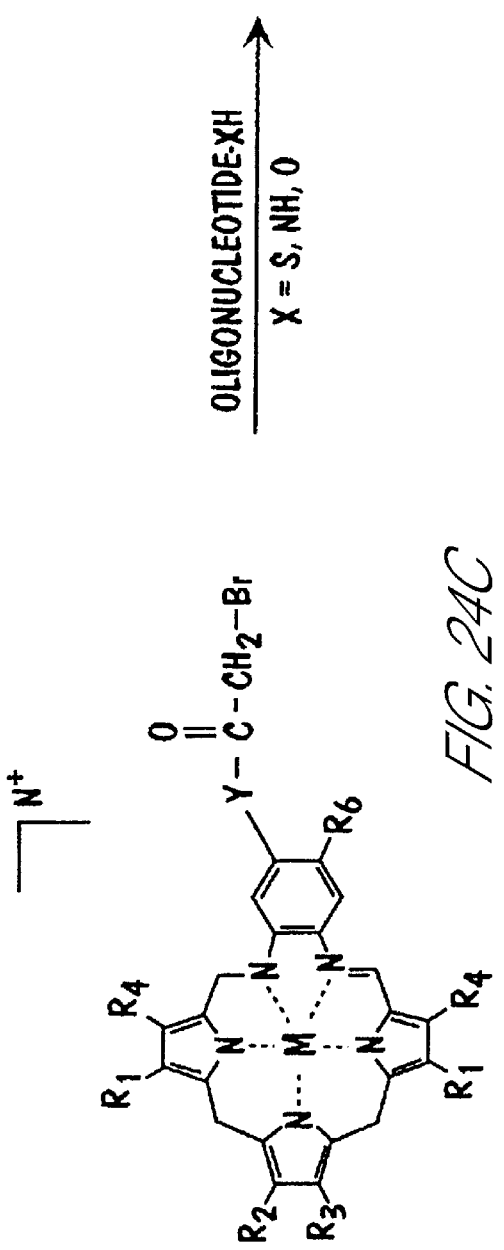
Figure 24D:
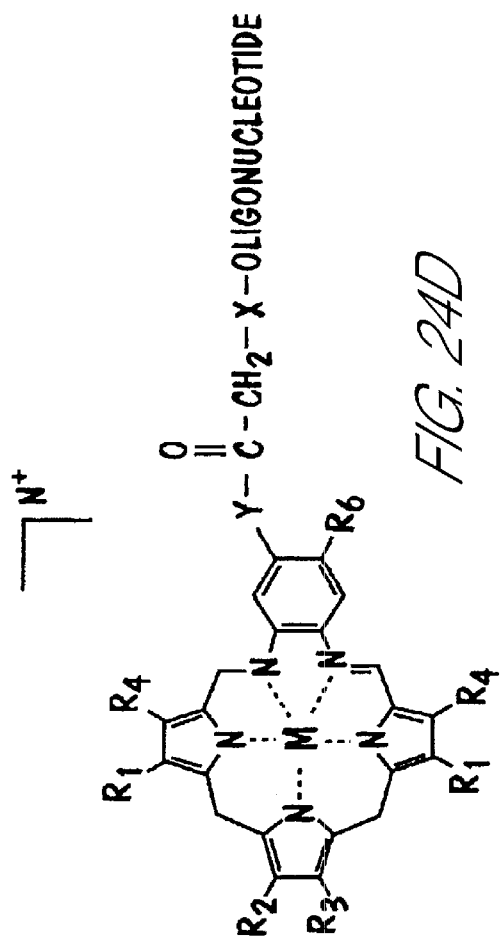

FIGS. 22A–I illustrate the synthesis of the gadolinium (III) complex of 4,5-diethyl- 10,23-dimethyl-9,24bis(3-hydroxypropyl)-16,17-bis[2-[2-(2-methoxyethoxy)ethoxy] ethoxy]- pentaazapentacyclo [20.2.1.1$^{3,6}$.1$^{8,11}$.0$^{14,19}$] heptacosa-1,3,5,7,9,11(27),12,14,16,18,20,22(25),23-tridecaene which is illustrated as Formula I of FIG. 22. The critical intermediate 1,2-bis[2-[2- (2-methoxyethoxy) ethoxy]ethoxy]-4,5-dinitrobenzene (Formula E) can be prepared according to a three-step synthetic process outlined in FIGS. 22A–I. (Note: References to "Formula A," "Formula B," etc. relate to FIGS. 22A, 22B, etc.)

Synthesis of triethylene glycol monomethyl ether monotosylate, Formula B: In an oven dried 12 L three-necked roundbottom flask, equipped with a magnetic stir bar and a 1000 mL pressure-equalizing dropping funnel, a solution of NaOH (440.0 g, 11.0 mol) is added to 1800 mL water and the mixture is cooled to approximately 0° C. A solution of triethylene glycol monomethyl ether, Formula A, (656.84 g, 4.0 mol) in THF (1000 mL) is added. The clear solution is stirred vigorously at 0° C. for 15 min and a solution of tosyl chloride (915.12, 4.8 mol) in THF (2.0 L) added dropwise over a 1 h period. The reaction mixture is stirred for an additional 1 h at O° C., and 10% HCl (5.0 L) is added to quench the reaction (to pH 5–7). The two-phase mixture is transferred to a 4 L separatory funnel the organic layer removed, and the aqueous layer extracted with t-butylmethyl ether (3×250 mL). The combined organic extracts are washed with brine (2×350 mL), dried (MgSO$_4$), and evaporated under reduced pressure to afford Formula B, 1217.6 g (95%) as a light colored oil. This material is taken to the next step without further purification.

Synthesis of 1,2-bis[2-[2-(2-methoxyethoxy)ethoxy] ethoxy]benzene, Formula D: In a dry 5 L round-bottom flask equipped with an overhead stirrer, reflux condenser, and a gas line, K$_2$CO$_3$ (439.47 g, 3.18 mol) and MeOH (1800 mL) are combined under an argon atmosphere. To this well-stirred suspension, catechol, Formula C, (140.24 g, 1.21 mol) is added, and the mixture heated to reflux. Formula B (1012.68 g, 3.18 mol) is then added in one portion. The suspension is stirred at reflux for 24 h, cooled to room temperature, and filtered through Celite. The pad is rinsed with 500 mL of methanol and the combined filtrates are evaporated under reduced pressure. The resulting brown residue is taken up in 10% NaOH (800 mL), and methylene chloride (800 mL) added with stirring. The mixture is transferred to a 2 L separatory funnel, the organic layer removed and the aqueous layer extracted with methylene chloride (3×350 mL). The organic extracts are combined, washed with brine (350 mL), dried (MgSO$_4$), evaporated under reduced pressure, and the residue dried in vacuo for several hours to yield 485.6 (95%) of 1,2-bis[2-[2-(2-methoxyethoxy)ethoxy]ethoxy)benzene (Formula D). For Formula D: bp. 165°–220° C., (0.2–0.5 mm Hg); FAB MS, M$^+$:m/e 402; HRMS, M$^+$: 402.2258 (calcd. for C$_{20}$H$_{34}$O$_8$, 402.2253).

Synthesis of 1,2-bis[2-[2-methoxy-ethoxy)ethoxy] ethoxy]-4,5-dinitrobenzene, Formula E: In an oven dried 1 roundbottom flask Formula D (104 g, 0.26 mol) and glacial acetic acid (120 mL) are combined and cooled to 5° C. To this well stirred solution, concentrated nitric acid (80 mL) is added dropwise over 15–20 min. The temperature of the mixture is held below 40° C. by cooling and proper regulation of the rate of addition of the acid. After addition, the reaction is allowed to stir for an additional 10–15 min and is then cooled to 0° C. Fuming nitric acid (260 mL) is added dropwise over 30 min while the temperature of the solution is held below 30° C. After the addition is complete, the red colored solution is allowed to stir at room temperature until the reaction is complete (ca 5 h, TLC: 95/5; CH$_2$Cl$_2$/MeOH) and then poured into well stirred ice water (1500 mL). Methylene chloride (400 mL) is added, the two-phase mixture transferred to a 2 L separatory funnel and the organic layer removed. The aqueous layer is extracted with CH2C12 (2×15O mL) and the combined organic extracts washed with 10% NaOH (2×250 mL) and brine (250 mL), dried (MgSO$_4$), and concentrated under reduced pressure. The resulting orange oil is dissolved in acetone (100 mL), and the solution layered with n-hexanes (500 mL), and stored in the freezer. The resulting precipitate is collected by filtration yield 101.69 g (80%) of Formula E as a yellow solid. For Formula E: mp 43°–45° C.; FAB MS, (M+H)$^+$: m/e 493; HRMS, (M+H)$^+$; 493; HRMS, (M+H)$^+$: 493.2030 (calcd. for C$_{20}$H$_{33}$N$_2$O$_{12}$, 493.2033).

Synthesis of 1,2-diamino-4,5-bis[2-[2-(2-methoxy-ethoxy)ethoxy]ethoxy], Formula F: In an oven dried 500 mL round bottom flask, equipped with a Claisen adapter, pressure equalizing dropping funnel, and reflux condenser, 1,2-bis[2-[2-2-methoxyethoxy)ethoxy]ethoxy]-4, 5dinitrobenzene (Formula E) (20 g, 0.04 mol) is dissolved in absolute ethanol (200 mL). To this clear solution, 10% palladium on carbon (4 g) is added and the dark black suspension is heated to reflux under an argon atmosphere. Hydrazine hydrate (20 mL) in EtOH (20 mL) is added dropwise over 10 min to avoid bumping. The resulting brown suspension is heated at reflux for 1.5 h at which time the reaction mixture is colorless and TLC analysis (95/5; CH$_2$Cl$_2$/MeOH) displays a low R/UV active spot corresponding to the diamine. Therefore, the mixture is hot filtered through Celite and the pad rinsed with absolute ethanol (50 mL). The solvent is removed under reduced pressure and the resulting light brown oil is dried in vacuo (in the dark) for 24 h to yield 15.55 g (89%) of 1,2-diamino-bis[2-[2-(2-methoxyethoxy)ethoxy]ethoxy]benzene (Formula F). For Formula F: FAB MS,M+: m/e 432; HRMS, M+: 432.2471 (calcd. for C$_{20}$H$_{36}$N$_2$O$_8$, 432.2482). This material is taken to the next step without further purification.

Synthesis of 4,5-diethyl-10,23-dimethyl-9,24-bis(3-hydroxypropyl)-16,17-bis[2-[2-(2-methoxyethoxy)ethoxy] ethoxy]-13,20,25,26,27-pentaazapentacyclo[20.2.1.1$^{3,6}$. 18, 11.0$^{14,19}$] heptacosa-3,5,8,10,12,14,16,18,20,22, 24undecaene, Formula H. In an oven dried 1 L round-bottom flask, 2,5-bis[(5-formyl-3(3-hydroxypropyl)4-methyl-pyrrol-2yl)methyl]-3,4-diethylpyrrole (Formula G) (The synthesis of Formula G is provided in U.S. Pat. No. 5,252, 720, incorporated by reference herein.) (30.94) g, 0.0644 mol) and 4,5-diamino-bis[2[2-(2-methoxyethoxy)ethoxy) ethoxy]benzene (formula F) (28.79 g, 0.0644 mol) are combined in absolute methanol (600 mL) under an argon atmosphere. To this well stirred suspension, a mixture of concentrated hydrochloric acid (6.7 m:) in absolute methanol 200 mL is added in one portion. The mixture is gradually heated to 50° C., at which time the reaction goes from a cloudy suspension of starting materials to a dark red homogeneous solution as the reaction proceeded. After 3 h the reaction is judged complete by TLC analysis and UV/visible spectroscopy ($\lambda_{max}$ 369 nm). The reaction mixture is cooled to room temperature, 60 g of activated carbon (DARCO™) is added, and the resulting suspension is stirred for 20 min. The dark suspension is filtered through Celite to remove the carbon, the solvent evaporated to dryness, and the crude Formula H dried in vacuo overnight. Formula H is recrystallized from isopropyl alcohol/n-heptane to afford 50 g (85%) of a scarlet red solid. For Formula H: $^1$H NMR (CD$_3$OD): δ1.11 (t, 6H, CH$_2$CH$_3$), 1.76 (p, 4H, pyrr-CH$_2$CH$_2$CH$_2$OH), 2.36 (s, 6H, pyrr-CH$_3$), 2.46 (q, 4H, CH$_2$CH$_3$), 2.64 (t, 4H, pyrr-CH$_2$CH$_2$CH$_2$OH), 3.29 [s, 6H, (CH$_2$CH$_2$O)$_3$CH$_3$], 3.31 (t, 4H, pyrr-CH$_2$CH$_2$CH$_2$OH), 3.43–3.85 (m, 20H, CH$_2$CH$_2$OCH$_2$CH$_2$OCH$_2$CH$_2$O), 4.0 (s, 4H, (pyrr)$_2$—CH$_2$), 4.22 (t, 4H, PhOCH$_2$CH$_2$O), 7.45 (s, 2H, PhH), 8.36 (s, 2H, HC=N); UV/vis: [(MeOH)λ$_{max}$ nm]: 369; FAB MS, [M+H]$^+$: m/e 878.5; HRMS, [M+H]$^+$: m/e 878.5274 (calcd. for [C$_{48}$H$_{72}$N$_5$O$_{10}$]$^+$ 878.5279).

Synthesis of the gadolinium (HI) complex of 4,5-diethyl-10,23-dimethyl-9,24-bis(3-hydroxypropyl)-16,17-bis[2-[2-(2-methoxyethoxy)ethoxy]ethoxy]pentaazapentacyclo [20.2.1.1$^{3.6}$,1$^{8.11}$, 0$^{14.19}$]heptacosa-1,3,5,7,9,11(27),12,14,16,18,20,22(25),23-tridecaene, Formula I. Formula I is prepared according to the process outlined in FIG. 22. In a dry 2 L three-necked round-bottom flask, Formula H (33.0 g, 0.036 mol) and gadolinium(II) acetate tetrahydrate (15.4 g, 0.038 mol) are combined in methanol (825 mL). To this well stirred red solution, gadolinium(III) acetate tetrahydrate (15.4 g, 0.038 mol) and triethylamine (50 mL) are added and the reaction is heated to reflux. After 1.5 h, air is bubbled (i.e., at reflux) for 4 h into the dark green reaction solution with aid of a gas dispersion tube (flow rate=20 cm$^3$/min). At this point, the reaction mixture is carefully monitored by UV/Visible spectroscopy (i.e., a spectrum is taken every 0.5–1 h,~1 drop diluted in 4–5 mL MeOH). The reaction is deemed complete by UV/Vis (In MeOH ratio: 342 nM/472 nm=0.22–0.24) after 4 h. The dark green reaction is cooled to room temperature, filtered through Celite into a 2 L round bottom flask, and the solvent removed under reduced pressure. The dark green solid is suspended in acetone (1 L) and the resulting slurry is stirred for 1 h at room temperature. The suspension is filtered to remove the red/brown impurities (incomplete oxidation products), the solids rinsed with acetone (200 mL), and air dried. The crude complex (35 g) is dissolved in MeOH (600 mL), stirred vigorously for 15 min, filtered through Celite, and transferred to a 2 L Erlenmeyer flask. An additional 300 mL of MeOH and 90 mL water are added to the flask, along with acetic acid washed LZY-54 zeolite (150 g). The suspension is agitated with an overhead mechanical stirrer for approximately 3–4 h. The zeolite extraction is deemed complete with the absence of free Gd(III). [To test for free gadolinium, the crude Formula I is spotted heavily onto a reverse phase TLC plate (Whatman KC8F, 1.5×10 cm) and the chromatogram developed using 10% acetic acid in methanol. The green complex moved up the TLC plate close to the solvent front. Any free gadolinium metal will remain at the origin under these conditions. After developing the chromatogram, the plate is dried and the lower ¼ of the plate stained with an Arsenazo III solution in methanol (4 mg Arsenazo III in 10 mL methanol). A very faint blue spot (indicative of free metal) is observed at the origin against a pink background indicating very little free gadolinium metal.] The zeolite is removed through a Whatman #3 filter paper and the collected solids rinsed with MeOH (200 mL). The dark green filtrate is loaded onto a column of Amberlite IRA-904 anion exchange resin (30 cm length×2.5 cm diameter) and eluted through the resin (ca. 10 mL/min flow rate) into a 2 L round bottom flask with 300 mL 1-butanol. The resin is rinsed with an additional 100 mL of MeOH and the combined eluent evaporated to dryness under reduced pressure. The green shiny solid Formula I is dried in vacuo for several hours at 40° C. to a well stirred ethanoic solution (260 mL of Formula I at 55°–60° C., n-heptanes (ca. 600 mL) is added dropwise (flow=4 mL/min) from a 1 L pressure-equalizing dropping funnel. During the course of 1.5 h (300 mL addition) the green Formula I began to crystallize out of the dark mixture. After complete addition, the green suspension is cooled and stirred for 1 h at room temperature. The suspension is filtered, the solids rinsed with acetone (250 mL), and dried in vacuo for 24 h to afford 26 g (63%), UV/vis: [(MeOH) λ$_{max}$nm]: 316, 350, 415, 473, 739; FAB MS, (M-20 Ac)$^+$: m/e 1030; HRMS, (M-20 Ac)$^+$: m/e 1027.4036 (calcd. for C$_{48}$H$_{66}$ $^{155}$GdN$_5$O$_{10}$, 1027.4016). Anal. calcd. for [C$_{52}$H$_{72}$GdN$_5$O$_{14}$] 0.5H$_2$O: C, 53.96: H, 6.36; N, 6.05, Gd, 13.59. Found: C, 53.73; H, 6.26; N, 5.82; Gd, 13.92.

Synthesis of the Lutetium(III) Complex of Formula H: The macrocyclic ligand Formula H is oxidatively metalated using lutetium(III) acetate hydrate (9.75 g, 0.0230 mol) and triethylamine (22 mL) in air-saturated methanol (1500 mL) at reflux. After completion of the reaction (as judged by the optical spectrum of the reaction mixture), the deep green solution is cooled to room temperature, filtered through a pad of celite, and the solvent removed under reduced pressure. The dark green solid is suspended in acetone (600 mL, stirred for 30 min at room temperature, and then filtered to wash away the red/brown impurities (incomplete oxidation products and excess triethylamine). The crude complex is dissolved into MeOH (300 mL, stirred for ~30 min, and then filtered through celite into a 1 L Erlenmeyer flask An additional 50 mL of MeOH and 50 mL of water are added to the flask along with acetic acid washed LZY-54 zeolite (40 g). The resulting mixture is agitated or shaken for 3 h, then filtered to remove the zeolite. The zeolite cake is rinsed with MeOH (100 mL and the rinse solution added to the filtrate. The filtrate is first concentrated to 150 mL and then loaded onto a column (30 cm length×2.5 cm diameter) of pretreated Amberlite IRA-904 anion exchange resin (resin in the acetate form). The eluent containing the bis-acetate lutetium(III) texaphyrin complex is collected. concentrated to dryness under reduced pressure, and recrystallized from anhydrous methanol/t-butylmethyl ether to afford 11.7 g(63%) of a shiny green solid. For the complex: UV/vis: [(MeOH) λ$_{max}$ nm, (log ε)]: 354,414, 474 (5.10), 672, 732; FAB MS, [IM-OAc$^-$]$^+$: m/e 1106.4; HRMS, (M-OAc$^{31}$ ]$^+$: m/e 1106.4330 (calcd. for [C$_{48}$H$_{66}$N$_5$;O$_{10}$Lu(OAc)]$^+$, 1106.4351). Anal. calcd. for [C$_{48}$H$_{66}$N5O$_{10}$Lu](OAc)$_2$H2O; C, 52.74; H, 6.30; N, 5.91. Found: C, 52.74; H, 6.18; N, 5.84.

EXAMPLE 2

Synthesis of a T2B1 TXP Metal Complex-Oligonucleotide Conjugate

FIGS 23A–H illustrate the synthesis of a light activated drug conjugate. The light activated drug is a texaphyrin coupled with an oligonucleotide which is complementary to a DNA site. As a result, the light activated drug conjugate can bind the complementary DNA site and will cleave the site upon activation by ultrasound. (Note: References to "Formula A," "Formula B," etc. relate to FIGS. 23A, 23B, etc.)

Synthesis of 4-Amino-1-[1-(ethyloxy)acetyl-2-oxy]-3-nitrobenzene (Formula B of FIG. 19), n=1. Potassium carbonate (14.0 g, 101 mmol) and 4-amino-3-nitrophenol (Formula A) (10.0 g, 64.9 mmol) are suspended in 150 mL dry acetonitrile. Ethyl-2-iodoacetate (10 mL, 84.5 mmol) (or ethyl iodobutyrate may be used, in that case n=3) is added via syringe, and the suspension is stirred at ambient temperature for ca 21 h. Chloroform (ca 375 mL) is added and is used to transfer the suspension to a separatory funnel, whereupon it is washed with water (2×ca 100 mL). The water washes are in turn washed with CHOl₃ (ca 100 mL) and the combined CHCl₃ extracts are washed with water (ca 100 mL). Solvents are removed on a rotary evaporator, and the residue is redissolved in CHCl₃ (ca 500 mL) and precipitated into hexanes (1.5 L). After standing two days, the precipitate is filtered using a coarse fritted funnel and dried in vacuo to provide 14.67 g (Formula B), n=1 (94.1%). TLC: Rf=0.43, CHCl₃.

Synthesis of 4-Amino-1-[1-(hydroxy)acetyl-2-oxy]-3-nitrobenzene (Formula C), n=1. 4-Amino-1-[1-(ethyloxy)acetyl-2-oxy]-3-nitrobenzene (Formula B), n=1, (10.00 g, 37.3 mmol) is dissolved in tetrahydrofuran (100 mL), aqueous sodium hydroxide(1M solution, 50 mL) is added and the solution is stirred at ambient temperature for ca. 21 h. Tetrahydrofuran is removed on a rotary evaporator, and water (100 mL) is added. The solution is washed with CHCl₃ (ca. 200 mL), the neutralized by addition of hydrochloric acid (1M solution, 50 mL). The precipitate which formed is filtered after standing a few minutes washed with water, and dried in vacuo to provide 8.913 g compound (Formula C), n=1 (99.5%). TLC: Rf=0.65, 10% methanol/CHCl₃.

Synthesis of 16-[1-(Hydroxy)acetyl-2-oxy]-9,24bis(3-hydroxypropyl)4,5-diethyl-10,23-dimethyl-13,20,25,26,27-pentaazapentacyclo [20.2.1.1$^{3.6}$.1$^{8.11}$.0$^{14.19}$]heptacosa-3,5,8,10,12,14(19), 15,17,20,22,24-undecaene (Formula E), n=1: 4-Amino-1-[1-(hydroxy)acetyl-2-oxy]-3-nitrobenzene (Formula C), n=1. (1,800 g, 8.49 mmol) is dissolved in methanol (100 mL) in a 1 L flask. Palladium on carbon (10%, 180 mg) is added, and the atmosphere inside the flask is replaced with hydrogen at ambient pressure. A grey precipitate is formed after ca 3 h, and the supernatant is clear. Methanol is removed in vacuo, taking precautions to prevent exposure to oxygen, and the compound is dried overnight in vacuo. Isopropyl alcohol (500 mL) and HCl (12M, 400 μL) are added, and the suspension is allowed to stir for ca. 15'. 2,5-Bis[(3-hydroxypropyl-5-formyl-4-methylpyrrol-2-y)methyl]-3,4-diethylpyrrole (Formula D) (n=1) (4.084 g, 8.49 mmol) is added, and the reaction stirred at room temperature under argon for 3 hours. Hydrochloric acid is again added (12M, 400 μL) and the reaction again is allowed to stir for an additional 3.5 h The resulting red solution is filtered through celite, and the filtercake is washed with isopropyl alcohol until the filtrate is colorless. Solvent is reduced to a volume of ca. 50 mL using a rotary evaporator, whereupon the solution is precipitated into rapidly stirring Et₂O (ca. 700 mL). Formula E (n=1) is obtained as a red solid (5.550 g, 98.4%) upon filtering and drying in vacuo. TLC: Rf=0.69, 20% methanol/CHCl₃ (streaks, turns green on plate with I₂).

Synthesis of metal complex of 16-[1-(hydroxy)acetyl-2-oxy]-9,24-bis(3-hydroxypropyl)-4,5-diethyl-10,23-dimethyl-13,20,25,26,27-pentaazapentacyclo [20.2.1.1$^{3.6.}$.1$^{8.11}$.0$^{14.19}$ ]heptacosa-1,3,5,7,9,11(27),12,14 (19),15,17,20,22(25),23-tridecaene (Formula F), n=1: Approximately equal molar amounts of the protonated form of the macrocycle, 16-[1-(hydroxy)acetyl-2-oxy]-9,24-bis (3-hydroxypropyl)-4,5-diethyl-10,23-dimethyl-13,20,25,26,27-pentaazapentacyclo[20.2.0.1.1$^{3.6.}$.1$^{8.11}$.0$^{14.19}$]heptacosa-3,5,8,10,12,14(19),15,17,20,22,24-undecaene hydrochloride (Formula E), n=1, and a metal acetate pentahydrate are combined with triethylamine in methanol, and are heated to reflux under air for 5.5 h. The reaction is cooled to room temperature, and stored at −20° C., overnight. Solvent is removed on a rotary evaporator, acetone is added, and the suspension is stirred on a rotary evaporator for 2 h. The suspension is filtered and the precipitate dried briefly in vacuo, whereupon a solution is formed in methanol (ca. 250 mL) and water (25 mL). The pH is adjusted to 4.0 using HCl (1M), HCl-washed zeolite LZY54 is added (ca. 5 g) and the suspension is stirred on the rotary evaporator for ca. 6 h. Amberlite™ IRA-900 ion exchange resin (NaF treated, ca. 5 g) is added, and the suspension is stirred for an additional hour. The suspension is filtered, the resin is washed with methanol (ca. 100 mL), and the filtrate is adjusted to pH 4.0 using HCl (1M). Solvents are removed on a rotary evaporator, using ethanol (abs.) to remove traces of water. After drying in vacuo, the compound is dissolved in methanol (25 mL) and precipitated into rapidly stirring Et₂O (300 mL). Formula F, n=1, is obtained as a precipitate after filtering and drying in vacuo. An analytical sample is prepared by treating 50 mg of Formula F, n=1, dissolved in methanol (25 mL) with acetic acid-washed zeolite, then acetic acid-washed Amberlite™ for ca. 1 h After reducing methanol to a minimum volume, the solution is precipitated into rapidly stirring Et₂O (70 mL), filtered, and dried in vacuo.

Postsynthetic modification of oligodeoxynucleotide-amine (Formula G) with metal complex (Formula F), n=1: The metal complex of 16-[1-(hydroxy)acetyl-2-oxy]-9,24-bis(3-hydroxypropyl)-4,5-diethyl-10,23dimethyl-13,20,25,26,27-pentaazapentacyclo [20.2.1.1$^{3.6}$.1$^{8.11}$.0$^{14.19}$] heptacosa-1,3,5,7,9,11(27),12,14(19),15,17,20,22(25),23-tridacaene (Formula F), n=1, (about 30 mol) and N-hydroxysuccinimide (43 μmol) are dried together overnight in vacuo. The compounds are dissolved in dimethylformamide (anhydrous, 500 μL) and dicyclohexylcarbodiimide (10 mg, 48 μmol) is added. The resulting solution is stirred under argon with protection from light for 8 h, whereupon a 110 μL aliquot is added to a solution of oligodeoxynucleotide (Formula G) (87 μmol) in a volume of 350 μL of 0.4M sodium bicarbonate buffer in a 1.6 mL Eppendorf tube. After vortexing briefly, the solution is allowed to stand for 23 h with light protection. The suspension is filtered through 0.45 μm nylon microfilterfuge tubes, and the Eppendorf tube is washed with 250 μL sterile water. The combined filtrates are divided into two Eppendorf tubes, and glycogen (20 mg/mL, 2 μL) and sodium acetate (3M, pH 5.4 30 μL) are added to each tube. After vortexing, ethanol (absolute, 1 mL) is added to each tube to precipitate the DNA. Ethanol is decanted following centrifugation, and the DNA is washed with an additional 1 mL aliquot of ethanol and allowed to air dry. The pellet is dissolved in 50% formamide gel loading buffer (20 μL), denatured at 90° C. for ca. 2', and loaded on a 20% denaturing polyacrylamide gel. The band corresponding to conjugate (Formula H), n=1, is cut from the gel, crushed and soaked in 1×TBE buffer (ca. 7 mL) for 1–2 days. The suspension is filtered through nylon filters (0.45 μm) and desalted using a Sep-pak™ reverse phase cartridge. The conjugate is eluted from the cartridge using 40% acetonitrile, lyophilized overnight, and dissolved in 1 mM HEPES buffer, pH 7.0 (500 μL). The solution concentration is determined using UV/vis spectroscopy.

EXAMPLE 3

Synthesis of Texaphyrin Metal Complexes with Amine-, Thiol- or Hydroxy-linked Oligonucleotides Amides, ethers, and thioethers are representative of linkages which may be used for coupling site-directing molecules such as oligonucleotides to light activated drugs such as texaphyrin metal complexes as illustrated in FIGS. 24A–F. (Note: References to "Formula A," "Formula b," etc. relate to FIGS. 24A, 24B, etc.) Oligonucleotides or other site-directing molecules functionalized with amines at the 5'-end, the 3'-end, or internally at sugar or base residues are modified post-synthetically with an activated carboxylic ester derivative of the texaphyrin complex. In the presence of a Lewis acid such as $FeBr_3$, a bromide derivatized texaphyrin (for example, Formula C of FIG. 24) will react with an hydroxyl group of an oligonucleotide to form and ether linkage between the texaphyrin linker and the oligonucleotide. Alternatively, oligonucleotide analogues containing one or more thiophosphate or thiol groups are selectively alkylated at the sulfur atom(s) with an alkyl halide derivative of the texaphyrin complex. Oligodeoxynucleotide-complex conjugates are designed so as to provide optimal catalytic interaction between the targeted DNA phosphodiester backbone and the texaphyrino.

Oligonucleotides are used to bind selectively compounds which include the complementary nucleotide or oligo- or polynucleotides containing substantially complementary sequences. As used herein, a substantially complementary sequence is one in which the nucleotides generally base pair with the complementary nucleotide and in which there are very few base pair mismatches. The oligonucleotide may be large enough to bind probably at least 9 nucleotides of complementary nucleic acid.

For general reviews of synthesis of DNA, RNA, and their analogues, see *Oligonucleotides and Analogues*, F. Eckstein, Ed., 1991. IRL Press, New York; *Oligonucleotide Synthesis*, M. J. Gait, Ed., 1984, IRL Press Oxford, England; Caracciolo et al. (1989); *Bioconjugate Chemistry*, Goodchild, J. (1990); or for phosphonate synthesis, Matteucci, Md. et al., *Nucleic Acids Res.* 14:5399 (1986) (these references are incorporated by reference herein).

In general, there are three commonly used solid phase-based approaches to the synthesis of oligonucleotides containing conventional 5'-3' linkages. These are the phosphoramidite method, the phosphonate method, and the triester method.

A brief description of a current method used commercially to synthesize oligomeric DNA is as follows: Oligomers up to ca. 100 residues in length are prepared on a commercial synthesizer, e.g., Applied Biosystems Inc. (ABI) model 392, that uses phosphoramidite chemistry. DNA is synthesized from the 3' to the 5' direction through the sequential addition of highly reactive phosphorous(III) reagents called phosphoramidites. The initial 3' residue is covalently attached to a controlled porosity silica solid support, which greatly facilitates manipulation of the polymer. After each residue is coupled to the growing polymer chain, the phosphorus(III) is oxidized to the more stable phosphorus(V) state by a short treatment with iodine solution. Unreacted residues are capped with acetic anhydride, the 5'-protective group is removed with weak acid, and the cycle may be repeated to add a further residue until the desired DNA polymer is synthesized. The full length polymer is released from the solid support, with concomitant removal of remaining protective groups, by exposure to base. A common protocol uses saturated ethanolic ammonia The phosphonate based synthesis is conducted by the reaction of a suitably protected nucleotide containing a phosphonate moiety at a position to be coupled with a solid phase-derivatized nucleotide chain having a free hydroxyl phosphonate ester linkage, which is stable to acid. Thus, the oxidation to the phosphate or thiophosphate can be conducted at any point during synthesis of the oligonucleotide or after synthesis of the oligonucleotide is complete. The phosphonates can also be converted to phosphoramidate derivatives by reaction with a primary or secondary amine in the presence of carbon tetrachloride.

In the triester synthesis, a protected phosphodiester nucleotide is condensed with the free hydroxyl of a growing nucleotide chain derivatized to a solid support in the presence of coupling agent. The reaction yields a protected phosphate linkage which may be treated with an oximate solution to form unprotected oligonucleotide.

To indicate the three approaches generically, the incoming nucleotide is regarded as having an "activated" phosphite/ phosphate group. In addition to employing commonly used solid phase synthesis techniques, oligonucleotides may also be synthesized using solution phase methods such as diester synthesis. The methods are workable, but in general, less efficient for oligonucleotides of any substantial length.

Preferred oligonucleotides resistant to in vivo hydrolysis may contain a phosphorothioate substitution at each base (*J. Org. Chem.* 55:4693–469, (1990) and Agrawal, (1990)). Oligodeoxynucleotides or their phosphorothioate analogues may be synthesized using an Applied Biosystem 380B DNA synthesizer (Applied Biosystems, Inc., Foster City, Calif.).

EXAMPLE 4

Figures 25C, 25D, 25E, 25F:
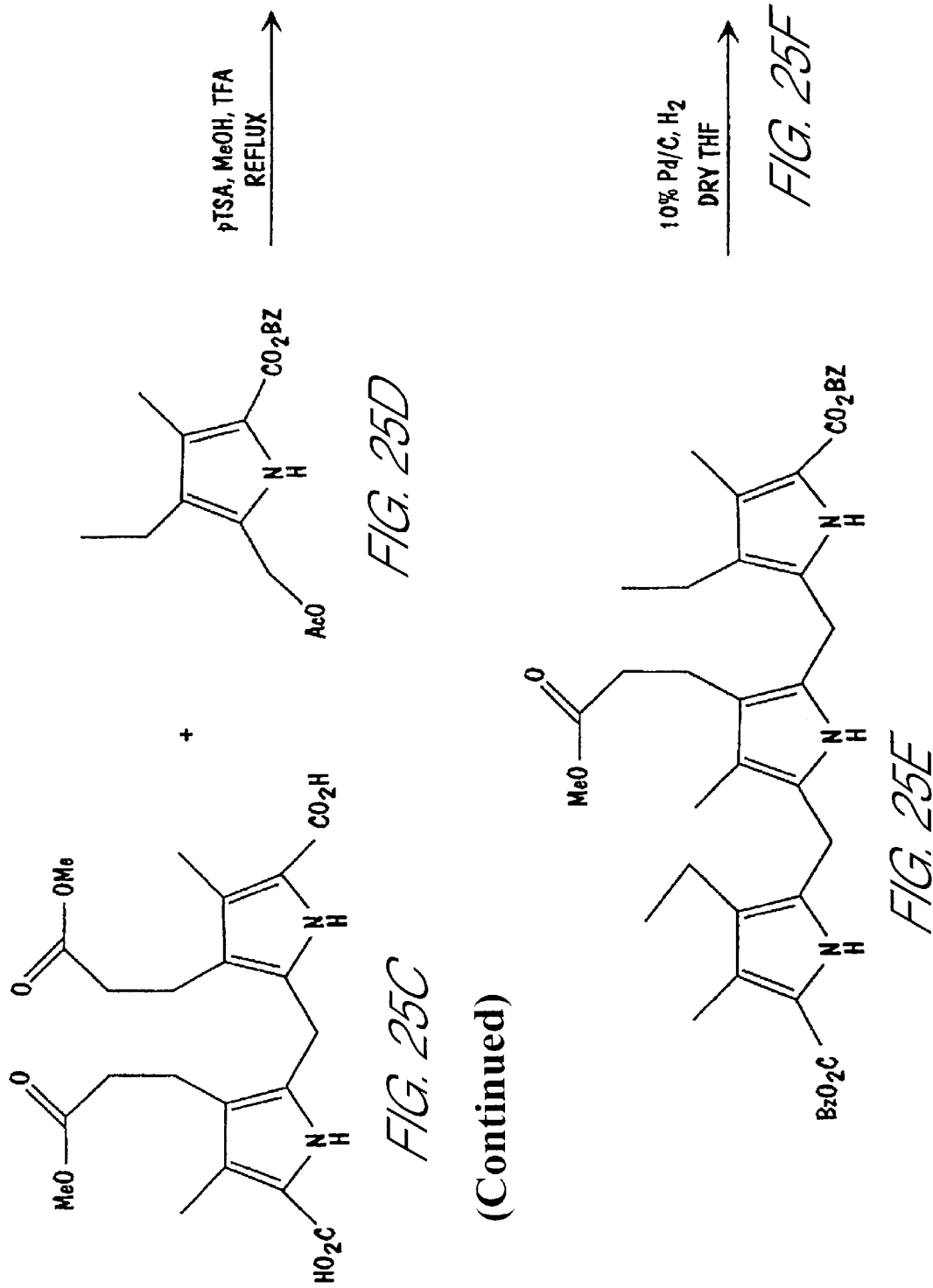
Figures 25F, 25G, 25H:
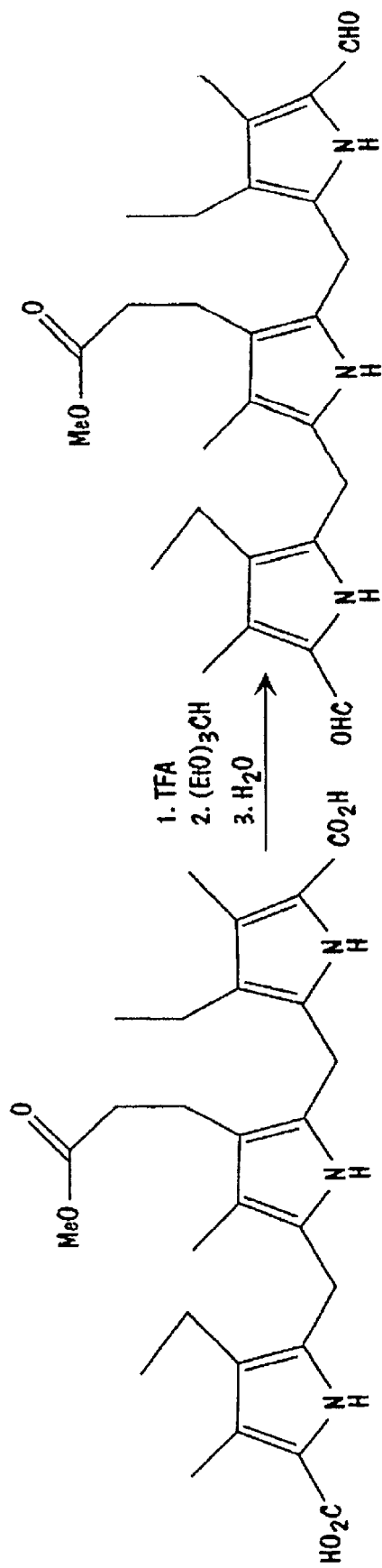

Synthesis of Diformyl Monoacid Tripyrrane (FIG. 25C, Formula H) and Oligonucleotide Conjugate (FIG. 25D, Formula J)

The present example provides for the synthesis of a light activated drug conjugate. The light activated drug conjugate includes a oligonucleotide acting as a site directing molecule coupled with the tripyrrane portion of a texaphyrin as illustrated in FIGS. 25A–J. (Note: References to "Formula A," "Formula b," etc. relate to FIGS. 25A, 25B, etc.)

Synthesis of Dimethylester Dibenzylester Dipyrromethane (Formula B): A three-neck 1000 mL round-bottom flask set with a magnetic stirring bar, a thermometer, a heating mantle, and a reflux condenser attached to an argon line is charged with methylester acetoxypyrrole (Formula A) (100.00 g; 267.8 mmol), 200 proof ethyl alcohol (580 mL), and deionized water (30 mL.) The reaction mixture is heated up and when the resulting solution begins to reflux, 12N aq. hydrochloric acid (22 mL) is added all at once. The flask contents are stirred under reflux for two hours. The heating element is replaced by a 0° C. bath and the resulting thick mixture is stirred for two hours prior to placing it in the freezer overnight.

The mixture is filtered over medium fritted glass funnel, pressed with a rubber dam, and washed with hexanes until the filtrate comes out colorless. The collected solids are set for overnight high vacuum drying at 30° C. to afford slightly yellowish solids (65.85 g, 214.3 mmol, 80.0% yield.)

Synthesis of Dimethylester Diacid Dipyrromethane, Formula C: All the glassware is oven dried. A three-neck 2000 mL round-bottom flask set with a magnetic stirring bar, a hydrogen line, and a vacuum line is charged with dimethylester dibenzylester dipyrromethane (Formula B) (33.07 g, 53.80 mmol), anhydrous tetrahydrofuran (1500 mL), and 10% palladium on charcoal (3.15 g.) The flask is filled with dry hydrogen gas after each of several purges of the flask atmosphere prior to stirring the reaction suspension under a hydrogen atmosphere for 24 hours.

The solvent of the reaction suspension is removed under reduced pressure. The resulting solids are dried under high vacuum overnight.

The dry solids are suspended in a mixture of saturated aqueous sodium bicarbonate (1500 mL) and ethyl alcohol (200 mL), and stirred at its boiling point for five minutes. The hot suspension is filtered over celite. The filtrate is cooled down to room temperature and acidified to pH 6 with 12N aqueous hydrochloric acid. The resulting mixture is filtered over medium fritted glass. The collected solids are dried under high vacuum to constant weight (21.63 g, 49.78 mmol, 92.5% yield.)

Synthesis of Methylester Dibenzylester Tripyrrane, Formula E: A three-neck 2000 mL round-bottom flask set with a heating mantle, a magnetic stirring bar, a thermometer, and a reflux condenser attached to an argon line is charged with dimethylester diacid dipyrromethane (Formula C) (21.00 g, 48.33 mmol), ethyl acetoxy pyrrole (Formula D) (30.50 g), p-toluenesulfonic acid monohydrate (1.94 g), trifluoroacetic acid (39 mL), and methyl alcohol (1350 mL.) The flask contents are heated and stirred under reflux for two hours. The heating element is replaced with a 0° C. bath and the stirring is continued for half an hour prior to placing the resulting mixture in a freezer overnight.

The cold mixture is filtered over medium fritted glass. The collected solids are washed with hexanes and dried under high vacuum overnight (13.05 g, 19.25 mmol, 39.85 yield).

Synthesis of Methylester Diacid Tripyrrane, Formula F: All the glassware is oven dried. A three-neck 500 mL round-bottom flask set with a magnetic stirring bar, a hydrogen line, and a vacuum line is charged with methylester dibenzylester tripyrrane (Formula E) (12.97 g, 19.13 mmol), anhydrous tetrahydrofuran (365 mL), and 10% palladium on charcoal (1.13 g.) The flask is filled with dry hydrogen gas after each of several purges of the flask atmosphere prior to stirring the reaction suspension for 24 hours under a hydrogen atmosphere at room temperature.

The reaction suspension is filtered over celite. The solvent of the filtrate is removed under reduced pressure to obtain a foam which is dried under high vacuum overnight (10.94 g, 21.99 mmol, 87.0% pure.)

Synthesis of Monoacid Tripyrrane, Formula H: All the glassware is oven dried. A three-neck 500 mL round-bottom flask set with a mechanical stirrer, a thermometer, a 0° C. bath, and an additional funnel set with an argon line is charged with methylester diacid tripyrrane (Formula F) (10.20 g, 17.83 mmol). Trifluoroacetic acid (32.5 mL) is dripped into the reaction flask from the addition funnel over a 45 minute period keeping the flask contents below 5° C. The resulting reaction solution is stirred at 0° C. for 15 minutes, and then at 20° C. for three hours. Triethylorthoformate (32.5 mL) is dripped into the flask from the addition funnel over a 20 minute period keeping the flask contents below −25° C. by means of a dry ice/ethylene glycol bath. The reaction solution is stirred for one hour at −25 ° C. and then a 0° C. bath is set up. Deionized water (32.5 mL) is dripped into the reaction flask from the addition funnel keeping the flask contents below 10° C. The resulting two phase mixture is stirred at room temperature for 75 minutes and then added 1-butanol (200 mL.) The solvents are removed under reduced pressure. The resulting dark oil is dried under high vacuum overnight to obtain black solids (11.64 g.)

A three-neck 2000 mL round-bottom flask set with a thermometer, a heating mantle, a magnetic stirring bar, and a reflux condenser attached to an argon line, is charged with the crude methylester diformyl tripyrrane (Formula G) (11.64 g), methyl alcohol (900 mL), deionized water (60 mL), and lithium hydroxide monohydrate (4.7 g.) The flask contents are heated, stirred under reflux for two hours, cooled down to room temperature, added deionized water (250 mL), acidified with 12N aq. HCl to pH 5, and then stirred at 0° C. for one hour. The resulting mixture is filtered over medium fritted glass funnel. The collected solids are dried under high vacuum to constant weight prior to their purification by column chromatography (silica gel, MeOH in $CH_2Cl_2$, 0–10%; 3.64 g, 8.06 mmol, 45.2% yield.)

The monoacid tripyrrane (Formula H) is condensed with a derivatized ortho-phenylene diamine to form a nonaromatic precursor which is then oxidized to an aromatic metal complex, for example, Formula I. An oligonucleotide amine may be reacted with the carboxylic acid derivatized texaphyrin Formula I to form the conjugate Formula J having the site-directing molecule on the T (tripyrrane) portion of the molecule rather than the B (benzene) portion.

EXAMPLE 5

Figure 26:
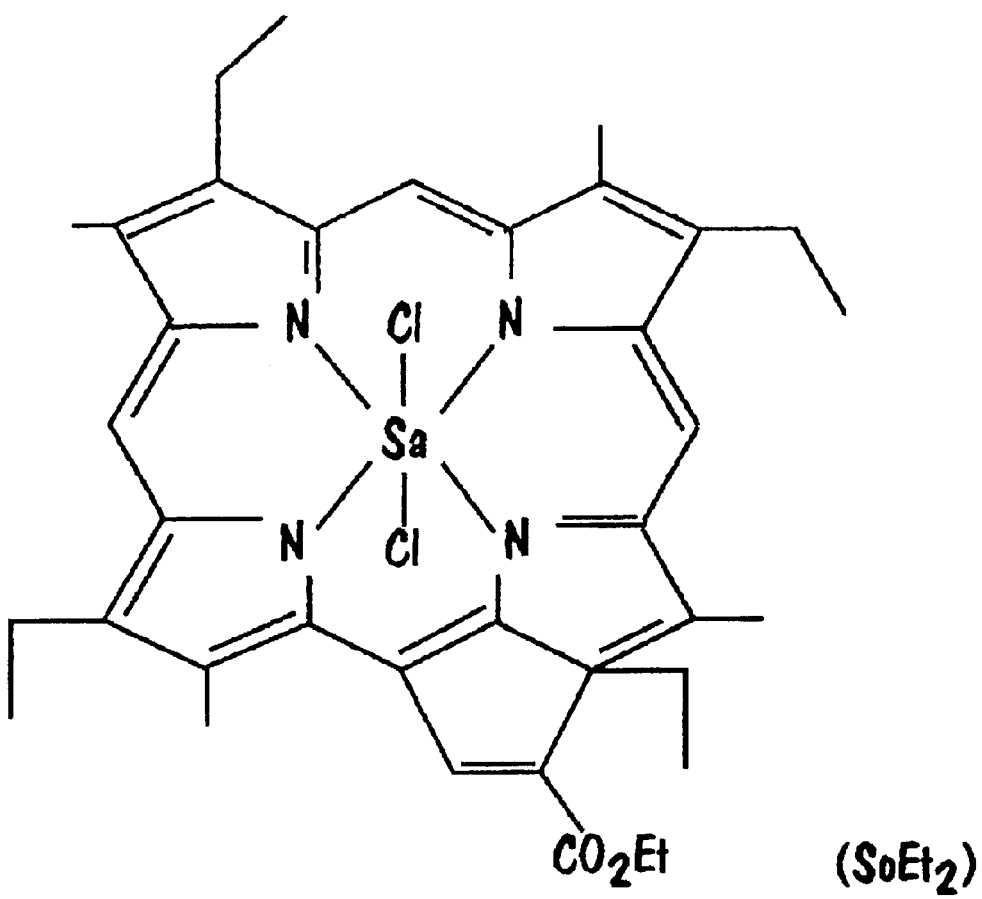
FIG. 26 illustrates the formula for tin ethyl etiopurpurin (SnEt$_2$).

The following example describes the synthesis of an emulsion including tin ethyl etiopurpurin ($SnEt_2$) which is illustrated in FIG. 26.

Several emulsions are prepared as described above. In 5 ml glass tubes, medium chain length oil known as MCT oil (Miglyol 801, Hüls America, Piscataway, N.J.) is combined with 10 mg/gm $SnEt_2$ plus excipients as described above. Certain emulsions also included additional excipients in the following concentrations: ethanol at mg/gm oil; egg phospholipids at 75 mg/gm oil; and sodium cholate at 10 mg/gm oil. After incubating for 30 minutes at 55° C., the tubes stand overnight at room temperature (19°–22° C.). The tubes are centrifuged to remove bulk precipitates, and supernatants are filtered through 0.45 μm nylon membrane to remove any undissolved drug. Aliquots of filtrate are then diluted in chloroform:isopropyl alcohol (1:1) for spectrophotometric determination of drug concentration (absorbance at 662 nm). Reference standards are prepared with known concentrations of $SnEt_2$ in the same solvent.

The concentration of $SnEt_2$ in each of the emulsions is illustrated in Table 2. As illustrated, the concentration of $SnEt_2$ in the emulsion can be more than ten times the concentration in MCT oil alone.

TABLE 2

Drug Solubility in Oil

| Excipient Combination Added to MCT Oil | $SnEt_2$ Concentration mg/gm oil | $SnEt_2$ Concentration Normalized |
|---|---|---|
| MCT oil alone | 0.38 | 1.00 |
| + ethanol | 0.28 | 0.74 |
| + egg phospholipids (EYP) | 0.89 | 2.34 |
| + Na cholate | 1.17 | 3.08 |
| + ethanol + EYP | 1.37 | 3.61 |
| + EYP + Na cholate | 1.77 | 4.66 |
| + ethanol + Na cholate | 2.20 | 5.79 |
| + ethanol + EYP + Na cholate | 4.92 | 12.95 |

EXAMPLE 6

This example illustrates relative efficiencies of several bile salts. Mixtures of MCT oil, egg phospholipids, ethanol, and $SnEt_2$ are incubated with different bile salts, all at 4.6 $mM^1$, under the same conditions described above. As shown in Table 3, sodium cholate is the most efficient solubilizer. Cholic acid lacks solubilizing action in the oil.

TABLE 3

Sodium Cholate is the Most
Efficient Co-Solubilizer for SnEt$_2$

| Bile compound | SnEt$_2$ Concentration mg/gm oil | SnEt$_2$ Concentration Normalized |
|---|---|---|
| None | 1.26 | 1.00 |
| Na Tauracholate | 1.13 | 0.90 |
| Cholic acid | 1.33 | 1.06 |
| Na glycocholate | 2.22 | 1.76 |
| Na deoxycholate | 2.31 | 1.83 |
| Na cholate | 3.70 | 2.94 | equivalent to sodium cholate addition at 10 mg per gram oil or 0.2% w/v in a 20% o/w emulsion
equivalent to sodium cholate addition at 10 mg per gram oil or 0.2% w/v in a 20% o/w emulsion

EXAMPLE 7

The following Example illustrates the preparation of liposomes including BPD-MA (See FIG. 17);as alight activated drug. A 100-ml batch of BPD-MA liposomes is prepared at room temperature (about 20° C.) using the following general procedure. BPD-MA, butylated hydroxytoluene ("BHT"), ascorbyl palmitate, and the phospholipids DMPC and EPG are dissolved in methylene chloride. The molar ratio of light activated drug: EPG:DMPC is 1.0:3.7 and has the compositions illustrated in Table 4.

TABLE 4

| Light activated drug | 0.21 g |
|---|---|
| EPG | 0.68 g |
| DMPC | 1.38 g |
| BHT | 0.0002 g |
| Ascorbic acid 6-palmitate | 0.002 g |
| Lactose NF crystaliine injectable | 10 g |
| Water for injection | 100 ml |

Using the above formulation, the total lipid concentration (% w/v) is about 2.06. The resulting solution is filtered through a 0.22 μm filter and then dried under vacuum using a rotary evaporator. Drying is continued until the amount of methylene chloride in the solid residue is no longer detectable by gas chromatography.

A 10% lactose/water-for-injection solution is then prepared and filtered through a 0.22 μm filter. Instead of being warmed to a temperature of about 35° C., the lactose/water solution is allowed to remain at room temperature (about 25° C.) for addition to the flask containing the solid residue of the light activated drug/phospholipid. The solid residue is dispersed in the 10% lactose/water solution at room temperature, stirred for about one hour, and passed through a Microfluidizer™ homogenizer three to four times with the outlet temperature controlled to about 200°–250° C. The solution is then filtered through a 0.22 μm Durapore, hydrophilic filter.

The filterability of the composition in g/cm$^2$ is typically greater than about 10. Moreover, the yield is about 100% by HPLC analysis, with light activated drug potency typically being maintained even after sterile filtration. Average particle sizes vary from about 150 to about 300 nm (±50 nm).

EXAMPLE 8

The following Example describes the delivery of a light activated drug to an atheroma. An emulsion is prepared having about 0.6 g SnEt$_2$/ml of emulsion and about 20 g of MCT oil based hydrophobic phase/ml of emulsion. The catheter illustrated in FIG. 7C is positioned in a vessel of the cardiovascular system using over the guidewire techniques. The catheter is positioned such that the media delivery port is adjacent to the atheroma using radiopaque markers on the catheter and the balloon is expanded into contact with the vessel wall. The emulsion is delivered via the third utility lumen 16B of the catheter 10. After the delivery of the emulsion, the ultrasound energy is delivered at about 0.3 W/cm$^2$ at a frequency of approximately 1.3 MHz for about ten minutes. After the delivery of ultrasound energy has concluded, the catheter is withdrawn from the vasculature of the tumor.

EXAMPLE 9

The following Example describes the delivery of a light activated drug to a tumor. An emulsion is prepared having approximately 0.8 g SnEt$_2$/ml of emulsion and approximately 30 g of MCT oil based hydrophobic phase/ml of emulsion. The catheter 10 illustrated in FIG. 3A is positioned in the vasculature of a tumor using over the guidewire techniques. The catheter is positioned such that the media delivery port is within the tumor using radiopaque markers included on the catheter. The prepared emulsion is delivered into the vasculature of the tumor via the utility lumen 16A. After the delivery of the emulsion, the ultrasound energy is delivered at about 0.3 W/cm$^2$ at a frequency of approximately 1.3 MHz for about fifteen minutes. After the delivery of ultrasound energy has concluded, the catheter is withdrawn from the vascular system of the patient.

EXAMPLE 10

The following Example describes the delivery of a light activated drug to a potential restenosis site. An emulsion is prepared having approximately 0.6 g SnEt$_2$/ml of emulsion and approximately 30 g of MCT oil based hydrophobic phase/ml of emulsion. The catheter illustrated in FIG. 7C is positioned in the vasculature of a patient using over the guidewire techniques. The catheter is positioned such that the media delivery port is adjacent to a portion of the vessel which was previously treated with balloon angioplasty and the balloon is expanded into contact with the vessel wall. The prepared emulsion is delivered into the vasculature of the patient via the third utility lumen 16B. Ultrasound energy is delivered from the ultrasound assembly to the potential restenosis site at about 0.3 W/cm$^2$ at a frequency of approximately 1.3 MHz for about ten minutes. After the delivery of ultrasound energy has concluded, the catheter is withdrawn from the vascular system of the patient.

EXAMPLE 11

The following Example describes the delivery of a light activated drug to an atheroma Liposomes are prepared including BPD-MA (See FIG. 17) as the light activated drug and DMPC and EPG as the phospholipids. The molar ratio of BPD-MA:EPG:DMPC is about 1:3:7. The catheter illustrated in FIG. 7C is positioned in a vessel of the cardiovascular system using over the guidewire techniques. The catheter is positioned such that the media delivery port is adjacent to the atheroma using radiopaque markers included on the catheter and the balloon is expanded into contact with the vessel. Ultrasound energy is delivered at about 0.3 W/cm$^2$ at a frequency of approximately 1.3 MHz for about 20 minutes in order to rupture the liposomes and cause tissue death within the atheroma. After the delivery of ultrasound energy has concluded, the catheter is withdrawn from the vascular system of the patient.

EXAMPLE 12

The following Example describes the delivery of a light activated drug to a tumor. Liposomes are prepared including BPD-MA (See FIG. 17) as the light activated drug and DMPC and EPG as the phospholipids. The molar ratio of BPD-MA:EPG:DMPC is about 1:3:7. The catheter illustrated in FIG. 8 is positioned in the vasculature of a tumor using over the guidewire techniques. The catheter is positioned such that the media delivery port is within the tumor using radiopaque markers included on the catheter. Ultrasound energy is delivered at about 0.3 W/cm$^2$ at a frequency of approximately 1.3 MHz for about 20 minutes in order to rupture the liposomes and cause tissue death within the atheroma After the delivery of ultrasound energy is concluded, the catheter is withdrawn from the vasculature of the tumor.

EXAMPLE 13

The following Example describes the delivery of a light activated drug to a potential restenosis site. Liposomes are prepared including BPD-MA (See FIG. 17) as the light activated drug and DMPC and EPG as the phospholipids. The molar ratio of BPD-MA:EPG:DMPC is approximately 1:3:7. The catheter illustrated in FIG. 7C is positioned in the vasculature of a patient using over the guidewire techniques. The catheter is positioned such that the media delivery port is adjacent to a portion of the vasculature which was previously treated with balloon angioplasty and the balloon is inflated into contact with the vessel wall. Ultrasound energy is delivered at about 0.3 W/cm$^2$ at a frequency of approximately 1.3 MHz for about 15 minutes in order to rupture the liposomes and cause tissue death within the atheroma. After the delivery of ultrasound energy is concluded, the catheter is withdrawn from the vasculature of the patient.

EXAMPLE 14

The following Example describes the delivery of a light activated drug to an atheroma. Liposomes are prepared including BPD-MA (See FIG. 17) as the light activated drug and DMPC and EPG as the phospholipids. The molar ratio of BPD-5 MA:EPG:DMPC is about 1:3:7. The phospholipids are systemically delivered. The catheter illustrated in FIG. 7C is positioned in the vasculature of a patient using over the guidewire techniques. The catheter is positioned such that the media delivery port is adjacent to the atheroma and the balloon is inflated into contact with the vessel wall. Ultrasound energy is delivered at about 0.3 W/cm$^2$ at a frequency of approximately 1.3 MHz for about 15 minutes. After the delivery of ultrasound energy is concluded, the catheter is withdrawn from the vasculature of the patient.

EXAMPLE 14

The following Example describes the delivery of a light activated drug to a tumor. Microbubbles are prepared including cisplatin and photofrin according to the methods disclosed in U.S. Pat. No. 5,770,222. The microbubbles are systemically administered. The catheter illustrated in FIG. 1A is positioned within the vasculature of a tumor. Ultrasound energy is delivered at about 0.3 W/cm$^2$ at a frequency of approximately 1.3 MHz for about 15 minutes. After the delivery of ultrasound energy is concluded, the catheter is withdrawn from the vasculature of the patient.

EXAMPLE 14

The following Example describes the delivery of a light activated drug to a tumor. Microbubbles are prepared including cisplatin and photofrin according to the methods disclosed in U.S. Pat. No. 5,770,222. The catheter illustrated in FIG. 3A is positioned within the vasculature of a tumor. The microbubbles are delivered to the tumor via the second utility lumen 16A of the catheter. Ultrasound energy is delivered at about 0.3 W/cm$^2$ at a frequency of approximately 1.3 MHz for about 15 minutes. After the delivery of ultrasound energy is concluded, the catheter is withdrawn from the vasculature of the patient.

EXAMPLE 16

The following Example describes the delivery of a light activated drug to a thrombosis. Microbubbles are prepared including heparin, photofrin and an albumin substrate. The microbubbles are systemically administered. The catheter illustrated in FIG. 1A is positioned adjacent to the thrombosis. Ultrasound energy is delivered at about 0.2 W/cm$^2$ at a frequency of approximately 1.3 MHz for about 20 minutes. After the delivery of ultrasound energy is concluded, the catheter is withdrawn from the vasculature of the patient.

What is claimed is:

1. A method for treating a subdermal tissue site, comprising:
   providing a catheter for locally delivering a light activated drug to the subdermal tissue site, the catheter including an ultrasound transducer;
   placing the catheter into the body near the tissue site;
   locally delivering the light activated drug to the tissue site;
   producing ultrasound energy from the ultrasound transducer; and
   directing the ultrasound energy to the subdermal tissue site following delivery of the light activated drug to the subdermal tissue site to activate at least a portion of the light activated drug.

2. The method of claim 1, further comprising directing ultrasound energy to the tissue site to enhance absorption of the light activated drug into the tissue site prior to activation of the light activated drug.

3. The method of claim 1, wherein directing the ultrasound energy to the subdermal tissue site includes positioning the ultrasound transducer adjacent the subdermal tissue site.

4. The method of claim 1, wherein the tissue site is selected from a group consisting of an atheroma and a tumor.

5. The method of claim 1, wherein locally delivering the light activated drug includes positioning a media delivery port included on the catheter adjacent the tissue site and delivering the media through the media port via the lumen in a catheter.

6. The method of claim 1, wherein locally delivering the light activated drug includes locally delivering a media with microbubbles.

7. The method of claim 6, wherein the microbubbles are liposomes.

8. The method of claim 1, wherein locally delivering the light activated drug includes locally delivering an emulsion with a lipoid as a hydrophobic phase dispersed in a hydrophylic phase.

9. The method of claim 1, wherein locally delivering the light activated drug includes locally delivering a site directing molecule coupled with the light activated drug, the site directing molecule having an affinity for an element of the tissue site.

10. The method of claim 9, wherein the site directing molecule is an oligonucleotide.

11. The method of claim 1, wherein the light activated drug is selected from the group consisting of GdT2BET, LuT2BET, SnEt$_2$ and T2B1 TXP Metal Complex-Oligonucleotide Conjugate.

12. The method of claim 1, wherein the light activated drug is selected from the group including photoreactive pyrrole-derived macrocycles and expanded pyrrole-based macrocycles.

13. The method of claim 1, wherein the light activated drug is selected from the group consisting of porphyrins, chlorins, bacteriochlorins, isobateriochlorins, phthalocyanines, naphtalocyanines, porphycenes, sapphyrins, texaphyrins, derivatives of porphyrins, derivatives of chlorins, derivatives of bacteriochlorins, derivatives of isobateriochlorins, derivatives of phthalocyanines, derivatives of naphtalocyanines, derivatives of porphycenes, derivatives of sapphyrins and derivatives of texaphyrins.

14. The method of claim 1, wherein the light activated drug includes a green porphyrin.

15. A method for activating a light activated drug, comprising:
   providing a catheter including an ultrasound transducer;
   placing the catheter into the body near the tissue site;
   introducing the light activated drug into a patient's body, wherein a subdermal tissue site absorbs at least a portion of the light activated drug;
   producing ultrasound energy;
   directing the ultrasound energy from said ultrasound transducer to the subdermal tissue site including the light activated drug; and
   activating at least a portion of the light activated drug in the subdermal selected tissue site.

16. The method of claim 15, wherein the ultrasound transducer is positioned to direct ultrasound energy into a wall of a blood vessel.

17. The method of claim 15, wherein a distal portion of the catheter is positioned in a patient's circulatory system.

18. The method of claim 15, wherein a distal portion of the catheter is positioned in a patient's blood vessel.

19. The method of claim 15, wherein the transducer is positioned to direct ultrasound energy in a lateral direction relative to a longitudinal axis of the catheter.

20. The method of claim 15, wherein the ultrasound transducer is positioned in an interior of the patient's body.

21. The method of claim 15, wherein the ultrasound transducer is positioned in an interior of a blood vessel.

22. The method of claim 15, wherein the ultrasound transducer is positioned adjacent to an atheroma.

23. The method of claim 15, wherein the ultrasound transducer is positioned adjacent to a tumor.

24. The method of claim 15, further comprising providing a temperature sensor on the catheter and measuring a temperature adjacent to the ultrasound transducer for adjusting a level of the ultrasound energy in response to the temperature.

25. A method for preventing restenosis, comprising:
   providing an elongate catheter having a drug delivery lumen and an ultrasound transducer mounted along a distal end portion;
   advancing the catheter through a patient's vasculature such that the distal end portion is located along a treatment site in a blood vessel;
   locally delivering an emulsion containing a light activated drug through the drug delivery lumen to the treatment site; and
   directing ultrasound energy from said ultrasound transducer along the treatment site to activate at least a portion of the light activated drug.

26. The method of claim 25, wherein the emulsion containing a light activated drug further comprises a plurality of microbubbles.

27. The method of claim 25, wherein the ultrasound energy is directed along the treatment site at about 0.3 W/cm$^2$ at a frequency of about 1.3 MHz for about 10 minutes.

28. The method of claim 25, further comprising providing a temperature sensor along the distal end portion of the catheter and measuring a temperature adjacent to the ultrasound transducer for adjusting a level of the ultrasound energy in response to the temperature.

* * * * *